US009999655B2

(12) United States Patent
Lander et al.

(10) Patent No.: US 9,999,655 B2
(45) Date of Patent: Jun. 19, 2018

(54) USE OF MKS INHIBITOR PEPTIDE-CONTAINING COMPOSITIONS FOR TREATING NON-SMALL CELL LUNG CANCER WITH SAME

(71) Applicant: Moerae Matrix, Inc., Morristown, NJ (US)

(72) Inventors: Cynthia Lander, Mendham, NJ (US); Colleen Brophy, Nashville, TN (US); Caryn Peterson, Encinitas, CA (US); Andrew Luber, Voorhees, NJ (US)

(73) Assignee: Moerae Matrix, Inc., Morristown, NJ (US)

( * ) Notice: Subject to any disclaimer, the term of this patent is extended or adjusted under 35 U.S.C. 154(b) by 0 days. days.

(21) Appl. No.: 15/066,976

(22) Filed: Mar. 10, 2016

(65) Prior Publication Data
US 2016/0263187 A1 Sep. 15, 2016

Related U.S. Application Data

(60) Provisional application No. 62/132,374, filed on Mar. 12, 2015.

(51) Int. Cl.
*A61K 33/24* (2006.01)
*A61K 45/06* (2006.01)
*A61K 38/17* (2006.01)
*A61K 9/00* (2006.01)
*A61M 11/00* (2006.01)
*A61M 15/00* (2006.01)

(52) U.S. Cl.
CPC ........ *A61K 38/1709* (2013.01); *A61K 9/0075* (2013.01); *A61K 9/0078* (2013.01); *A61K 33/24* (2013.01); *A61K 45/06* (2013.01); *A61M 11/00* (2013.01); *A61M 15/00* (2013.01); *A61M 2202/064* (2013.01)

(58) Field of Classification Search
CPC ................ A61K 2300/00; A61K 33/24; A61K 38/1709; A61K 45/06; A61K 9/0075; A61K 9/0078; A61K 9/00; A61K 38/17; A61M 11/00; A61M 15/00; A61M 2202/064
USPC ....................................................... 530/300
See application file for complete search history.

(56) References Cited

U.S. PATENT DOCUMENTS

| 4,105,027 A | 8/1978 | Lundquist |
| 4,192,309 A | 3/1980 | Poulsen |
| 4,227,522 A | 10/1980 | Carris |
| 4,627,432 A | 12/1986 | Newell et al. |
| 4,778,054 A | 10/1988 | Newell et al. |
| 4,811,731 A | 3/1989 | Newell et al. |
| 5,035,237 A | 7/1991 | Newell et al. |
| 5,352,461 A | 10/1994 | Feldstein et al. |
| 5,503,852 A | 4/1996 | Steiner et al. |
| 5,565,350 A | 10/1996 | Kmiec |
| 6,071,497 A | 6/2000 | Steiner et al. |
| 6,331,318 B1 | 12/2001 | Milstein |
| 6,428,771 B1 | 8/2002 | Steiner et al. |
| 6,440,463 B1 | 8/2002 | Feldstein et al. |
| 6,444,226 B1 | 9/2002 | Steiner et al. |
| 6,652,885 B2 | 11/2003 | Steiner et al. |
| 6,921,527 B2 | 7/2005 | Platz et al. |
| 7,799,344 B2 | 9/2010 | Oberg |
| 7,803,404 B2 | 9/2010 | Hokenson et al. |
| 8,536,303 B2 | 9/2013 | Panitch et al. |
| 8,741,849 B2 | 6/2014 | Panitch et al. |
| 9,034,815 B2 | 5/2015 | Panitch |
| 9,327,008 B2 | 5/2016 | Panitch et al. |
| 9,493,508 B2 | 11/2016 | Panitch et al. |
| 9,642,888 B2 | 5/2017 | Lander et al. |
| 2006/0039985 A1 | 2/2006 | Bennett et al. |
| 2006/0040953 A1 | 2/2006 | Leone-Bay et al. |
| 2006/0041133 A1 | 2/2006 | Stevenson et al. |
| 2006/0099269 A1 | 5/2006 | Cheatham et al. |
| 2007/0196503 A1 | 8/2007 | Wilson et al. |
| 2007/0281906 A1 | 12/2007 | Dalton et al. |
| 2011/0052658 A1 | 3/2011 | Panitch |

(Continued)

FOREIGN PATENT DOCUMENTS

| WO | 1991/016038 | 10/1991 |
| WO | 9322443 A1 | 11/1993 |

(Continued)

OTHER PUBLICATIONS

Molina, J. R. et al.,; "Non-Small Cell Lung Cancer: Epidemiology, Risk Factors, Treatment, and Survivorship"; Mayo Clin Proc. May 2008; 83(5): 584-594).
Ettinger, D. S. , et al; "Non-Small Cell Lung Cancer"; J Natl Compr Canc Netw 2010; 8: 740-801.
Navada, S., et al; "Temporal trends in small cell lung cancer: Analysis of the national Surveillance, Epidemiology, and End-Results (SEER) database"; J Clin Oncol. 2006; 24(18S) suppl: 384S.
Sher, T., et al; "Small Cell Lung Cancer"; Mayo Clin Proc. 2008; 83(3): 355-367.
Doll, R., et al; "Mortality in relation to smoking: 20 years' observations on male British doctors"; Br Med J 1976; 2: (1525-1536).
Wald, N.J., et al; "Does breathing other people's tobacco smoke cause lung cancer?"; Br Med J 1986; 293: 1217-1222).

(Continued)

*Primary Examiner* — Julie Ha
(74) *Attorney, Agent, or Firm* — McCarter & English LLP

(57) ABSTRACT

Pharmaceutical compositions, systems and methods for treating a non-small cell lung cancer (NSCLC) solid tumor comprising a population of tumor cells are described. In some aspects, administering a pharmaceutical composition comprising a therapeutic amount of a polypeptide having the amino acid sequence YARAAARQARAKALARQLGVAA (SEQ ID NO: 1) or functional equivalent thereof, and a pharmaceutically acceptable carrier, is effective to inhibit a kinase activity in the population of tumor cells and to reduce cancer cell proliferation, to reduce tumor size, to reduce tumor burden, to induce tumor cell death, to overcome tumor chemoresistance, to enhance tumor chemosensitivity, or a combination thereof.

24 Claims, 8 Drawing Sheets

(56) References Cited

U.S. PATENT DOCUMENTS

Figure 1:
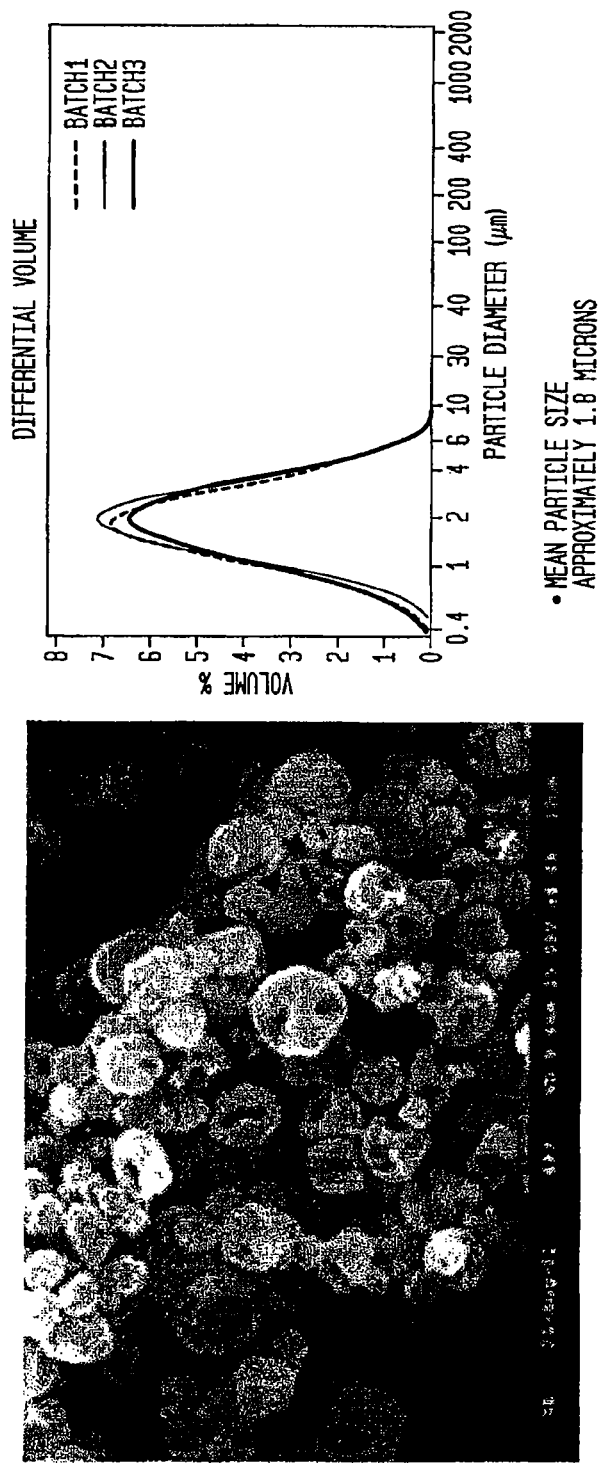
Figure 2:
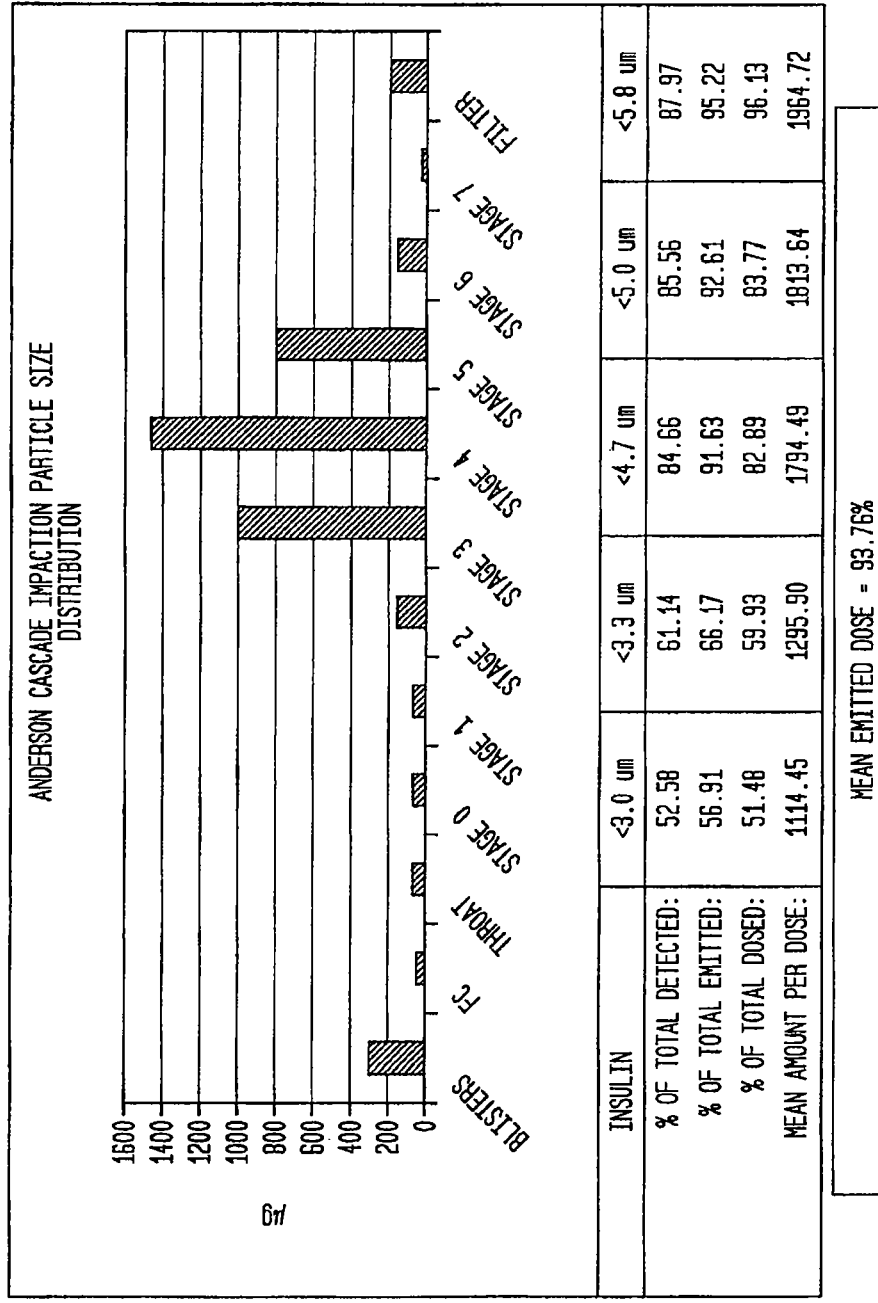
Figure 3:
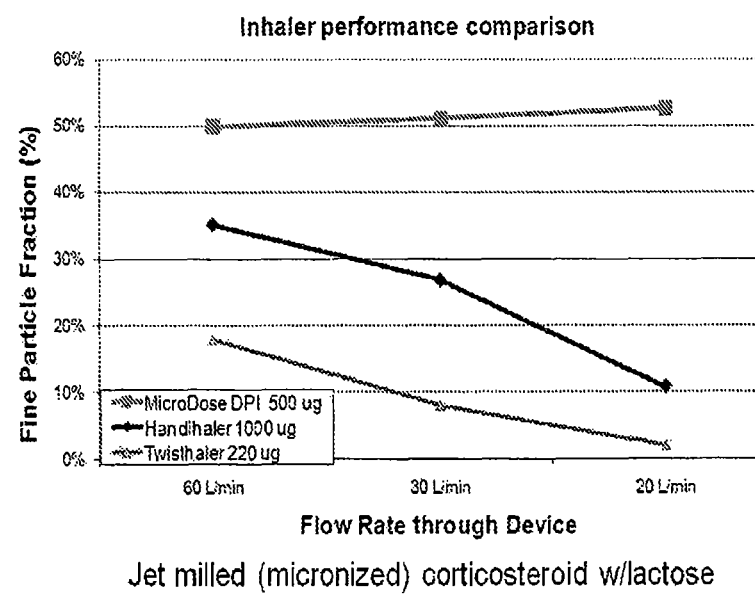
Figure 6:
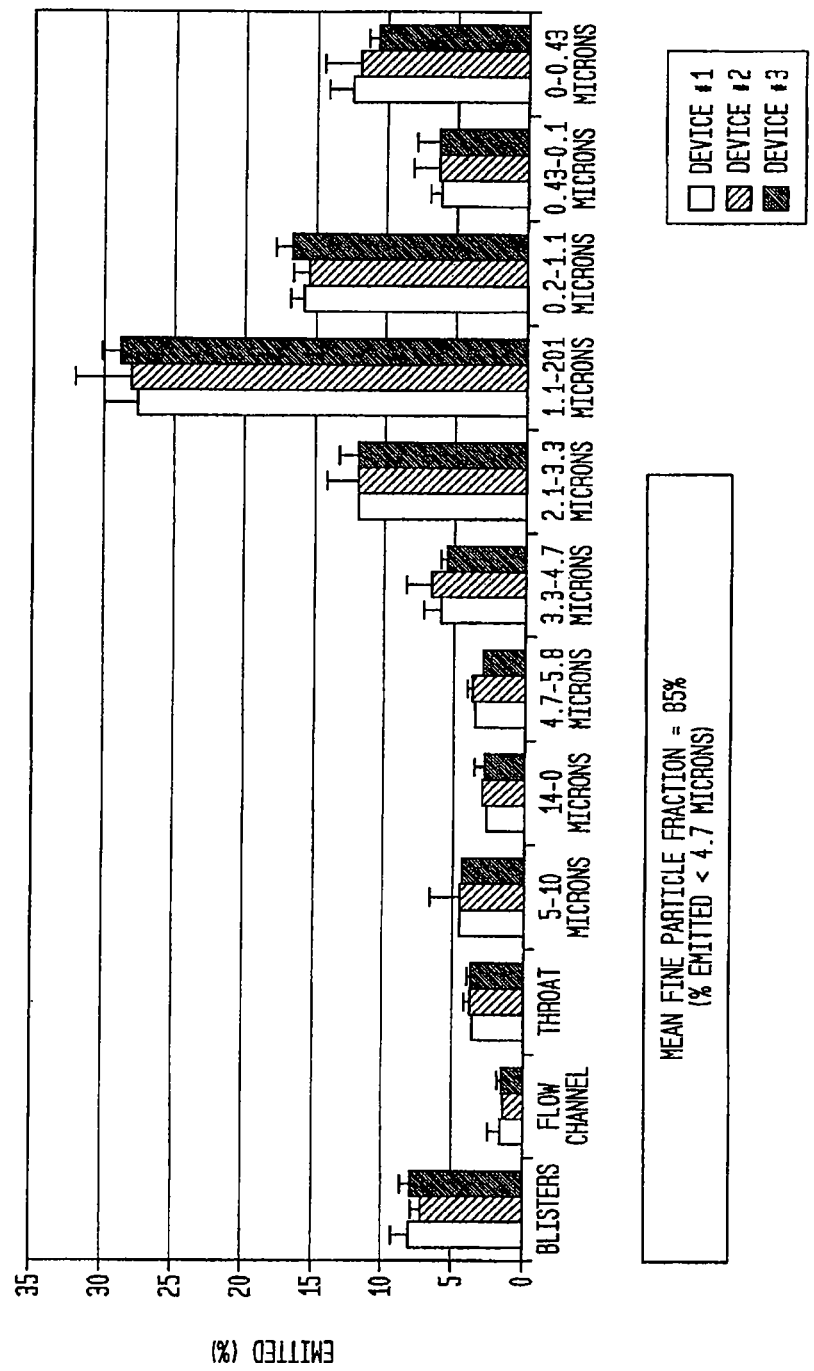

| | | | |
|---|---|---|---|
| 2011/0288036 A1 | 11/2011 | Lander | |
| 2013/0115256 A1 | 5/2013 | Lander et al. | |
| 2013/0184221 A9* | 7/2013 | Panitch | A61K 38/005 514/19.3 |
| 2013/0310424 A1* | 11/2013 | Surber | A61K 9/0078 514/345 |
| 2014/0072613 A1 | 3/2014 | Lander et al. | |

FOREIGN PATENT DOCUMENTS

| | | |
|---|---|---|
| WO | 2010/068692 A1 | 6/2010 |
| WO | 2013/182912 A2 | 12/2013 |

OTHER PUBLICATIONS

Omenn, G.S. et al; "Contribution of Environmental Fibers to Respiratory Cancer"; Environ Health Perspect 1986; 70: 51-56).

Fraumeni, J.F.; "Respiratory carcinogenesis: an epidemiologic appraisal"; J Natl Cancer Inst 1975; 55: 1039-1046.

Janerich, D. T., , et al"Lung Cancer and Exposure to Tobacco Smoke in the Household"; N Engl J Med 1990; 323: 632-636).

Hwang, S. J.et al; "Lung cancer risk in germline p53 mutation carriers: association between an inherited cancer predisposition, cigarette smoking, and cancer risr"; Hum Genet Aug. 2003; 113(3): 238-243.

Bailey-Wilson, J. E., et al: "A Major Lung Cancer Susceptibility Locus Maps to Chromosome 6q23-25"; Am J Human Genet. Sep. 2004; 75(3): 460-474.

Hung, R. J., et al; "A susceptibility locus for lung cancer maps to nicotinic acetylcholine receptor subunit genes on 15q25"; Nature. 2008; 452(7178): 633-637.

Li, X. and Hemminki, K.; "Inherited predisposition to early onset lung cancer according to histological type"; Int. J Cancer. 2004; 112(3): 451-457).

Thorgeirsson, T,. E., et al; "A Variant Associated with Nicotine Dependence, Lung Cancer and Peripheral Arterial Disease"; Nature. 2008; 452(7178): 638-642.

Kaneko, M., et al; "Peripheral lung cancer: screening and detection with low-dose spiral CT versus radiography"; Radiology 1996; 201: 798-802.

Swenson, S. J., et al; "Screening for Lung Cancer with Low-Dose Spiral Computed Tomography"; Am J Respir Crit Care Med 2002; 165: 508-513.

Henschke, C. I., et al; "CT Screening for Lung Cancer:Prevalence and Incidence of Mediastinal Masses"; Radiology 2006; 239(2): 586-590).

Read, C., et al; "Early Lung Cancer: screening and detection"; Primary Care Respiratory Journal (2006) 15, 332-336).

Thunnissen, F. B.; "Sputum examination for early detection of lung cancer"; J Clin Pathol 2003; 56: 805-810).

Marek, W., et al; "Can semi-automated image cytometry on induced sputum become a screening tool for lung caancer?"; Eur Respir J 2001; 18: 942-950.

Lam, S. et al; "Detection of dysplasia and carcinoma in situ with a lung imaging fluorescence endoscope device"; J Thorac Cardiovasc Surg 1993; 105:1035-1040.

Leonhard, M.; "New Incoherent Autofluorescence/Fluorescence System for Early Detection of Lung Cancer"; Diagn Therap Endosc 1999; 5: 71-75.

Lam, S., et al;"Localization of Bronchial Intraepithelial Neoplastic Lesions by Fluorescence Bronchoscopy"; Chest 1998; 113:696-702.

Vermylen, P., et al; "Detection of bronchial preneoplastic lesions and early lung cancer with fluorescence bronchoscopy: a study about its ambulatory feasibility under local anaesthesis"; Lung Cancer 1999; 25: 161.

Venmans, B. J., et al; "Results of Two Years Experience with Fluorescence Bronchoscopy in Detection of Preinvasive Bronchial Neoplasia"; Diagn Therap Endosc 1999; 5: 77-84.

Ikeda, N., et al; "Early Localization of Bronchogenic Cancerous/ Precancerous Lesions with Lung Imaging Fluorescence Endoscope"; Diagn Therap Endosc 1997; 3: 197-201.

Yokomise, H., et al; "Clinical Experience with Lung-Imaging Fluorescence Endoscope (LIFE) in Patients with Lung cancer"; J Bronchol 1997; 4: 205-208.

Hirsch, F. R., et al; "Fluorescence Versus White-Light Bronchoscopy for Detection of Preneoplastic Lesions: a Randomized Study"; J Natl Cancer Inst 2001; 93: 1385-1391.

Tsao, M. S., et al; "Erlotinib in Lung Cancer—Molecular and Clinical Predictors of Outcome"; N Engl J Med 2005; 353: 133-144).

Sequist, L. V., et al; "First-Line Gefitinib in Patients With Advanced Non-Small-Cell Lung Cancer Harboring Somatic EGFR Mutations"; J Clin Oncol 2008; 26: 2442-2449.

Miller, V. A.,; "Molecular Characteristics of Bronchioloalveolar Carcinoma and Adenocarcinoma, Bronchioloalveolar Carcinoma Subtype, Predict Response to Erlotinib"; J Clin Oncol 2008; 26: 1472-1478.

Simon, G.R., et al; "ERCC1 Expression Is a Predictor of Survival in Resected Patients With Non-small Cell Lung Cancer*"; Chest 2005; 127: 978-983.

Olaussen, K. A., et al; "DNA Repair by ERCC1 in Non-Small-Cell Lung Cancer and Cisplatin-Based Adjuvant Chemotherapy"; N Engl J Med 2006; 355: 983-991.

Bepler, G., et al; "RRM1 Modulated In Vitro and In Vivo Efficacy of Gemcitabine and Platinum in Non-Small-Cell Lung Cancer"; J Clin Oncol 2006; 24: 4731-4737.

Slebos, R. J., et al; "K-ras Oncogene Activation as a Prognostic Marker in Adenocarcinoma of the Lung"; N Engl J Med 1990; 323: 561-565.

Tsao, M. S., et al; "Prognostic and Predictive Importance of p53 and RAS for Adjuvant Chemotherapy in Non-Small-Cell Lung Cancer"; J Clin Oncol 2007; 25: 5240-5247.

Bepler, G., et al; "RRM1 and PTEN as Prognostic Parameters for Overall and Disease-Free Survival in Patients With Non-Small-Cell Lung Cancer"; J Clin Oncol 2004; 22: 1878-1885.

Zheng, Z., et al; "DNA Synthesis and Repair Genes RRM1 and ERCC1 in Lung Cancer"; N Engl J Med 2007; 356: 300-808.

Bepler, G., et al; "Predictive value of RRM1 and ERCC1 protein levels in a prospective community-based trial of gemcitabine/ carboplatin (GC) vs gemcitabine (G) alone"; J Clin Oncol 2008; 26(Suppl 1): Abstract 8033.

Reynolds, C., et al; "Randomized Phase III Trial of Gemcitabine-Based Chemotherapy With In Situ RRM1 and ERCC1 Protein Levels for Response Prediction in Non-Small-Cell Lung Cancer"; J Clin Oncol 2009; 27: 5808-5815).

Boffa, D. J., et al; "Data from the Society of Thoracic Surgeons General Thoracic Surgery database: The surgical management of primary lung tumore"; J Thorac Cardiovasc Surg 2008; 135: 247-254.

Scott, W. J.. et al; "Treatment of Non-small Cell Lung Cancer Stage I and Stage II*"; Chest 2007; 132: 234S-242S.

Xing, S., et al; "Predictive value of image cytometry fordiagnosis of lung cancer in heavy smokers"; Eur Respir J 2005; 25: 956-963.

Ginsberg, R. J., et al; "Randomized Trial of Lobectomy Versus Limited Resection for T1 NO Non-Small Cell Lung Cancer"; Ann Thorac Surg 1995; 60: 615-622.

Koike, T., et al; "Intentional limited pulmonary resection for peripheral T1 N0 M0 small-sized lung cancer"; J Thorac Cardiovasc Surg 2003; 125: 924-928.

Ohe, Y., et al; "Randomized phase III study of cisplatin plus irinotecan versus carboplatin plus paclitaxel, cisplatin plus gemcitabine, and cisplatin plus vinorelbine for advanced non-small-cell lung cancer. Four-Arm Cooperative Study in Japan"; Ann Oncol 2007; 18: 317-323.

Fossella, F., et al; "Randomized, Multinational, Phase III Study of Docetaxel Plus Platinum Combinations Versus Vinorelbine Plus Cisplatin for Advanced Non-Small-Cell Lung Cancer: The TAX 326 Study Group"; J Clin Oncol 2003; 21: 3016-3024.

Smit, E., et al; "Three-Arm Randomized Study of Two Cisplatin-Based Regimens and Paclitaxel Plus Gemcitabine in Advanced Non-Small-Cell Lung Cancer: A Phase III Trial of the European

(56) References Cited

OTHER PUBLICATIONS

Organization for Research and Treatment of Cancer Lung Cancer Group—EORTC 08975"; J Clin Oncol 2003; 21: 3909-3917.
Zatloukal, P., et al; "Concurrent versus sequential chemoradiotherapy with cisplatin and vinorelbine in locally advanced non-small cell lung cancer: a randomized study"; Lung Cancer 2004; 46: 87-98.
Scagliotti, G.V. et al; "Phase III Study Comparing Cisplatin Plus Gemcitabine With Cisplatin Plus Pemetrexed in Chemotherapy-Naive Patients With Advanced-Stage Non-Small-Cell Lung Cancer"; J Clin Oncol 2008; 26: 3543-3551.
Molina, J. R., et al; "Non-Small Cell Lung Cancer: Epidemiology, Risk Factors, Treatment, and Survivorship"; Mayo Clin Proc May 2008; 83(5): 584-594.
Sandler, A. B., et al; "Anti-Vascular Endothelial Growth Factor Monoclonals in Non-Small Cell Lung Cancer"; Clin Cancer Res 2004; 10: 4258s-4262s.
Giaccone, G., et al; "Epidermal Growth Factor Receptor Inhibitors in the Treatment of Non-Small-Cell Lung Cancer"; J Clin Oncol 2005; 23: 3235-3242.
Sandler, A., et al; "Paclitaxel—Carboplatin Alone or with Bevacizumab for Non-Small-Cell Lung Cancer"; N Engl J Med 2006; 355: 2542-2550.
Sequist, L. V., et al; "Response to Treatment and Survival of Patients with Non-Small Cell Lung Cancer Undergoing Somatic EGFR Mutation Testing"; Oncologist 2007; 12: 90-98.
Mok, T.S., et al; "Gefitinib or Carboplatin—Paclitaxel in Pulmonary Adenocarcinoma"; N Eng J Med 2009; 361: 947-957.
Inoue, A., et al; "First-Line Gefitinib for Patients With Advanced Non-Small-Cell Lung Cancer Harboring Epidermal Growth Factor Receptor Mutations Without Indication for Chemotherapy"; J Clin Oncol 2009; 27: 1394-1400.
Pirker, R., et al; "Cetuximab plus chemotherapy in patients with advanced non-small-cell lung cancer (FLEX): an open-label randomised phase III trial"; Lancet 2009; 373: 1525-1531.
Nguyen, K. S., et al; "Acquired Resistance to Epidermal Growth Factor Receptor Tyrosine Kinase Inhibitors in Non-Small-Cell Lung Cancers Dependent on the Epidermal Growth Factor Receptor Pathway"; Clin Lung Cancer 2009; 10: 281-289.
Gazdar, A. F.; "Activating and resistance mutations of EGFR in non-small-cell lung cancer: role in clinical response to EGFR tyrosine kinase inhibitors"; Oncogene 2009; 28(Suppl 1): S24-S31.
Morandell, S., et al; "A Reversible Gene-Targeting Strategy Identifies Synthetic Lethal Interactions between MK2 and p53 in the DNA Damage Response In Vivo"; Cell Reports 5, 868-877, Nov. 27, 2013.
Negrini, S., et al; "Genomic instability—an evolving hallmark of cancer"; Nat Rev Mol Cell Biol 2010; 11: 220-228.
Ciccia, A. and Elledge, S. J.; "The DNA Damage Response: Making It Safe to Play with Knives"; Mol Cell 2010; 40: 179-204.
Manke, I. A. et al; "MAPKAP Kinase-2 Is a Cell Cycle Checkpoint Kinase that Regulates the G2/M Transition and S Phase Progression in Response to UV Irradiation"; Mol Cell 2005; 17: 37-48.
Reinhardt, H.C., et al; "p53-Deficient CellsRelyonATM- andATR—Mediated Checkpoint Signaling through the p38MAPK/MK2 Pathway for Survival after DNA Damage"; Cancer Cell 2007; 11: 175-189.
Reinhardt, H.C., et al; "DNA Damage Activates a Spatially Distinct Late Cytoplasmic Cell-Cycle Checkpoint Network Controlled by MK2-Mediated RNA Stabilization"; Mol Cell 2010; 40: 34-49.
Keatings V., et al; "Differences in interleukin-8 and tumor necrosis factor-alpha in induced sputum from patients with chronic obstructive pulmonary disease or asthma"; Am J Resp Crit Care Med, 1996, 153:530-534.
Lim, S. et al; "Balance of Matrix Metalloprotease-9 and Tissue Inhibitor of Metalloprotease-1 from Alveolar Macrophages in Cigarette Smokers"; J Respir Crit Care Med, 2000, 162:1355-1360.
Parcellier, A., et al; "HSP27 Is a Ubiquitin-Binding Protein Involved in I-B Proteasomal Degradation"; Mol Cell Biol, 23(16): 5790-5802, 2003.

Bode, J., et al; "The macrophage response towards LPS and its control through the p38(MAPK)-STAT3 axis"; Cellular Signalling, 24: 1185-1194, 2012.
Ehlting, C. et al; "Distinct Functions of the Mitogen-activated Protein Kinase-activated Protein (MAPKAP) Kinases MK2 and MK3: MK2 Mediates Lipopolysaccharide-Induced Signal Transducers and Activators of Transcription 3 (STAT3) Activation by Preventing Negative Regulatory Effects of MK3*"; J. Biol. Chem., vol. 286, No. 27, pp. 24113-24124, Jul. 8, 2011.
Eldar-Finkelman, H., et a;; "Substrate Competitive GSK-3 Inhibitors \ strategy and Implications"; Biochim, Biophys. Acta, 1804(3):598-603, 2010).
Van Es, J., et al; "You Wnt some, you lose some: oncogenes in the Wnt signaling pathway"; Curr. Opin. Gent. Dev. 13:28-33, 2003).
Snyder, E. and Dowdy, S.; "Cell Penetrating Peptides in Drug Delivery"; Pharm Res., 21(3):389-393, 2004.
Beerens, A., et al; "Protein Transduction Domains and their Utility in Gene Therapy"; Curr Gene Ther., 3(5):486-494, 2003.
Payne, R. W. and Manning, M. C., "Peptide formulation: challenges and strategies," Innovations in Pharmaceutical Technology, 64-68 (2009).
Zhang, S. et al., "TrkB is highly expressed in NSCLC and mediates BDNF-induced activation of Pyk2 signaling and the invasion of A549 cells," BMC Cancer 2010,10: 43.
Loberg, RD, et al: "Enhanced Glycogen Synthase Kinase-3 Activity Mediates Hypoxia-induced Apoptosis of Vascular Smooth Muscle Cells and Is Prevented by Glucose Transport and Metabolism*"; J. Biol. Chem. 277 (44): 41667-673(2002).
Smith, T. F. and Waterman, M.S.; "Comparison of biosequences"; Adv. Appl. Math. 2:482 (1981).
Needleman, S. B. and Wunsch, C. D.; "A general method applicable to the search for similarities in the amino acid sequence of two proteins"; J. Mol. Biol. 48:443 (1970).
Pearson, WR and Lipman, DJ; "Improved tools for biological sequence comparison"; Proc. Natl. Acad. Sci. 85:2444 (1988).
Higgins, D. G. and Sharp, P. M.; "CLUSTAL: A package for performing multiple sequence alignment on a microcomputer"; Gene 73:237-244 (1988).
Corpet, F., et al; "Multiple sequence alignment with hierarchical clustering"; Nucleic Acids Research 16:10881-90 (1988).
Huang, et al; Parallelization of a local similarity algorithm: ; Computer Applications in the Biosciences, 8:155-65 (1992).
Pearson, W.R., et al; "Using the FASTA Program to Search Protein and DNA Sequence Databases"; Methods in Molecular Biology, 24:307-331 (1994).
Higgins, D. G. and Sharp, P. M., ; Fast and sensitive multiple sequence alignments on a microcomputer; CABIOS, 5:151-153 (1989).
Altschul, et al; Gapped BLAST and PSI-BLAST: a new generation of protein database search programs; Nucleic Acids Res. 25:3389-3402 (1997).
Henikoff, S. and Henikoff, J.; "Amino acid substitution matrices from protein blocks"; Proc. Natl. Acad. Sci. USA 89:10915, 1992.
Karlin & Altschul; "Applications and statistics for multiple high-scoring segments in molecular sequences"; Proc. Natl. Acad. Sci. USA, vol. 90, pp. 5873-5877, Jun. 1993.
Wooten, J. and Federhen, S.; "Statistics of Local Complexity in Amino Acid Sequences and Sequence Databases"; Comput. Chem., 17:149-163 (1993).
Claverie and States; "Information Enhancement Methods for Large Scale Sequence Analysis"; Comput. Chem., 17:191-201 (1993).
Meyers and Miller; "Optimal alignments in linear space"; Computer Applic. Biol. Sci., 4:11-17 (1988).
Merrifield, R. B.; "Solid Phase Peptide Synthesis. I. The Synthesis of a Tetrapeptide"; 1963, J. Am. Chem. Soc. 85:2149-2154.
Carpino, L and Han, G.; "The 9-Fluorenylmethoxycarbonyl Amino-Protecting Group"; J . Org. Chem., vol. 37, No. 62, 3404-3409; 1976.
Fields and Noble; "Solid phase peptide synthesis utilizing 9-fluorenylmethoxycarbonyl amino acids"; Int. J. Pept. Protein Res. 35:161-214, 1990.

\* cited by examiner

NEAT SPRAY DRIED INSULIN

FIG. 4

FLOW-RATE INDEPENDENCE

FINE PARTICLE DOSE

FLOW RATE (l/min)

☐ FPD < 4.7 μm

▨ FPD < 3.3 μm

*SPRAY-DRIED NEAT PEPTIDE 250 mcg*

FIGURE 5

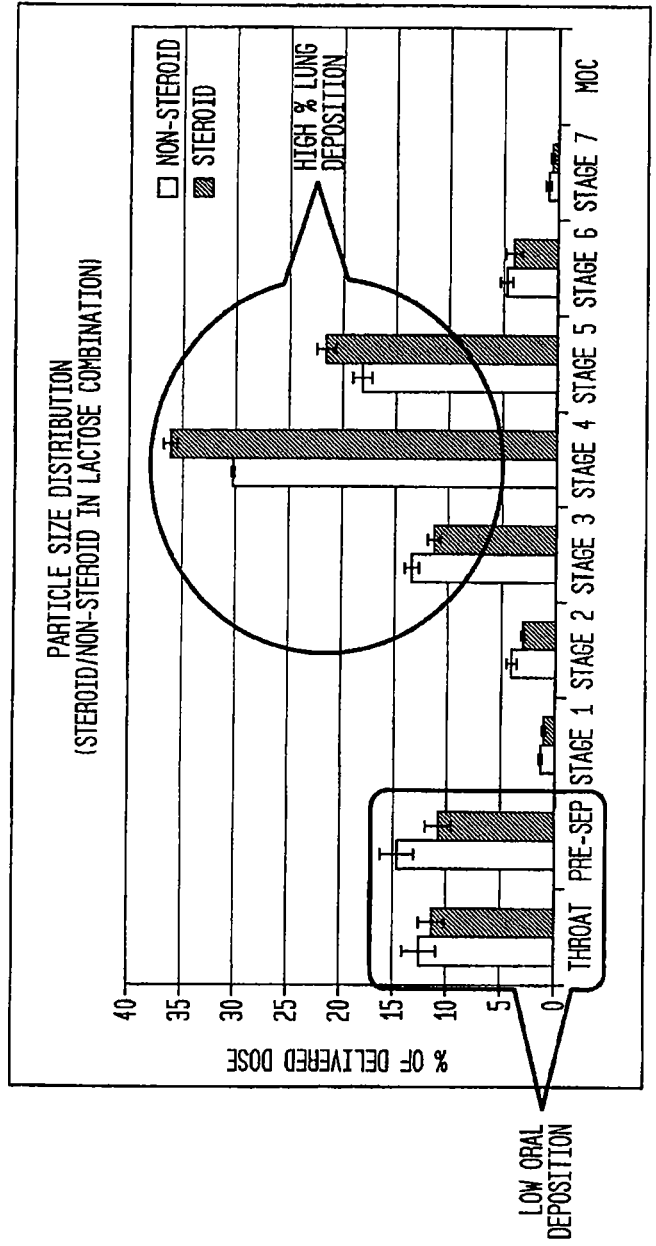

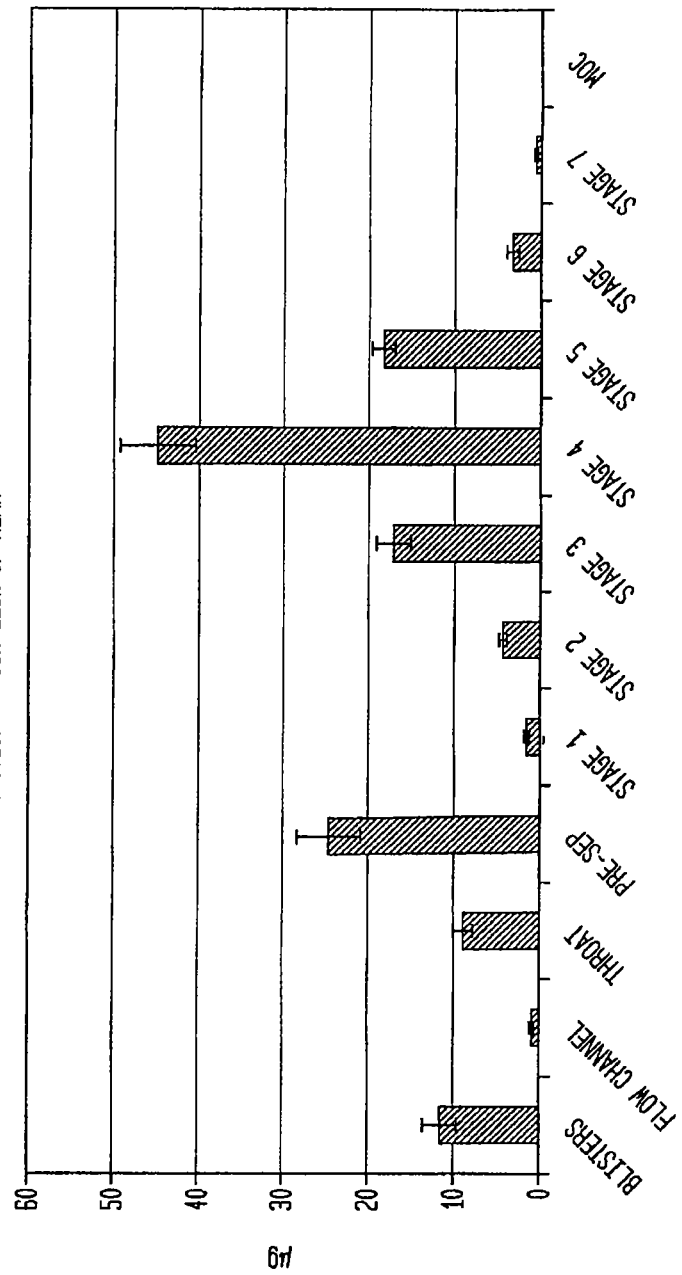

SEQUENCE LISTING

<160> NUMBER OF SEQ ID NOS: 24

<210> SEQ ID NO 1
<211> LENGTH: 22
<212> TYPE: PRT
<213> ORGANISM: Unknown
<220> FEATURE:
<223> OTHER INFORMATION: Mammalian

<400> SEQUENCE: 1

Tyr Ala Arg Ala Ala Ala Arg Gln Ala Arg Ala Lys Ala Leu Ala Arg
 1               5                  10                  15

Gln Leu Gly Val Ala Ala
            20

-continued

```
<210> SEQ ID NO 2
<211> LENGTH: 11
<212> TYPE: PRT
<213> ORGANISM: Unknown
<220> FEATURE:
<223> OTHER INFORMATION: Mammalian

<400> SEQUENCE: 2

Lys Ala Leu Ala Arg Gln Leu Gly Val Ala Ala
1               5                   10

<210> SEQ ID NO 3
<211> LENGTH: 21
<212> TYPE: PRT
<213> ORGANISM: Unknown
<220> FEATURE:
<223> OTHER INFORMATION: Mammalian

<400> SEQUENCE: 3

Phe Ala Lys Leu Ala Ala Arg Leu Tyr Arg Lys Ala Leu Ala Arg Gln
1               5                   10                  15

Leu Gly Val Ala Ala
            20

<210> SEQ ID NO 4
<211> LENGTH: 23
<212> TYPE: PRT
<213> ORGANISM: Unknown
<220> FEATURE:
<223> OTHER INFORMATION: Mammalian

<400> SEQUENCE: 4

Lys Ala Phe Ala Lys Leu Ala Ala Arg Leu Tyr Arg Lys Ala Leu Ala
1               5                   10                  15

Arg Gln Leu Gly Val Ala Ala
            20

<210> SEQ ID NO 5
<211> LENGTH: 21
<212> TYPE: PRT
<213> ORGANISM: Unknown
<220> FEATURE:
<223> OTHER INFORMATION: Mammalian

<400> SEQUENCE: 5

Tyr Ala Arg Ala Ala Ala Arg Gln Ala Arg Ala Lys Ala Leu Ala Arg
1               5                   10                  15

Gln Leu Ala Val Ala
            20

<210> SEQ ID NO 6
<211> LENGTH: 21
<212> TYPE: PRT
<213> ORGANISM: Unknown
<220> FEATURE:
<223> OTHER INFORMATION: Mammalian

<400> SEQUENCE: 6

Tyr Ala Arg Ala Ala Ala Arg Gln Ala Arg Ala Lys Ala Leu Ala Arg
1               5                   10                  15

Gln Leu Gly Val Ala
            20

<210> SEQ ID NO 7
<211> LENGTH: 22
```

```
<212> TYPE: PRT
<213> ORGANISM: Unknown
<220> FEATURE:
<223> OTHER INFORMATION: Mammalian

<400> SEQUENCE: 7

His Arg Arg Ile Lys Ala Trp Leu Lys Lys Ile Lys Ala Leu Ala Arg
1               5                   10                  15

Gln Leu Gly Val Ala Ala
            20

<210> SEQ ID NO 8
<211> LENGTH: 10
<212> TYPE: PRT
<213> ORGANISM: Unknown
<220> FEATURE:
<223> OTHER INFORMATION: Mammalian

<400> SEQUENCE: 8

Lys Ala Leu Ala Arg Gln Leu Ala Val Ala
1               5                   10

<210> SEQ ID NO 9
<211> LENGTH: 10
<212> TYPE: PRT
<213> ORGANISM: Unknown
<220> FEATURE:
<223> OTHER INFORMATION: Mammalian

<400> SEQUENCE: 9

Lys Ala Leu Ala Arg Gln Leu Gly Val Ala
1               5                   10

<210> SEQ ID NO 10
<211> LENGTH: 11
<212> TYPE: PRT
<213> ORGANISM: Unknown
<220> FEATURE:
<223> OTHER INFORMATION: Mammalian

<400> SEQUENCE: 10

Lys Ala Leu Ala Arg Gln Leu Gly Val Ala Ala
1               5                   10

<210> SEQ ID NO 11
<211> LENGTH: 11
<212> TYPE: PRT
<213> ORGANISM: Unknown
<220> FEATURE:
<223> OTHER INFORMATION: Mammalian

<400> SEQUENCE: 11

Tyr Ala Arg Ala Ala Ala Arg Gln Ala Arg Ala
1               5                   10

<210> SEQ ID NO 12
<211> LENGTH: 14
<212> TYPE: PRT
<213> ORGANISM: Unknown
<220> FEATURE:
<223> OTHER INFORMATION: Mammalian

<400> SEQUENCE: 12

Trp Leu Arg Arg Ile Lys Ala Trp Leu Arg Arg Ile Lys Ala
1               5                   10
```

<210> SEQ ID NO 13
<211> LENGTH: 7
<212> TYPE: PRT
<213> ORGANISM: Unknown
<220> FEATURE:
<223> OTHER INFORMATION: Mammalian

<400> SEQUENCE: 13

Trp Leu Arg Arg Ile Lys Ala
1               5

<210> SEQ ID NO 14
<211> LENGTH: 11
<212> TYPE: PRT
<213> ORGANISM: Unknown
<220> FEATURE:
<223> OTHER INFORMATION: Mammalian

<400> SEQUENCE: 14

Tyr Gly Arg Lys Lys Arg Arg Gln Arg Arg Arg
1               5                   10

<210> SEQ ID NO 15
<211> LENGTH: 12
<212> TYPE: PRT
<213> ORGANISM: Unknown
<220> FEATURE:
<223> OTHER INFORMATION: Mammalian

<400> SEQUENCE: 15

Trp Leu Arg Arg Ile Lys Ala Trp Leu Arg Arg Ile
1               5                   10

<210> SEQ ID NO 16
<211> LENGTH: 10
<212> TYPE: PRT
<213> ORGANISM: Unknown
<220> FEATURE:
<223> OTHER INFORMATION: Mammalian

<400> SEQUENCE: 16

Phe Ala Lys Leu Ala Ala Arg Leu Tyr Arg
1               5                   10

<210> SEQ ID NO 17
<211> LENGTH: 12
<212> TYPE: PRT
<213> ORGANISM: Unknown
<220> FEATURE:
<223> OTHER INFORMATION: Mammalian

<400> SEQUENCE: 17

Lys Ala Phe Ala Lys Leu Ala Ala Arg Leu Tyr Arg
1               5                   10

<210> SEQ ID NO 18
<211> LENGTH: 11
<212> TYPE: PRT
<213> ORGANISM: Unknown
<220> FEATURE:
<223> OTHER INFORMATION: Mammalian

<400> SEQUENCE: 18

His Arg Arg Ile Lys Ala Trp Leu Lys Lys Ile
1               5                   10

<210> SEQ ID NO 19

```
<211> LENGTH: 21
<212> TYPE: PRT
<213> ORGANISM: Unknown
<220> FEATURE:
<223> OTHER INFORMATION: Mammalian

<400> SEQUENCE: 19

Tyr Ala Arg Ala Ala Ala Arg Gln Ala Arg Ala Lys Ala Leu Asn Arg
 1               5                  10                  15

Gln Leu Gly Val Ala
             20

<210> SEQ ID NO 20
<211> LENGTH: 9
<212> TYPE: PRT
<213> ORGANISM: Unknown
<220> FEATURE:
<223> OTHER INFORMATION: Mammalian

<400> SEQUENCE: 20

Arg Lys Lys Arg Arg Gln Arg Arg Arg
 1               5

<210> SEQ ID NO 21
<211> LENGTH: 10
<212> TYPE: PRT
<213> ORGANISM: Unknown
<220> FEATURE:
<223> OTHER INFORMATION: Mammalian

<400> SEQUENCE: 21

Lys Lys Leu Asn Arg Thr Leu Ser Val Ala
 1               5                  10

<210> SEQ ID NO 22
<211> LENGTH: 13
<212> TYPE: PRT
<213> ORGANISM: Unknown
<220> FEATURE:
<223> OTHER INFORMATION: Mammalian

<400> SEQUENCE: 22

Lys Lys Lys Ala Leu Asn Arg Gln Leu Gly Val Ala Ala
 1               5                  10

<210> SEQ ID NO 23
<211> LENGTH: 22
<212> TYPE: PRT
<213> ORGANISM: Unknown
<220> FEATURE:
<223> OTHER INFORMATION: Mammalian

<400> SEQUENCE: 23

Tyr Ala Arg Ala Ala Ala Arg Asp Ala Arg Ala Lys Ala Leu Asn Arg
 1               5                  10                  15

Gln Leu Ala Val Ala Ala
             20

<210> SEQ ID NO 24
<211> LENGTH: 21
<212> TYPE: PRT
<213> ORGANISM: Unknown
<220> FEATURE:
<223> OTHER INFORMATION: Mammalian

<400> SEQUENCE: 24
```

-continued

```
Tyr Ala Arg Ala Ala Ala Arg Gln Ala Arg Ala Lys Ala Leu Asn Arg
1               5                   10                  15

Gln Leu Ala Val Ala
            20
```

USE OF MKS INHIBITOR PEPTIDE-CONTAINING COMPOSITIONS FOR TREATING NON-SMALL CELL LUNG CANCER WITH SAME

CROSS-REFERENCE TO RELATED APPLICATION

This application claims the benefit of priority to U.S. Provisional Application No. 62/132,374, filed Mar. 12, 2015, the content of which is incorporated by reference herein in its entirety.

FIELD OF THE INVENTION

The invention is in the fields of cell and molecular biology, polypeptides, and therapeutic methods of use.

BACKGROUND

Non-Small Cell Lung Cancer (NSCLC)

Lung cancer has become the number one killer among cancers worldwide (Molina, J. R. et al., Mayo Clin Proc. 2008 May; 83(5): 584-594). Only 15% of all lung cancer patients are alive five (5) years or more after diagnosis (Ettinger, D. S. et al., J Natl Compr Canc Netw 2010; 8: 740-801). The two (2) main types of lung cancer are small cell lung cancer (SCLC) and non-small cell lung cancer (NSCLC), the latter of which accounts for approximately 85% of all cases of lung cancer (Molina, J. R. et al., Mayo Clin Proc. 2008 May; 83(5): 584-594; Navada, S. et al., J Clin Oncol. 2006; 24(18S) suppl: 384S; Sher, T. et al., Mayo Clin Proc. 2008; 83(3): 355-367).

Risk Factors for NSCLC

The primary risk factor for lung cancer is smoking, which accounts for more than 85% of all lung cancer-related deaths (Ettinger, D. S. et al., J Natl Compr Canc Netw 2010; 8: 740-801; Doll, R. et al., Br Med J 1976; 2: 1525-1536). The risk for lung cancer increases with the number of cigarettes smoked per day and the number of years spent smoking. In addition to the hazard of first-hand smoke, exposed non-smokers have an increased relative risk for developing lung cancer (Ettinger, D. S. et al., J Natl Compr Canc Netw 2010; 8: 740-801; Wald N. J. et al., Br Med J 1986; 293: 1217-1222). Radon gas, a radioactive gas that is produced by the decay of radium 226, is the second leading cause of lung cancer. The decay of this isotope leads to the production of substances that emit alpha-particles, which may cause cell damage and therefore increase the potential for malignant transformation (Ettinger, D. S. et al., J Natl Compr Canc Netw 2010; 8: 740-801; Schrump, D. S. et al., *DeVita, Hellman, and Rosenberg's Cancer: Principles & Practice of Oncology*, 8th Edition. Vol. 1. Philadelphia: Lippincott Williams & Wilkins; 2008:896-946).

Asbestos, a mineral compound that breaks into small airborne shards, is a known carcinogen that increases the risk for lung cancer in people exposed to the airborne fibers, especially those who smoke (Ettinger, D. S. et al., J Natl Compr Canc Netw 2010; 8: 740-801). An estimated 3% to 4% of lung cancers are caused by asbestos exposure (Omenn, G. S. et al., Environ Health Perspect 1986; 70: 51-56). Other possible risk factors include recurring lung inflammation, lung scarring secondary to tuberculosis, family history, and exposure to other carcinogens, such as bis(chloromethyl) ether, polycyclic aromatic hydrocarbons, chromium, nickel, and organic arsenic compounds (Frau- meni, J. F., J Natl Cancer Inst 1975; 55: 1039-1046; Janerich D. T. et al., N Engl J Med 1990; 323: 632-636).

Familial clustering or aggregation of lung cancer has been reported in the past 60 years, suggesting a hereditary base to disease development (Ettinger, D. S. et al., J Natl Compr Canc Netw 2010; 8: 740-801; Sellers, T. A. and Yang P., King R A, Rotter J I, Motulsky A G, editors. The Genetic Basis of Common Diseases. 2nd ed. New York, N.Y.: Oxford University Press; 2002. pp. 700-712; Hwang, S. J. et al., Hum Genet. 2003 August; 113(3): 238-243; Bailey-Wilson, J. E. et al., Am J Human Genet. 2004 September; 75(3): 460-474; Hung, R. J. et al., Nature. 2008; 452(7178): 633-637). An increased risk of lung cancer was found in carriers of tumor protein p53 (TP53) germline sequence variations (Hwang, S. J. et al., Hum Genet. 2003 August; 113(3): 238-243). A germline epidermal growth factor receptor (EGFR) T790M sequence variation was reported in a family with multiple cases of NSCLC (Lie, X. and Hemminki, K., Int J Cancer. 2004; 112(3): 451-457). A genome-wide linkage study of 52 extended families identified a major susceptibility locus influencing lung cancer risk at 6q23-25p (Bailey-Wilson, J. E. et al., Am J Human Genet. 2004 September; 75(3): 460-474).

Three (3) independent genetic studies have found a marker on chromosome 15 associated with lung cancer (Ettinger, D. S. et al., J Natl Compr Canc Netw 2010; 8: 740-801). In all three (3) studies, the risk was approximately 30% higher for people with 1 copy of the marker and 70-80% higher for people with two (2) copies. The region where the marker resides contains 3 genes coding for subunits of the nicotinic acetylcholine receptor, a protein on the cell surface onto which nicotine molecules latch, triggering cell change (Ettinger, D. S. et al., J Natl Compr Canc Netw 2010; 8: 740-801; Thorgeirsson, T. E. et al., Nature. 2008; 452(7178): 638-642; Hung, R. J. et al., Nature. 2008; 452(7187): 633-637).

Staging of NSCLC

There are five stages (Stage 0 to Stage IV) in NSCLC. Stages I, II and III are further subdivided into A and B subtypes. These stages are assigned based on a Tumor, Node and Metastasis (TMN) staging system (See, cancer staging guidelines, www.NCCN.org). The TMN staging system of NSCLC is summarized in Table 1.

TABLE 1

Stages 0 to IV of NSCLC

| Stage | TMN (Tumor, Nodes, Metastasis) | Definition |
| --- | --- | --- |
| Occult carcinoma | TX, N0, M0 | TX = Primary tumor cannot be assessed, or tumor proven by the presence of malignant cells in sputum or bronchial washings but not visualized by imaging or bronchoscopy. N0 = No regional lymph node metastasis. M0 = No distant metastasis. |
| 0 | Tis, N0, M0 | Tis = Carcinoma in situ. N0 = No regional lymph node metastasis. M0 = No distant metastasis. |
| IA | T1a, N0, M0 T1b, N0, M0 | T1a = Tumor = 2 cm in greatest dimension. T1b = Tumor > 2 cm but = 3 cm in greatest dimension. N0 = No regional lymph node metastasis. M0 = No distant metastasis. |

TABLE 1-continued

Stages 0 to IV of NSCLC

| Stage | TMN (Tumor, Nodes, Metastasis) | Definition |
|---|---|---|
| IB | T2a, N0, M0 | T2a = Tumor > 3 cm but = 5 cm in greatest dimension.<br>N0 = No regional lymph node metastasis.<br>M0 = No distant metastasis. |
| IIA | T1a, N1, M0<br>T1b, N1, M0<br>T2a, N1, M0<br>T2b, N0, M0 | T1a = Tumor = 2 cm in greatest dimension.<br>T1b = Tumor > 2 cm but = 3 cm in greatest dimension.<br>T2a = Tumor > 3 cm but = 5 cm in greatest dimension.<br>T2b = Tumor > 5 cm but = 7 cm in greatest dimension.<br>N0 = No regional lymph node metastasis.<br>N1 = Metastasis in ipsilateral peribronchial and/or ipsilateral hilar lymph nodes and intrapulmonary nodes, including involvement by direct extension.<br>M0 = No distant metastasis. |
| IIB | T2b, N1, M0<br>T3, N0, M0 | T2b = Tumor > 5 cm but = 7 cm in greatest dimension.<br>T3 = Tumor > 7 cm or one that directly invades any of the following: parietal pleural (PL3) chest wall (including superior sulcus tumors), diaphragm, phrenic nerve, mediastinal pleura or parietal pericardium.<br>Tumor in the main bronchus (<2 cm distal to the carina, but without involvement of the carina.<br>Associated atelectasis or obstructive pneumonitis of the entire lung or separate tumor nodule(s) in the same lobe.<br>N0 = No regional lymph node metastasis.<br>N1 = Metastasis in ipsilateral peribronchial and/or ipsilateral hilar lymph nodes and intrapulmonary nodes, including involvement by direct extension.<br>M0 = No distant metastasis. |
| IIIA | T1a, N2, M0<br>T1b, N2, M0<br>T2a, N2, M0<br>T2b, N2, M0<br>T3, N1, M0<br>T3, N2, M0<br>T4, N0, M0<br>T4, N1, M0 | T1a = Tumor = 2 cm in greatest dimension.<br>T1b = Tumor > 2 cm but = 3 cm in greatest dimension.<br>T2a = Tumor > 3 cm but = 5 cm in greatest dimension.<br>T2b = Tumor > 5 cm but = 7 cm in greatest dimension.<br>T3 = Tumor > 7 cm or one that directly invades any of the following: parietal pleural (PL3) chest wall (including superior sulcus tumors), diaphragm, phrenic nerve, mediastinal pleura or parietal pericardium.<br>Tumor in the main bronchus (<2 cm distal to the carina but without involvement of the carina).<br>Associated atelectasis or obstructive pneumonitis of the entire lung or separate tumor nodule(s) in the same lobe.<br>T4 = Tumor of any size that invades any of the following: mediastinum, heart, great vessels, trachea, recurrent laryngeal nerve, esophagus, vertebral body, carina or separate tumor nodule(s) in a different ipsilateral lobe.<br>N0 = No regional lymph node metastasis.<br>N1 = Metastasis in ipsilateral peribronchial and/or ipsilateral hilar lymph nodes and intrapulmonary nodes, including involvement by direct extension.<br>N2 = Metastasis in ipsilateral mediastinal and/or subcarinal lymph node(s).<br>M0 = No distant metastasis. |
| IIIB | T1a, N3, M0<br>T1b, N3, M0<br>T2a, N3, M0<br>T2b, N3, M0<br>T3, N3, M0<br>T4, N2, M0<br>T4, N3, M0 | T1a = Tumor = 2 cm in greatest dimension.<br>T1b = Tumor > 2 cm but = 3 cm in greatest dimension.<br>T2a = Tumor > 3 cm but = 5 cm in greatest dimension.<br>T2b = Tumor > 5 cm but = 7 cm in greatest dimension.<br>T3 = Tumor > 7 cm or one that directly invades any of the following: parietal pleural (PL3) chest wall (including superior sulcus tumors), diaphragm, phrenic nerve, mediastinal pleura or parietal pericardium.<br>Tumor in the main bronchus (<2 cm distal to the carina but without involvement of the carina).<br>Associated atelectasis or obstructive pneumonitis of the entire lung or separate tumor nodule(s) in the same lobe.<br>T4 = Tumor of any size that invades any of the following: mediastinum, heart, great vessels, trachea, recurrent laryngeal nerve, esophagus, vertebral body, carina or separate tumor nodule(s) in a different ipsilateral lobe.<br>N2 = Metastasis in ipsilateral mediastinal and/or subcarinal lymph node(s).<br>N3 = Metastasis in contralateral mediastinal, contralateral hilar, ipsilateral or contralateral scalene or supraclavicular lymph node(s).<br>M0 = No distant metastasis. |
| IV | Any T, any N, M1A<br>Any T, any N, M1b | TX = Primary tumor cannot be assessed, or tumor proven by the presence of malignant cells in sputum or bronchial washings but not visualized by imaging or bronchoscopy.<br>T0 = No evidence of primary tumor.<br>Tis = Carcinoma in situ.<br>T1 = Tumor = 3 cm in greatest dimension, surrounded by lung or visceral pleura, without bronchoscopic evidence of invasion more proximal than the lobar |

TABLE 1-continued

Stages 0 to IV of NSCLC

| Stage | TMN (Tumor, Nodes, Metastasis) | Definition |
|---|---|---|
| | | bronchus (i.e., not in the main bronchus). |
| | | T1a = Tumor = 2 cm in greatest dimension. |
| | | T1b = Tumor > 2 cm but = 3 cm in greatest dimension. |
| | | T2 = Tumor > 3 cm but = 7 cm or tumor with any of the following features (T2 tumors with these features are classified T2a if = 5 cm): involves main bronchus, = 2 distal to the carina, invades visceral pleura (PL1 or PL2) or is associated with atelectasis or obstructive pneumonitis that extends to the hilar region but does not involve the entire lung. |
| | | T2a = Tumor > 3 cm but = 5 cm in greatest dimension. |
| | | T2b = Tumor > 5 cm but = 7 cm in greatest dimension. |
| | | T3 = Tumor > 7 cm or one that directly invades any of the following: parietal pleura (PL3) chest wall (including superior sulcus tumors), diaphragm, phrenic nerve, mediastinal pleura or parietal pericardium. Tumor in the main bronchus (<2 cm distal to the carina but without involvement of the carina). Associated atelectasis or obstructive pneumonitis of the entire lung or separate tumor nodule(s) in the same lobe. |
| | | T4 = Tumor of any size that invades any of the following: mediastinum, heart, great vessels, trachea, recurrent laryngeal nerve, esophagus, vertebral body, carina or separate tumor nodule(s) in a different ipsilateral lobe. |
| | | NX = Regional lymph nodes cannot be assessed. |
| | | N0 = No regional lymph node metastasis. |
| | | N1 = Metastasis in ipsilateral peribronchial and/or ipsilateral hilar lymph nodes and intrapulmonary nodes, including involvement by direct extension. |
| | | N2 = Metastasis in ipsilateral mediastinal and/or subcarinal lymph node(s). |
| | | N3 = Metastasis in contralateral mediastinal, contralateral hilar, ipsilateral or contralateral scalene or supraclavicular lymph node(s). |
| | | M0 = No distant metastasis. |
| | | M1 = Distant metastasis. |
| | | M1a = Separate tumor nodule(s) in a contralateral lobe tumor with pleural nodules or malignant pleural (or pericardial) effusion. |
| | | M1b = Distant metastasis. |

Screening for NSCLC

Computed Tomography (CT)

Computed tomography (CT) enables small lesions (in the region of 3 cm) to be detected (Read, C. et al., Primary Care Respiratory Journal (2006) 15, 332-336). Until recently, the slow scanning times and high radiation exposure of CT made it an unsuitable tool for screening. However, with the development and refinement of spiral CT, it has become possible to significantly reduce scanning times and radiation exposure. Results of CT screening have been encouraging, with approximately 80-90% of CT screen-detected bronchial carcinomasdiagnosed as early stage 1 tumors (Kaneko, M. et al., Radiology 1996; 201: 798-802; Swensen, S. J. et al., Am J Respir Crit Care Med 2002; 165: 508-513; Henschke, C. I. et al., Radiology 2006; 239(2): 586-590).

Sputum Cytometry

The diagnostic yield of sputum cytology is known to vary in relation to tumor location (Read, C. et al., Primary Care Respiratory Journal (2006) 15, 332-336). It has greatest use in the identification of central tumors and is of little or no value in the identification of peripheral cancers (Thunnissen F. B. J. M., J Clin Pathol 2003; 56: 805-810). However, it has been suggested that its sensitivity can be improved through the use of molecular genetic and immunocytochemical markers of malignancy (Marek, W. et al., Eur Respir J 2001; 18: 942-950; Xing, S. et al., Eur Respir J 2005; 25: 956-963).

Autofluorescence Bronchoscopy

Autofluorescence bronchoscopy has a high sensitivity for detection of abnormal cells (Read, C. et al., Primary Care Respiratory Journal (2006) 15, 332-336). This technique exploits the differences in the fluorescence properties of bronchial mucosa compared to mucosa of pre-invasive and invasive disease.

The best known instrument for autofluorescence bronchoscopy is the Lung Imaging Fluorescence Endoscopy (LIFE) system (Lam, S. et al., J Thorac Cardiovasc Surg 1993; 105: 1035-1040). This instrument uses a blue (442 nm) helium cadmium laser to illuminate bronchial mucosa, and the resulting fluorescence is then digitized into a real-time video image. Other devices, such as the D-light autofluorescence system, do not require image-intensifying cameras, but use optical filters incorporated into the bronchoscope (Leonhard, M., Diagn Therap Endosc 1999; 5: 71-75).

The majority of published studies on autofluorescence bronchoscopy have shown a significant increase in diagnostic sensitivity for dysplasia and carcinoma in situ detection (Read, C. et al., Primary Care Respiratory Journal (2006) 15, 332-3; Lam, S. et al., Chest 1998; 113: 696-702; Vermylen, P. et al., Lung Cancer 1999; 25: 161-168; Venmans B. J. et al., Diagn Therap Endosc 1999; 5: 77-84; Ikeda, N. et al., Diagn Therap Endosc 1997; 3: 197-201; Yokomise, H. et al., J Bronchol 1997; 4: 205-208; Hirsch, F. R. et al., J Natl Cancer Inst 2001; 93: 1385-1391).

Biomarkers

Several biomarkers have emerged as prognostic and predictive markers for NSCLC (Ettinger, D. S. et al., J Natl Compr Canc Netw 2010; 8: 740-801). A prognostic biomarker, which is an indicator of innate tumor aggressiveness, is a biomolecule that indicates patient survival independent of the treatment received. A predictive biomarker is a biomolecule that indicates therapeutic efficacy, i.e., an interaction exists between the biomolecule and therapy that impacts patient outcome. Among these biomarkers, evidence is strongest for EGFR, the 5' endonuclease of the nucleotide excision repair complex (ERCC1), Kirsten rat sarcoma viral oncogene homolog (K-ras), and the regulatory subunit of ribonucleotide reductase (RRM1).

The presence of the epidermal growth factor receptor (EGFR) exon 19 deletion or exon 21 L858R mutation does not seem to be prognostic of survival for patients with NSCLC, independent of therapy (Tsao, M. S. et al., N Engl J Med 2005; 353: 133-144). However, the presence of the EGFR exon 19 deletion or exon 21 L858R mutation is predictive of treatment benefit from EGFR-TKI therapy (Sequist, L. V. et al., J Clin Oncol 2008; 26: 2442-2449; Miller, V. A., J Clin Oncol 2008; 26: 1472-1478). High ERCC1 levels are prognostic of better survival for patients with NSCLC when compared with low levels of ERCC1 expression, independent of therapy (Simon, G. R. et al., Chest 2005; 127: 978-983; Olaussen K. A. et al., N Engl J Med 2006; 355: 983-991). High levels of ERCC1 expression are also predictive of poor response to platinum-based chemotherapy (Olaussen K. A. et al., N Engl J Med 2006; 355: 983-991; Bepler, G. et al., J Clin Oncol 2006; 24: 4731-4737). The presence of K-ras mutations is prognostic of poor survival for patients with NSCLC when compared with the absence of these mutations, independent of therapy (Slebos, R. J. et al., N Engl J Med 1990; 323: 561-565). Presence of K-ras mutations is also predictive of lack of benefit from platinum/vinorelbine chemotherapy or EGFR-TKI therapy (Miller, V. A., J Clin Oncol 2008; 26: 1472-1478; Tsao, M. S. et al., J Clin Oncol 2007; 25: 5240-5247). High RRM1 levels are prognostic of better survival for patients with NSCLC compared with low levels of RRM1 expression, independent of therapy (Bepler, G. et al., J Clin Oncol 2004; 22: 1878-1885; Zheng, Z. et al., N Engl J Med 2007; 356: 800-808). High levels of RRM1 expression are also predictive of poor response to gemcitabine-based chemotherapy (Bepler, G. et al., J Clin Oncol 2008; 26(Suppl 1): Abstract 8033; Reynolds, C. et al., J Clin Oncol 2009; 27: 5808-5815).

Treatment of NSCLC

Surgery

In general, for patients with stage I or II disease, surgery provides the best chance for cure (Ettinger, D. S. et al., J Natl Compr Canc Netw 2010; 8: 740-801). The surgical procedure used depends on the extent of disease and the cardiopulmonary reserve of the patient. If anatomically appropriate and margin-negative resection can be achieved, lung-sparing anatomic resection (sleeve lobectomy) is preferred over pneumonectomy. Otherwise, lobectomy or pneumonectomy are performed if physiologically feasible (Boffa, D. J. et al., J Thorac Cardiovasc Surg 2008; 135: 247-254; Scott, W. J. et al., Chest 2007; 132: 234S-242S). Resection (including wedge resection) is preferred over ablation (i.e., radiofrequency ablation [RFA], cryotherapy, stereotactic radiation) (Scott, W. J. et al., Chest 2007; 132: 234S-242S). However, whether lung-sparing surgeries (i.e., sublobular resection), such as segmentectomy and wedge resection, are useful in patients with severely reduced pulmonary function who are otherwise not candidates for surgery is controversial (Scott, W. J. et al., Chest 2007; 132: 234S-242S; Ginsberg, R. J. et al., Ann Thorac Surg 1995; 60: 615-622; Koike, T. et al., J Thorac Cardiovasc Surg 2003; 125: 924-928).

Radiation Therapy (RT)

RT can be used as 1) an adjunct for patients with resectable NSCLC who have no contraindications for surgery; 2) the primary local treatment (i.e., definitive RT) for patients with medically inoperable or unresectable NSCLC; and/or 3) an important palliative modality for patients with incurable NSCLC (Ettinger, D. S. et al., J Natl Compr Canc Netw 2010; 8: 740-801). However, conventional RT alone only results in a median survival of 10 months and a 5-year survival rate of 5% (Ettinger, D. S. et al., J Natl Compr Canc Netw 2010; 8: 740-801).

Chemotherapy

Many drugs are active against stage IV NSCLC. These drugs include the taxanes (paclitaxel, docetaxel), vinorelbine, etoposide, pemetrexed, the camptothecin analogs (irinotecan), and gemcitabine. Combinations using many of these drugs produce 1-year survival rates of 30% to 40% and are superior to single agents. Regimens include carboplatin/paclitaxel, cisplatin/paclitaxel, cisplatin/vinorelbine, gemcitabine/cisplatin, cisplatin/pemetrexed, and docetaxel/cisplatin (Ettinger, D. S. et al., J Natl Compr Canc Netw 2010; 8: 740-801; Ohe, Y. et al., Ann Oncol 2007; 18: 317-323; Fossella, F. et al., J Clin Oncol 2003; 21: 3016-3024; Smit, E. F. et al., J Clin Oncol 2003; 21: 3909-3917; Zatloukal, P. et al., Lung Cancer 2004; 46: 87-98; Scagliotti, G. V. et al., J Clin Oncol 2008; 26: 3543-3551).

Although chemotherapy is appropriate for many patients with lung cancer, there is a consensus that the use of traditional chemotherapeutic agents to treat NSCLC has reached a therapeutic plateau (Molina, J. R. et al., Mayo Clin Proc 2008 May; 83(5): 584-594).

Targeted Therapy

Specific targeted therapies have been developed for treating advanced lung cancer (Sandler, A. B. et al., Clin Cancer Res 2004; 10: 4258s-4262s; Giaccone, G. et al., J Clin Oncol 2005; 23: 3235-3242). Bevacizumab is a recombinant monoclonal antibody that blocks vascular endothelial growth factor (VEGF). Erlotinib is a small molecule inhibitor of EGFR. Cetuximab is a monoclonal antibody that targets EGFR.

In 2006, the FDA approved bevacizumab for patients with unresectable, locally advanced, recurrent, or metastatic non-squamous NSCLC (Ettinger, D. S. et al., J Natl Compr Canc Netw 2010; 8: 740-801). It has been recommended that bevacizumab be used in combination with paclitaxel and carboplatin for select patients with advanced nonsquamous NSCLC (Sandler, A. et al., N Engl J Med 2006; 355: 2542-2550). To undergo treatment with bevacizumab and chemotherapy, patients must have nonsquamous NSCLC and no history of hemoptysis. Any regimen with a high risk for thrombocytopenia (i.e., possible bleeding) should be used with caution when combined with bevacizumab (Ettinger, D. S. et al., J Natl Compr Canc Netw 2010; 8: 740-801).

In 2004, the FDA approved Erlotinib for the treatment of patients with locally advanced or metastatic NSCLC after failure of at least one prior chemotherapy regimen (Ettinger, D. S. et al., J Natl Compr Canc Netw 2010; 8: 740-801). However, erlotinib can also be given as first-line therapy in patients with advanced or metastatic NSCLC who have a known active EGFR mutation or gene amplification (Sequist, L. V. et al., Oncologist 2007; 12: 90-98; N Eng J Med 2009; 361: 947-957; Inoue, A. et al., J Clin Oncol 2009; 27: 1394-1400).

A recent phase III randomized trial assessed cisplatin/vinorelbine with or without cetuximab for patients with advanced NSCLC (Pirker, R. et al., Lancet 2009; 373: 1525-1531). The results indicated that adding cetuximab slightly increased overall survival (11.3 vs. 10.1 months; P=0.04) (Pirker, R. et al., Lancet 2009; 373: 1525-1531; Ettinger, D. S. et al., J Natl Compr Canc Netw 2010; 8: 740-801).

However, there is accumulating evidence that NSCLC acquires resistance to these specific targeted therapies (e.g., erlotinib and gefitinib) and how cancers such as NSCLC become resistant to, for example, EGFR inhibitors (Ettinger, D. S. et al., J Natl Compr Canc Netw 2010; 8: 740-801). The most common known mechanism is the acquisition of a secondary mutation in EGFR, known as T790M, which renders the kinase resistant to erlotinib and gefitinib (Nguyen, K. S. et al., Clin Lung Cancer 2009; 10: 281-289; Gazdar, A. F., Oncogene 2009; 28(Suppl 1): S24-S31). Amplification of the MET oncogene is another validated resistance mechanism (Ettinger, D. S. et al., J Natl Compr Canc Netw 2010; 8: 740-801).

DNA Damage-Signaling in Human Tumors

DNA damage signaling and checkpoint control pathways are among the most commonly mutated networks in human tumors (Morandell, S. et al., Cell Reports 5, 868-877, Nov. 27, 2013; Negrini, S. et al., Nat Rev Mol Cell Biol 2010; 11: 220-228). The three major DNA damage-responsive cell cycle checkpoints are the G1/S checkpoint, intra S-phase checkpoint, and the G2/M checkpoint. In response to DNA damage, eukaryotic cells activate complex signaling networks that mediate DNA repair and cell cycle arrest or, if the damage is extensive, trigger apoptosis (Ciccia, A. and Elledge, S. J., Mol Cell 2010; 40: 179-204). Three canonical protein kinase pathways in both normal and cancer cells arrest the cell cycle in response to damaged DNA: the Ataxia-Telangiectasia and Rad-3 related through Chk1 (ATR-Chk1) pathway, the Ataxia-Telangiectasia mutated through Chk2 (ATM-Chk2) pathway, and the stress-activated protein kinases p38 mitogen-activated protein kinase (MAPK) and its substrate MAPKAP kinase-2 (MK2) (Morandell, S. et al., Cell Reports 5, 868-877, Nov. 27, 2013). The ATM/Chk2 pathway responds primarily to DNA double strand breaks, while the ATRpChk1 pathway is activated by bulky DNA lesions, and following replication fork collapse during S-phase. In contrast to the DNA damage-specific activation of Chk1 and Chk2, the p38MAPK pathway is a general stress-activated kinase pathway that responds to various cellular stimuli, including cytokines, hyperosmolarity, and UV irradiation.

Tumor suppressor protein p53 is a major downstream effector of the aforementioned DNA damage kinase pathways. In normal cells, p53-dependent signaling results in G1 arrest, mainly mediated by transcriptional upregulation of p21. P21 also appears to play a role in sustaining the G2 checkpoint after gamma-irradiation. If DNA damage is extensive, however, p53-dependent pathways target the damaged cell for apoptotic cell death. The MK2 pathway is critical for arresting the cell cycle after genotoxic stress, including cisplatin-induced DNA crosslinks and topoisomerase-inhibitor-induced DNA strand breaks only in tumor cells that lack functional p53 (Manke, I. A. et al., Mol Cell 2005; 17: 37-48; Reinhardt, H. C. et al., Cancer Cell 2007; 11: 175-189). Both the ATRChk1 pathway and the p38-MK2 pathway are required for effective cell-cycle checkpoint function in the absence of p53 (Reinhardt, H. C. et al., Mol Cell 2010; 40: 34-49).

Recently, Morandell et al. (Cell Reports 5, 868-877, Nov. 27, 2013) showed that, in response to genotoxic chemotherapy, MK2 is essential for the survival of NSCLC tumor cells that lack functional p53 but is dispensable in p53-proficient cells. MK2 was found to specifically sensitize p53-deficient tumors to the DNA-damaging agent cisplatin but had no effect on the treatment response of p53-proficient cancer cells. This suggests a potential for enhancement chemosensitization of p53-deficient tumors to DNA-damaging chemotherapy in vivo through synthetic lethality between p53 and MK2 (Morandell, S. et al., Cell Reports 5, 868-877, Nov. 27, 2013).

Kinases

Kinases are a ubiquitous group of enzymes that catalyze the phosphoryl transfer reaction from a phosphate donor (usually adenosine-5'-triphosphate (ATP)) to a receptor substrate. A classification of all available kinase sequences (approximately 60,000 sequences) indicates kinases can be grouped into 25 families of homologous (meaning derived from a common ancestor) proteins. These kinase families are assembled into 12 fold groups based on similarity of structural fold. Further, 22 of the 25 families (approximately 98.8% of all sequences) belong to 10 fold groups for which the structural fold is known. Of the other 3 families, polyphosphate kinase forms a distinct fold group, and the 2 remaining families are both integral membrane kinases and comprise the final fold group. These fold groups not only include some of the most widely spread protein folds, such as Rossmann-like fold (three or more parallel β strands linked by two α helices in the topological order β-α-β-α-β), ferredoxin-like fold (a common α-β protein fold with a signature βαββαβ secondary structure along its backbone), TIM-barrel fold (meaning a conserved protein fold consisting of eight α-helices and eight parallel β-strands that alternate along the peptide backbone), and antiparallel β-barrel fold (a beta barrel is a large beta-sheet that twists and coils to form a closed structure in which the first strand is hydrogen bonded to the last), but also all major classes (all α, all β, α+β, α/β) of protein structures. Within a fold group, the core of the nucleotide-binding domain of each family has the same architecture, and the topology of the protein core is either identical or related by circular permutation. Homology between the families within a fold group is not implied.

Group I (23,124 sequences) kinases incorporate protein S/T-Y kinase, atypical protein kinase, lipid kinase, and ATP grasp enzymes and further comprise the protein S/T-Y kinase, and atypical protein kinase family (22,074 sequences). These kinases include: choline kinase (EC 2.7.1.32); protein kinase (EC 2.7.137); phosphorylase kinase (EC 2.7.1.38); homoserine kinase (EC 2.7.1.39); I-phosphatidylinositol 4-kinase (EC 2.7.1.67); streptomycin 6-kinase (EC 2.7.1.72); ethanolamine kinase (EC 2.7.1.82); streptomycin 3'-kinase (EC 2.7.1.87); kanamycin kinase (EC 2.7.1.95); 5-methylthioribose kinase (EC 2.7.1.100); viomycin kinase (EC 2.7.1.103); [hydroxymethylglutaryl-CoA reductase (NADPH2)] kinase (EC 2.7.1.109); protein-tyrosine kinase (EC 2.7.1.112); [isocitrate dehydrogenase (NADP+)] kinase (EC 2.7.1.116); [myosin light-chain] kinase (EC 2.7.1.117); hygromycin-B kinase (EC 2.7.1.119); calcium/calmodulin-dependent protein kinase (EC 2.7.1.123); rhodopsin kinase (EC 2.7.1.125); [beta-adrenergic-receptor] kinase (EC 2.7.1.126); [myosin heavy-chain] kinase (EC 2.7.1.129); [Tau protein] kinase (EC 2.7.1.135); macrolide 2'-kinase (EC 2.7.1.136); I-phosphatidylinositol 3-kinase (EC 2.7.1.137); [RNA-polymerase]-subunit kinase (EC 2.7.1.141); phosphatidylinositol-4,5-bisphosphate 3-kinase (EC 2.7.1.153); and phosphatidylinositol-4-phosphate 3-kinase (EC 2.7.1.154). Group I further comprises the lipid kinase family (321 sequences). These kinases include: I-phosphatidylinositol-4-phosphate 5-kinase (EC 2.7.1.68); I D-myo-inositol-triphosphate 3-kinase (EC 2.7.1.127); inositol-tetrakisphosphate 5-kinase (EC 2.7.1.140); I-phosphatidylinositol-5-phosphate 4-kinase (EC 2.7.1.149); I-phosphatidylinositol-3-phosphate 5-kinase (EC 2.7.1.150); inositol-polyphosphate multikinase (EC 2.7.1.151); and inositol-hexakiphosphate kinase (EC 2.7.4.21). Group I further comprises the ATP-grasp kinases (729 sequences) which include inositol-tetrakisphosphate I-kinase (EC 2.7.1.134); pyruvate, phosphate dikinase (EC 2.7.9.1); and pyruvate, water dikinase (EC 2.7.9.2).

Group II (17,071 sequences) kinases incorporate the Rossman-like kinases. Group II comprises the P-loop kinase family (7,732 sequences). These include gluconokinase (EC 2.7.1.12); phosphoribulokinase (EC 2.7.1.19); thymidine kinase (EC 2.7.1.21); ribosylnicotinamide kinase (EC 2.7.1.22); dephospho-CoA kinase (EC 2.7.1.24); adenylylsulfate kinase (EC 2.7.1.25); pantothenate kinase (EC 2.7.1.33); protein kinase (bacterial) (EC 2.7.1.37); uridine kinase (EC 2.7.1.48); shikimate kinase (EC 2.7.1.71); deoxycytidine kinase (EC 2.7.1.74); deoxyadenosine kinase (EC 2.7.1.76); polynucleotide 5'-hydroxyl-kinase (EC 2.7.1.78); 6-phosphofructo-2-kinase (EC 2.7.1.105); deoxyguanosine kinase (EC 2.7.1.113); tetraacyldisaccharide 4'-kinase (EC 2.7.1.130); deoxynucleoside kinase (EC 2.7.1.145); adenosylcobinamide kinase (EC 2.7.1.156); polyphosphate kinase (EC 2.7.4.1); phosphomevalonate kinase (EC 2.7.4.2); adenylate kinase (EC 2.7.4.3); nucleoside-phosphate kinase (EC 2.7.4.4); guanylate kinase (EC 2.7.4.8); thymidylate kinase (EC 2.7.4.9); nucleoside-triphosphate-adenylate kinase (EC 2.7.4.10); (deoxy) nucleoside-phosphate kinase (EC 2.7.4.13); cytidylate kinase (EC 2.7.4.14); and uridylate kinase (EC 2.7.4.22). Group II further comprises the phosphoenolpyruvate carboxykinase family (815 sequences). These enzymes include protein kinase (HPr kinase/phosphatase) (EC 2.7.1.37); phosphoenolpyruvate carboxykinase (GTP) (EC 4.1.1.32); and phosphoenolpyruvate carboxykinase (ATP) (EC 4.1.1.49). Group II further comprises the phosphoglycerate kinase (1,351 sequences) family. These enzymes include phosphoglycerate kinase (EC 2.7.2.3) and phosphoglycerate kinase (GTP) (EC 2.7.2.10). Group II further comprises the aspartokinase family (2,171 sequences). These enzymes include carbamate kinase (EC 2.7.2.2); aspartate kinase (EC 2.7.2.4); acetylglutamate kinase (EC 2.7.2.8 1); glutamate 5-kinase (EC 2.7.2.1) and uridylate kinase (EC 2.7.4.). Group II further comprises the phosphofructokinase-like kinase family (1,998 sequences). These enzymes include 6-phosphofrutokinase (EC 2.7.1.11); NAD(+) kinase (EC 2.7.1.23); I-phosphofructokinase (EC 2.7.1.56); diphosphate-fructose-6-phosphate I-phosphotransferase (EC 2.7.1.90); sphinganine kinase (EC 2.7.1.91); diacylglycerol kinase (EC 2.7.1.107); and ceramide kinase (EC 2.7.1.138). Group II further comprises the ribokinase-like family (2,722 sequences). These enzymes include: glucokinase (EC 2.7.1.2); ketohexokinase (EC 2.7.1.3); fructokinase (EC 2.7.1.4); 6-phosphofructokinase (EC 2.7.1.11); ribokinase (EC 2.7.1.15); adenosine kinase (EC 2.7.1.20); pyridoxal kinase (EC 2.7.1.35); 2-dehydro-3-deoxygluconokinase (EC 2.7.1.45); hydroxymethylpyrimidine kinase (EC 2.7.1.49); hydroxyethylthiazole kinase (EC 2.7.1.50); I-phosphofructokinase (EC 2.7.1.56); inosine kinase (EC 2.7.1.73); 5-dehydro-2-deoxygluconokinase (EC 2.7.1.92); tagatose-6-phosphate kinase (EC 2.7.1.144); ADP-dependent phosphofructokinase (EC 2.7.1.146); ADP-dependent glucokinase (EC 2.7.1.147); and phosphomethylpyrimidine kinase (EC 2.7.4.7). Group II further comprises the thiamin pyrophosphokinase family (175 sequences) which includes thiamin pyrophosphokinase (EC 2.7.6.2). Group II further comprises the glycerate kinase family (107 sequences) which includes glycerate kinase (EC 2.7.1.31).

Group III kinases (10,973 sequences) comprise the ferredoxin-like fold kinases. Group III further comprises the nucleoside-diphosphate kinase family (923 sequences). These enzymes include nucleoside-diphosphate kinase (EC 2.7.4.6). Group III further comprises the HPPK kinase family (609 sequences). These enzymes include 2-amino-4-hydroxy-6-hydroxymethyldihydropteridine pyrophosphokinase (EC 2.7.6.3). Group III further comprises the guanido kinase family (324 sequences). These enzymes include guanidoacetate kinase (EC 2.7.3.1); creatine kinase (EC 2.7.3.2); arginine kinase (EC 2.7.3.3); and lombricine kinase (EC 2.7.3.5). Group III further comprises the histidine kinase family (9,117 sequences). These enzymes include protein kinase (histidine kinase) (EC 2.7.1.37); [pyruvate dehydrogenase (lipoamide)] kinase (EC 2.7.1.99); and [3-methyl-2-oxybutanoate dehydrogenase(lipoamide)] kinase (EC 2.7.1.115).

Group IV kinases (2,768 sequences) incorporate ribonuclease H-like kinases. These enzymes include hexokinase (EC 2.7.1.1); glucokinase (EC 2.7.1.2); fructokinase (EC 2.7.1.4); rhamnulokinase (EC 2.7.1.5); mannokinase (EC 2.7.1.7); gluconokinase (EC 2.7.1.12); L-ribulokinase (EC 2.7.1.16); xylulokinase (EC 2.7.1.17); erythritol kinase (EC 2.7.1.27); glycerol kinase (EC 2.7.1.30); pantothenate kinase (EC 2.7.1.33); D-ribulokinase (EC 2.7.1.47); L-fucolokinase (EC 2.7.1.51); L-xylulokinase (EC 2.7.1.53); allose kinase (EC 2.7.1.55); 2-dehydro-3-deoxygalactonokinase (EC 2.7.1.58); N-acetylglucosamine kinase (EC 2.7.1.59); N-acylmannosamine kinase (EC 2.7.1.60); polyphosphate-glucose phosphotransferase (EC 2.7.1.63); beta-glucoside kinase (EC 2.7.1.85); acetate kinase (EC 2.7.2.1); butyrate kinase (EC 2.7.2.7); branched-chain-fatty-acid kinase (EC 2.7.2.14); and propionate kinase (EC 2.7.2.15).

Group V kinases (1,119 sequences) incorporate TIM β-barrel kinases. These enzymes include pyruvate kinase (EC 2.7.1.40).

Group VI kinases (885 sequences) incorporate GHMP kinases. These enzymes include galactokinase (EC 2.7.1.6); mevalonate kinase (EC 2.7.1.36); homoserine kinase (EC 2.7.1.39); L-arabinokinase (EC 2.7.1.46); fucokinase (EC 2.7.1.52); shikimate kinase (EC 2.7.1.71); 4-(cytidine 5'-diphospho)-2-C-methyl-D-erythriol kinase (EC 2.7.1.148); and phosphomevalonate kinase (EC 2.7.4.2).

Group VII kinases (1,843 sequences) incorporate AIR synthetase-like kinases. These enzymes include thiaminephosphate kinase (EC 2.7.4.16) and selenide, water dikinase (EC 2.7.9.3).

Group VIII kinases (565 sequences) incorporate riboflavin kinases (565 sequences). These enzymes include riboflavin kinase (EC 2.7.1.26).

Group IX kinases (197 sequences) incorporate dihydroxyacetone kinases. These enzymes include glycerone kinase (EC 2.7.1.29).

Group X kinases (148 sequences) incorporate putative glycerate kinases. These enzymes include glycerate kinase (EC 2.7.1.31).

Group XI kinases (446 sequences) incorporate polyphosphate kinases. These enzymes include polyphosphate kinases (EC 2.7.4.1).

Group XII kinases (263 sequences) incorporate integral membrane kinases. Group XII comprises the dolichol kinase family. These enzymes include dolichol kinases (EC 2.7.1.108). Group XII further comprises the undecaprenol kinase family. These enzymes include undecaprenol kinases (EC 2.7.1.66).

Kinases play indispensable roles in numerous cellular metabolic and signaling pathways, and are among the best-studied enzymes at the structural, biochemical, and cellular level. Despite the fact that all kinases use the same phosphate donor (in most cases, ATP) and catalyze apparently the same phosphoryl transfer reaction, they display remarkable diversity in their structural folds and substrate recognition mechanisms. This probably is due largely to the diverse nature of the structures and properties of their substrates.

Mitogen-Activated Protein Kinase (MAPK)-Activated Protein Kinases (MK2 and MK3)

Different groups of MAPK-activated protein kinases (MAP-KAPKs) have been defined downstream of mitogen-activated protein kinases (MAPKs). These enzymes transduce signals to target proteins that are not direct substrates of the MAPKs and, therefore, serve to relay phosphorylation-dependent signaling with MAPK cascades to diverse cellular functions. One of these groups is formed by the three MAPKAPKs: MK2, MK3 (also known as 3pK), and MK5 (also designated PRAK). Mitogen-activated protein kinase-activated protein kinase 2 (also referred to as "MAP-KAPK2", "MAPKAP-K2", "MK2") is a kinase of the serine/threonine (Ser/Thr) protein kinase family. MK2 is highly homologous to MK3 (approximately 75% amino acid identity). The kinase domains of MK2 and MK3 are most similar (approximately 35% to 40% identity) to calcium/calmodulin-dependent protein kinase (CaMK), phosphorylase b kinase, and the C-terminal kinase domain (CTKD) of the ribosomal S6 kinase (RSK) isoforms. The MK2 gene encodes two alternatively spliced transcripts of 370 amino acids (MK2A) and 400 amino acids (MK2B). The MK3 gene encodes one transcript of 382 amino acids. The MK2- and MK3 proteins are highly homologous, yet MK2A possesses a shorter C-terminal region. The C-terminus of MK2B contains a functional bipartite nuclear localization sequence (NLS) (Lys-Lys-Xaa-Xaa-Xaa-Xaa-Xaa-Xaa-Xaa-Xaa-Xaa-Xaa-Lys-Arg-Arg-Lys-Lys; SEQ ID NO: 21) that is not present in the shorter MK2A isoform, indicating that alternative splicing determines the cellular localization of the MK2 isoforms. MK3 possesses a similar nuclear localization sequence. The nuclear localization sequence found in both MK2B and MK3 encompasses a D domain (Leu-Leu-Lys-Arg-Arg-Lys-Lys; SEQ ID NO: 22), which was shown to mediate the specific interaction of MK2B and MK3 with p38α and p38β. MK2B and MK3 also possess a functional nuclear export signal (NES) located N-terminal to the NLS and D domain. The NES in MK2B is sufficient to trigger nuclear export following stimulation, a process which may be inhibited by leptomycin B. The sequence N-terminal to the catalytic domain in MK2 and MK3 is proline rich and contains one (MK3) or two (MK2) putative Src homology 3 (SH3) domain-binding sites, which studies have shown, for MK2, to mediate binding to the SH3 domain of c-Abl in vitro. Recent studies suggest that this domain is involved in MK2-mediated cell migration.

MK2B and MK3 are located predominantly in the nucleus of quiescent cells while MK2A is present in the cytoplasm. Both MK2B and MK3 are rapidly exported to the cytoplasm via a chromosome region maintenance protein (CRM1)-dependent mechanism upon stress stimulation. Nuclear export of MK2B appears to be mediated by kinase activation, as phosphomimetic mutation of Thr334 within the activation loop of the kinase enhances the cytoplasmic localization of MK2B. Without being limited by theory, it is thought that MK2B and MK3 may contain a constitutively active nuclear localization signal (NLS) and a phosphorylation-regulated nuclear export signal (NES).

MK2 and MK3 appear to be expressed ubiquitously, with increased relative expression in the heart, lungs, kidney, reproductive organs (mammary and testis), skin and skeletal muscle tissues, as well as in immune-related cells such as white blood cells/leukocytes and dendritic cells.

Activation of MK2 and MK3 Activity

Various activators of p38α and p38β potently stimulate MK2 and MK3 activity. p38 mediates the in vitro and in vivo phosphorylation of MK2 on four proline-directed sites: Thr25, Thr222, Ser272, and Thr334. Of these sites, only Thr25 is not conserved in MK3. Without being limited by theory, while the function of phosphorylated Thr25 is unknown, its location between the two SH3 domain-binding sites suggests that it may regulate protein-protein interactions. Thr222 in MK2 (Thr201 in MK3) is located in the activation loop of the kinase domain and has been shown to be essential for MK2 and MK3 kinase activity. Thr334 in MK2 (Thr313 in MK3) is located C-terminal to the catalytic domain and is essential for kinase activity. The crystal structure of MK2 has been resolved and, without being limited by theory, suggests that Thr334 phosphorylation may serve as a switch for MK2 nuclear import and export. Phosphorylation of Thr334 also may weaken or interrupt binding of the C terminus of MK2 to the catalytic domain, exposing the NES and promoting nuclear export.

Studies have shown that while p38 is capable of activating MK2 and MK3 in the nucleus, experimental evidence suggests that activation and nuclear export of MK2 and MK3 are coupled by a phosphorylation-dependent conformational switch that also dictates p38 stabilization and localization, and the cellular location of p38 itself is controlled by MK2 and possibly MK3. Additional studies have shown that nuclear p38 is exported to the cytoplasm in a complex with MK2 following phosphorylation and activation of MK2. The interaction between p38 and MK2 may be important for p38 stabilization since studies indicate that p38 levels are low in MK2-deficient cells and expression of a catalytically inactive MK2 protein restores p38 levels.

Substrates and Functions

MK2 shares many substrates with MK3. Both enzymes have comparable substrate preferences and phosphorylate peptide substrates with similar kinetic constants. The minimum sequence required for efficient phosphorylation by MK2 was found to be Hyd-Xaa-Arg-Xaa-Xaa-pSer/pThr (SEQ ID NO: 22), where Hyd is a bulky, hydrophobic residue.

Accumulating evidence has shown that MK2 phophorylates a variety of proteins, which include, but are not limited to, 5-Lipooxygenase (ALOX5), Cell Division Cycle 25 Homolog B (CDC25B), Cell Division Cycle 25 Homolog C (CDC25C), Embryonic Lethal, Abnormal Vision, *Drosophila*-Like 1 (ELAVL1), Heterogeneous Nuclear Ribonucleoprotein A0 (HNRNPA0), Heat Shock Factor protein 1 (HSF1), Heat Shock Protein Beta-1 (HSPB1), Keratin 18 (KRT18), Keratin 20 (KRT20), LIM domain kinase 1 (LIMK1), Lymphocyte-specific protein 1 (LSP1), Polyadenylate-Binding Protein 1 (PABPC1), Poly(A)-specific Ribonuclease (PARN), CAMP-specific 3',5'-cyclic Phosphodiesterase 4A (PDE4A), RCSD domain containing 1 (RCSD1), Ribosomal protein S6 kinase, 90 kDa, polypeptide 3 (RPS6KA3), TGF-beta activated kinase 1/MAP3K7 binding protein 3 (TAB3), and Tristetraprolin (TTP/ZFP36).

Heat-Shock Protein Beta-1 (also termed HSPB1 or HSP27) is a stress-inducible cytosolic protein that is ubiquitously present in normal cells and is a member of the small heat-shock protein family. The synthesis of HSPB1 is induced by heat shock and other environmental or pathophysiologic stresses, such as UV radiation, hypoxia and ischemia. Besides its putative role in thermoresistance, HSPB1 is involved in the survival and recovery of cells exposed to stressful conditions.

Experimental evidence supports a role for p38 in the regulation of cytokine biosynthesis and cell migration. The targeted deletion of the mk2 gene in mice suggested that although p38 mediates the activation of many similar kinases, MK2 seems to be the key kinase responsible for these p38-dependent biological processes. Loss of MK2 leads (i) to a defect in lipopolysaccharide (LPS)-induced synthesis of cytokines such as tumor necrosis factor alpha (TNF-α), interleukin-6 (IL-6), and gamma interferon (IFN-γ) and (ii) to changes in the migration of mouse embryonic fibroblasts, smooth muscle cells, and neutrophils.

Consistent with a role for MK2 in inflammatory and immune responses, MK2-deficient mice showed increased susceptibility to *Listeria monocytogenes* infection and reduced inflammation-mediated neuronal death following focal ischemia. Since the levels of p38 protein also are reduced significantly in MK2-deficient cells, it was necessary to distinguish whether these phenotypes were due solely to the loss of MK2. To achieve this, MK2 mutants were expressed in MK2-deficient cells, and the results indicated that the catalytic activity of MK2 was not necessary to restore p38 levels but was required to regulate cytokine biosynthesis.

Knockout or knockdown studies of MK2 provide strong support that activated MK2 enhances stability of IL-6 mRNA through phosphorylation of proteins interacting with the AU-rich 3' untranslated region of IL-6 mRNA. In particular, it has been shown that MK2 is principally responsible for phosphorylation of hnRNPA0, an mRNA-binding protein that stabilizes IL-6 RNA. In addition, several additional studies investigating diverse inflammatory diseases have found that levels of pro-inflammatory cytokines, such as IL-6, IL-1β, TNF-α and IL-8, are increased in induced sputum from patients with stable chronic obstructive pulmonary disease (COPD) or from the alveolar macrophages of cigarette smokers (Keatings V. et al, Am J Resp Crit Care Med, 1996, 153:530-534; Lim, S. et al., J Respir Crit Care Med, 2000, 162:1355-1360).

Regulation of mRNA Translation.

Previous studies using MK2 knockout mice or MK2-deficient cells have shown that MK2 increases the production of inflammatory cytokines, including TNF-α, IL-1, and IL-6, by increasing the rate of translation of its mRNA. No significant reductions in the transcription, processing, and shedding of TNF-α could be detected in MK2-deficient mice. The p38 pathway is known to play an important role in regulating mRNA stability, and MK2 represents a likely target by which p38 mediates this function. Studies utilizing MK2-deficient mice indicated that the catalytic activity of MK2 is necessary for its effects on cytokine production and migration, suggesting that, without being limited by theory, MK2 phosphorylates targets involved in mRNA stability. Consistent with this, MK2 has been shown to bind and/or phosphorylate the heterogeneous nuclear ribonucleoprotein (hnRNP) A0, tristetraprolin (TTP), the poly(A)-binding protein PABP1, and HuR, a ubiquitously expressed member of the ELAV (Embryonic-Lethal Abnormal Visual in *Drosophila melanogaster*) family of RNA-binding protein. These substrates are known to bind or copurify with mRNAs that contain AU-rich elements in the 3' untranslated region, suggesting that MK2 may regulate the stability of AU-rich mRNAs such as TNF-α. It currently is unknown whether MK3 plays a similar role, but LPS treatment of MK2-deficient fibroblasts completely abolished hnRNP A0 phosphorylation, suggesting that MK3 is not able to compensate for the loss of MK2.

MK3 participates with MK2 in phosphorylation of the eukaryotic elongation factor 2 (eEF2) kinase. eEF2 kinase phosphorylates and inactivates eEF2. eEF2 activity is critical for the elongation of mRNA during translation, and phosphorylation of eEF2 on Thr56 results in the termination of mRNA translation. MK2 and MK3 phosphorylation of eEF2 kinase on Ser377 suggests that these enzymes may modulate eEF2 kinase activity and thereby regulate mRNA translation elongation.

Transcriptional Regulation by MK2 and MK3

Nuclear MK2, similar to many MKs, contributes to the phosphorylation of cAMP response element binding (CREB), Activating Transcription Factor-1 (ATF-1), serum response factor (SRF), and transcription factor ER81. Comparison of wild-type and MK2-deficient cells revealed that MK2 is the major SRF kinase induced by stress, suggesting a role for MK2 in the stress-mediated immediate-early response. Both MK2 and MK3 interact with basic helix-loop-helix transcription factor E47 in vivo and phosphorylate E47 in vitro. MK2-mediated phosphorylation of E47 was found to repress the transcriptional activity of E47 and thereby inhibit E47-dependent gene expression, suggesting that MK2 and MK3 may regulate tissue-specific gene expression and cell differentiation.

Other Targets of MK2 and MK3

Several other MK2 and MK3 substrates also have been identified, reflective of the diverse functions of MK2 and MK3 in several biological processes. The scaffolding protein 14-3-3ζ is a physiological MK2 substrate. Studies indicate that 14-3-3ζ interacts with a number of components of cell signaling pathways, including protein kinases, phosphatases, and transcription factors. Additional studies have shown that MK2-mediated phosphorylation of 14-3-3ζ on Ser58 compromises its binding activity, suggesting that MK2 may affect the regulation of several signaling molecules normally regulated by 14-3-3ζ.

Additional studies have shown that MK2 also interacts with and phosphorylates the p16 subunit of the seven-member Arp2 and Arp3 complex (p16-Arc) on Ser77. p16-Arc has roles in regulating the actin cytoskeleton, suggesting that MK2 may be involved in this process. Further studies have shown that the small heat shock protein HSPB1, lymphocyte-specific protein LSP-1, and vimentin are phosphorylated by MK2. HSPB1 forms large oligomers which may act as molecular chaperones and protect cells from heat shock and oxidative stress. Upon phosphorylation, HSPB1 loses its ability to form large oligomers and is unable to block actin polymerization, suggesting that MK2-mediated phosphorylation of HSPB1 serves a homeostatic function aimed at regulating actin dynamics that otherwise would be destabilized during stress. MK3 also was shown to phosphorylate HSPB1 in vitro and in vivo, but its role during stressful conditions has not yet been elucidated.

It was also shown that HSPB1 binds to polyubiquitin chains and to the 26S proteasome in vitro and in vivo. The ubiquitin-proteasome pathway is involved in the activation of transcription factor NF-kappa B (NF-κB) by degrading its main inhibitor, I kappa B-alpha (IκB-alpha), and it was shown that overexpresion of HSPB1 increases NF-kappaB (NF-κB) nuclear relocalization, DNA binding, and transcriptional activity induced by etoposide, TNF-alpha, and Interleukin-1 beta (IL-1β). Additionally, previous studies have suggested that HSPB1, under stress conditions, favors the degradation of ubiquitinated proteins, such as phosphorylated I kappa B-alpha (IκB-alpha); and that this function of HSPB1 accounts for its anti-apoptotic properties through the enhancement of NF-kappa B (NF-κB) activity (Parcellier, A. et al., Mol Cell Biol, 23(16): 5790-5802, 2003).

MK2 and MK3 also may phosphorylate 5-lipoxygenase. 5-lipoxygenase catalyzes the initial steps in the formation of the inflammatory mediators, leukotrienes. Tyrosine hydroxylase, glycogen synthase, and Akt also were shown to be phosphorylated by MK2.

MK2 phosphorylates the tumor suppressor protein tuberin on Ser1210, creating a docking site for 14-3-3ζ. Tuberin and hamartin normally form a functional complex that negatively regulates cell growth by antagonizing mTOR-dependent signaling, suggesting that p38-mediated activation of MK2 may regulate cell growth by increasing 14-3-3ζ binding to tuberin.

Accumulating evidence has suggested that the reciprocal crosstalk between the p38 MAPK-pathway and signal transducer and activator of transcription 3 (STAT3)-mediated signal-transduction forms a critical axis successively activated in lipopolysaccharide (LPS) challenge models. It was shown that the balanced activation of this axis is essential for both induction and propagation of the inflammatory macrophage response as well as for the control of the resolution phase, which is largely driven by IL-10 and sustained STAT3 activation (Bode, J. et al., Cellular Signalling, 24: 1185-1194, 2012). In addition, another study has shown that MK2 controls LPS-inducible IFNβ gene expression and subsequent IFNβ-mediated activation of STAT3 by neutralizing negative regulatory effects of MK3 on LPS-induced p65 and IRF3-mediated signaling. In mk2/3 knockout macrophages, IFNβ-dependent STAT3 activation occurred independently from IL-10, because, in contrast to IFNβ-, impaired IL-10 expression is not restored upon additional deletion of MK3 in mk2/3 knockout macrophages (Ehlting, C. et al., J. Biol. Chem., 285(27): 24113-24124).

Kinase Inhibition

The eukaryotic protein kinases constitute one of the largest superfamilies of homologous proteins that are related by virtue of their catalytic domains. Most related protein kinases are specific for either serine/threonine or tyrosine phosphorylation. Protein kinases play an integral role in the cellular response to extracellular stimuli. Thus, stimulation of protein kinases is considered to be one of the most common activation mechanisms in signal transduction systems. Many substrates are known to undergo phosphorylation by multiple protein kinases, and a considerable amount of information on primary sequence of the catalytic domains of various protein kinases has been published. These sequences share a large number of residues involved in ATP binding, catalysis, and maintenance of structural integrity. Most protein kinases possess a well conserved 30-32 kDa catalytic domain.

Studies have attempted to identify and utilize regulatory elements of protein kinases. These regulatory elements include inhibitors, antibodies, and blocking peptides.

Inhibitors

Enzyme inhibitors are molecules that bind to enzymes thereby decreasing enzyme activity. The binding of an inhibitor may stop a substrate from entering the active site of the enzyme and/or hinder the enzyme from catalyzing its reaction (as in inhibitors directed at the ATP biding site of the kinase). Inhibitor binding is either reversible or irreversible. Irreversible inhibitors usually react with the enzyme and change it chemically (e.g., by modifying key amino acid residues needed for enzymatic activity) so that it no longer is capable of catalyzing its reaction. In contrast, reversible inhibitors bind non-covalently, and different types of inhibition are produced depending on whether these inhibitors bind the enzyme, the enzyme-substrate complex, or both.

Enzyme inhibitors often are evaluated by their specificity and potency. The term "specificity" as used in this context refers to the selective attachment of an inhibitor or its lack of binding to other proteins. The term "potency" as used herein refers to an inhibitor's dissociation constant, which indicates the concentration of inhibitor needed to inhibit an enzyme.

Inhibitors of protein kinases have been studied for use as a tool in protein kinase activity regulation. Inhibitors have been studied for use with, for example, cyclin-dependent (Cdk) kinase, MAP kinase, serine/threonine kinase, Src Family protein tyrosine kinase, tyrosine kinase, calmodulin (CaM) kinase, casein kinase, checkpoint kinase (Chk1), glycogen synthase kinase 3 (GSK-3), c-Jun N-terminal kinase (JNK), mitogen-activated protein kinase 1 (MEK), myosin light chain kinase (MLCK), protein kinase A, Akt (protein kinase B), protein kinase C, protein kinase G, protein tyrosine kinase, Raf kinase, and Rho kinase.

Small-Molecule MK2 Inhibitors

While individual inhibitors that target MK2 with at least modest selectivity with respect to other kinases have been designed, it has been difficult to create compounds with favorable solubility and permeability. As a result, there are relatively few biochemically efficient MK2 inhibitors that have advanced to in vivo pre-clinical studies (Edmunds, J. and Talanian, MAPKAP Kinase 2 (MK2) as a Target for Anti-inflammatory Drug Discovery. In Levin, J and Laufer, S (Ed.), RSC Drug Discovery Series No. 26, p 158-175, the Royal Society of Chemistry, 2012; incorporated by reference in its entirety).

The majority of disclosed MK2 inhibitors are classical type I inhibitors as revealed by crystallographic or biochemical studies. As such, they bind to the ATP site of the kinase and thus compete with intra-cellular ATP (estimated concentration 1 mM-5 mM) to inhibit phosphorylation and activation of the kinase. Representative examples of such small-molecule MK2 inhibitors include, but are not limited to,

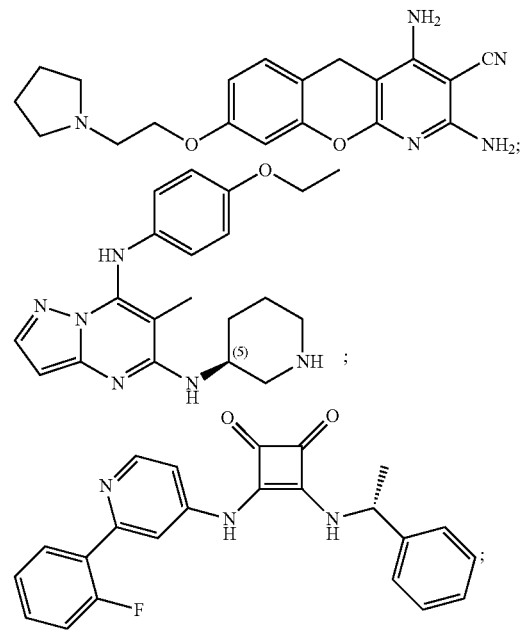

-continued
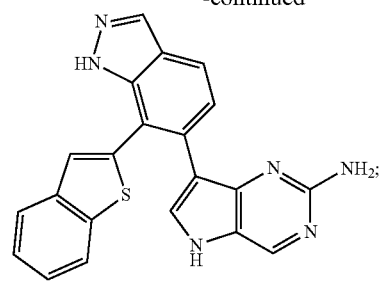
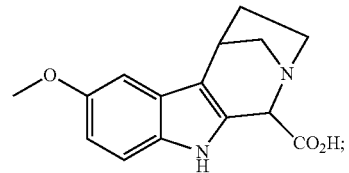
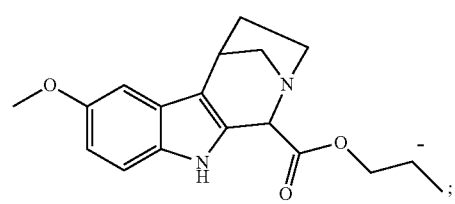
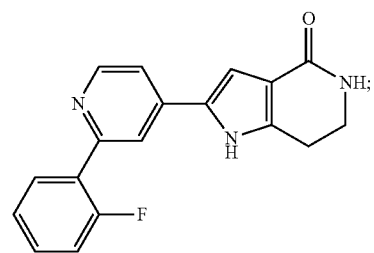
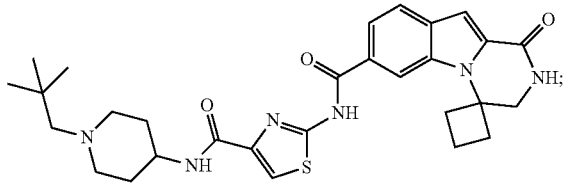
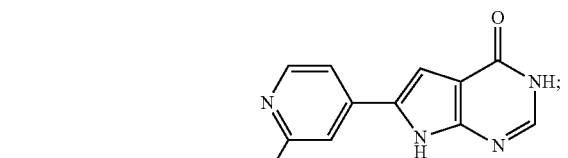
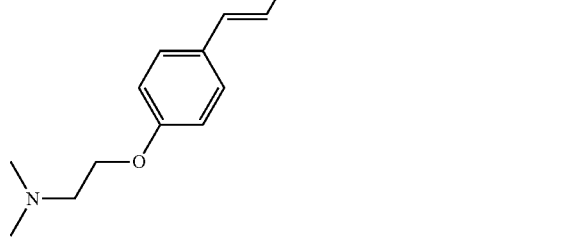
-continued
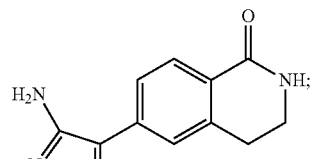
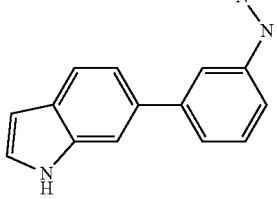
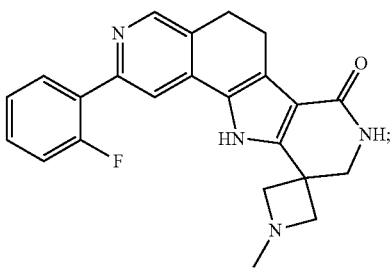
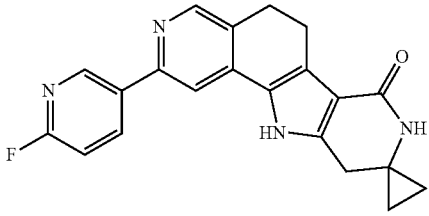
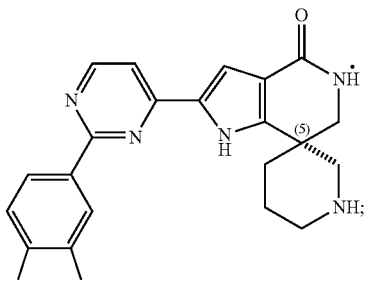
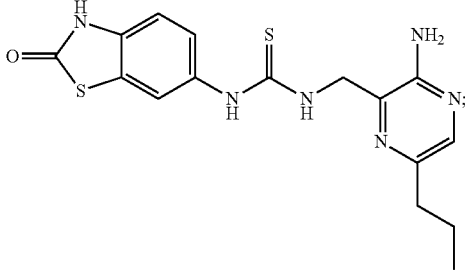
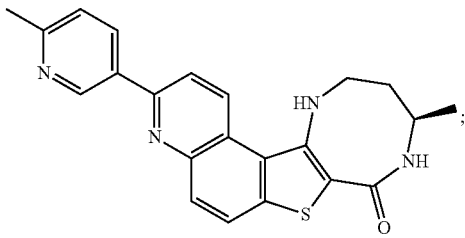

21
-continued
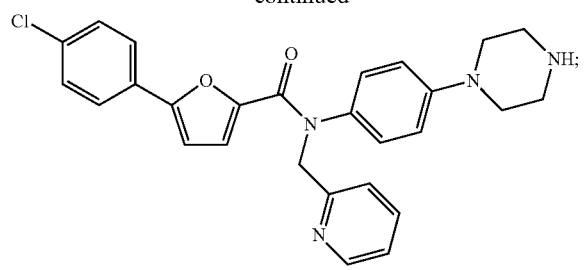
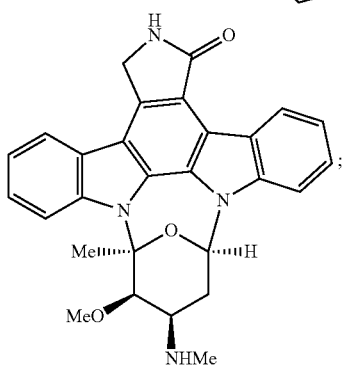
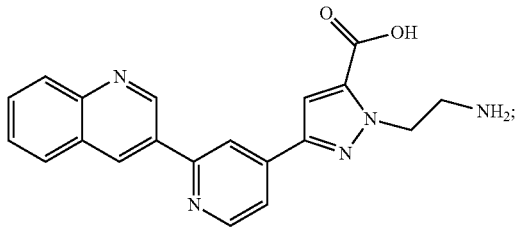
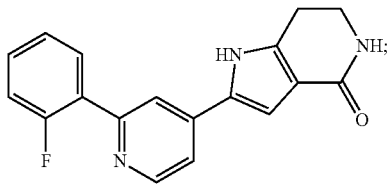
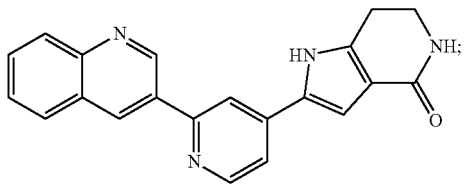
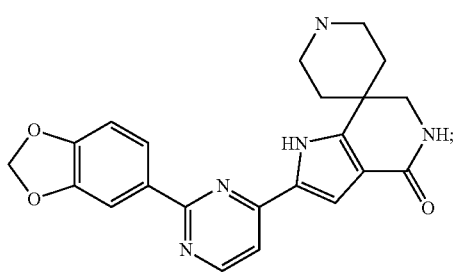
22
-continued
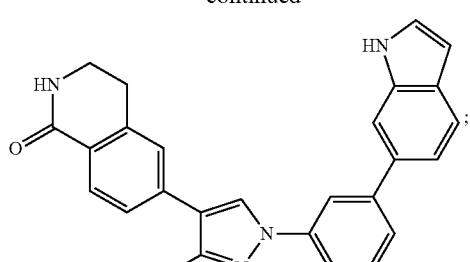
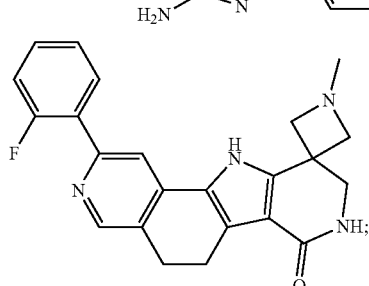
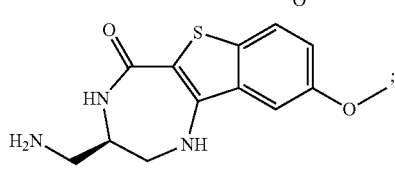
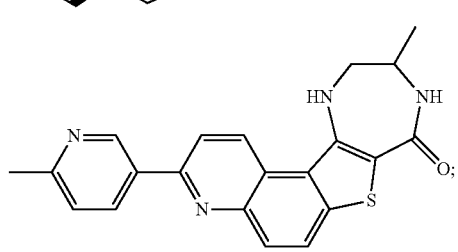
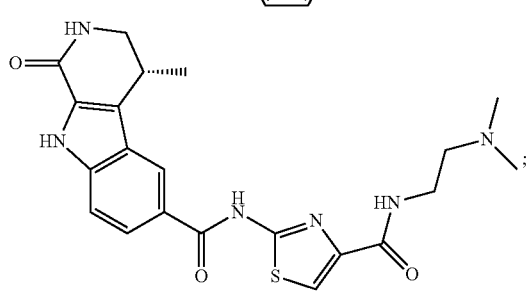
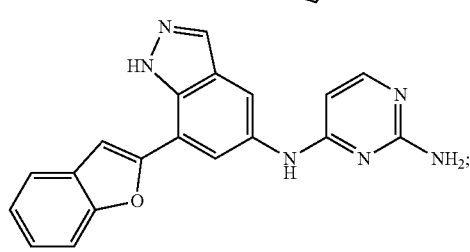
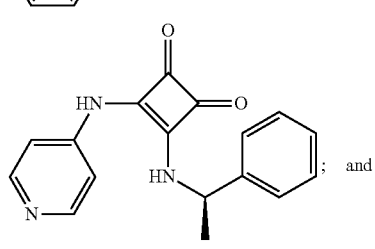; and

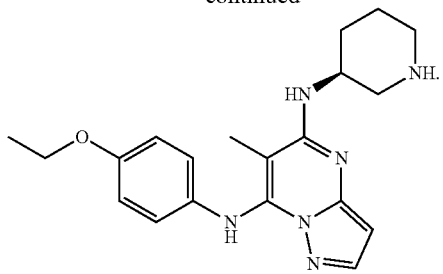

Blocking Peptides

A peptide is a chemical compound composed of a chain of two or more amino acids whereby the carboxyl group of one amino acid in the chain is linked to the amino group of the other via a peptide bond. Peptides have been used inter alia in the study of protein structure and function. Synthetic peptides may be used inter alia as probes to see where protein-peptide interactions occur. Inhibitory peptides may be used inter alia in clinical research to examine the effects of peptides on the inhibition of protein kinases, cancer proteins and other disorders.

The use of several blocking peptides has been studied. For example, extracellular signal-regulated kinase (ERK), a MAPK protein kinase, is essential for cellular proliferation and differentiation. The activation of MAPKs requires a cascade mechanism whereby MAPK is phosphorylated by an upstream MAPKK (MEK) which then, in turn, is phosphorylated by a third kinase MAPKKK (MEKK). The ERK inhibitory peptide functions as a MEK decoy by binding to ERK.

The synthetic peptide autocamtide-2 related inhibitory peptide (AIP), is a highly specific and potent inhibitor of $Ca^{2+}$/calmodulin-dependent protein kinase II (CaMKII). AIP is a non-phosphorylatable analog of autocamtide-2, a highly selective peptide substrate for CaMKII. AIP inhibits CaMKII with an IC50 of 100 nM (IC50 is the concentration of an inhibitor required to obtain 50% inhibition). The AIP inhibition is non-competitive with respect to syntide-2 (CaMKII peptide substrate) and ATP but competitive with respect to autocamtide-2. The inhibition is unaffected by the presence or absence of $Ca^{2+}$/calmodulin. CaMKII activity is inhibited completely by AIP (1 µM) while PKA, PKC and CaMKIV are not affected.

Cell division protein kinase 5 (Cdk5) inhibitory peptide (CIP) is another blocking peptide. Cdk5 phosphorylates the microtubule protein tau at Alzheimer's Disease-specific phospho-epitopes when it associates with p25. p25 is a truncated activator, which is produced from the physiological Cdk5 activator p35 upon exposure to amyloid β peptides. Upon neuronal infections with CIP, CIPs selectively inhibit p25/Cdk5 activity and suppress the aberrant tau phosphorylation in cortical neurons. The reasons for the specificity demonstrated by CIP are not fully understood.

Additional blocking peptides have been studied for inhibiting extracellular-regulated kinase 2 (ERK2), ERK3, p38/HOG1, protein kinase C, casein kinase II, $Ca^{2+}$/calmodulin kinase IV, casein kinase II, Cdk4, Cdk5, DNA-dependent protein kinase (DNA-PK), serine/threonine-protein kinase PAK3, phosphoinositide (PI)-3 kinase, PI-5 kinase, PSTAIRE (the cdk highly conserved sequence), ribosomal S6 kinase, GSK-4, germinal center kinase (GCK), SAPK (stress-activated protein kinase), SEK1 (stress signaling kinase), and focal adhesion kinase (FAK).

Protein Substrate-Competitive Inhibitors

Most of the protein kinase inhibitors developed to date are ATP competitors. This type of molecule competes for the ATP binding site of the kinase and often shows off-target effects due to serious limitations in its specificity. The low specificity of these inhibitors is due to the fact that the ATP binding site is highly conserved among diverse protein kinases. Non-ATP competitive inhibitors, on the other hand, such as substrate competitive inhibitors, are expected to be more specific as the substrate binding sites have a certain degree of variability among the various protein kinases.

Although substrate competitive inhibitors usually have a weak binding interaction with the target enzyme in vitro, studies have shown that chemical modifications can improve the specific biding affinity and the in vivo efficacy of substrate inhibitors (Eldar-Finkelman, H. et al., Biochim, Biophys. Acta, 1804(3):598-603, 2010). In addition, substrate competitive inhibitors show better efficacy in cells than in cell-free conditions in many cases (van Es, J. et al., Curr. Opin. Gent. Dev. 13:28-33, 2003).

In an effort to enhance specificity and potency in protein kinase inhibition, bisubstrate inhibitors also have been developed. Bisubstrate inhibitors, which consist of two conjugated fragments, each targeted to a different binding site of a bisubstrate enzyme, form a special group of protein kinase inhibitors that mimic two natural substrates/ligands and that simultaneously associate with two regions of given kinases. The principle advantage of bisubstrate inhibitors is their ability to generate more interactions with the target enzyme that could result in improved affinity and selectivity of the conjugates, when compared with single-site inhibitors. Examples of bisubstrate inhibitors include, but are not limited to, nucleotide-peptide conjugates, adenosine derivative-peptide conjugates, and conjugates of peptides with potent ATP-competitive inhibitors.

Protein Transduction Domains (PTD)/Cell Permeable Proteins (CPP)

The plasma membrane presents a formidable barrier to the introduction of macromolecules into cells. For nearly all therapeutics to exert their effects, at least one cellular membrane must be traversed. Traditional small molecule pharmaceutical development relies on the chance discovery of membrane permeable molecules with the ability to modulate protein function. Although small molecules remain the dominant therapeutic paradigm, many of these molecules suffer from lack of specificity, side effects, and toxicity. Information-rich macromolecules, which have protein modulatory functions far superior to those of small molecules, can be created using rational drug design based on molecular, cellular, and structural data. However, the plasma membrane is impermeable to most molecules of size greater than 500 Da. Therefore, the ability of cell penetrating peptides, such as the basic domain of Trans-Activator of Transcription (Tat), to cross the cell membrane and deliver macromolecular cargo in vivo, can greatly facilitate the rational design of therapeutic proteins, peptides, and nucleic acids.

Protein transduction domains (PTDs) are a class of peptides capable of penetrating the plasma membrane of mammalian cells and of transporting compounds of many types and molecular weights across the membrane. These compounds include effector molecules, such as proteins, DNA, conjugated peptides, oligonucleotides, and small particles such as liposomes. When PTDs are chemically linked or fused to other proteins, the resulting fusion peptides still are able to enter cells. Although the exact mechanism of transduction is unknown, internalization of these proteins is not believed to be receptor-mediated or transporter-mediated. PTDs are generally 10-16 amino acids in length and may be grouped according to their composition, such as, for example, peptides rich in arginine and/or lysine.

The use of PTDs capable of transporting effector molecules into cells has become increasingly attractive in the design of drugs as they promote the cellular uptake of cargo molecules. These cell-penetrating peptides, generally categorized as amphipathic (meaning having both a polar and a nonpolar end) or cationic (meaning of or relating to or containing net positively charged atoms) depending on their sequence, provide a non-invasive delivery technology for macromolecules. PTDs often are referred to as "Trojan peptides", "membrane translocating sequences", or "cell permeable proteins" (CPPs). PTDs also may be used to assist novel HSPB1 kinase inhibitors to penetrate cell membranes. (see, e.g., U.S. Pat. No. 8,536,303, and U.S. Pat. No. 8,741,849, the contents of each of which are incorporated by reference in their entirety herein).

Viral PTD Containing Proteins

The first proteins to be described as having transduction properties were of viral origin. These proteins still are the most commonly accepted models for PTD action. The HIV-1 Transactivator of Transcription (Tat) and HSV-1 VP 22 protein are the best characterized viral PTD containing proteins.

Tat (HIV-1 trans-activator gene product) is an 86-amino acid polypeptide, which acts as a powerful transcription factor of the integrated HIV-1 genome. Tat acts on the viral genome, stimulating viral replication in latently infected cells. The translocation properties of the Tat protein enable it to activate quiescent infected cells, and it may be involved in priming of uninfected cells for subsequent infection by regulating many cellular genes, including cytokines. The minimal PTD of Tat is the 9 amino acid protein sequence RKKRRQRRR (TAT49-57; SEQ ID NO: 20). Studies utilizing a longer fragment of Tat demonstrated successful transduction of fusion proteins up to 120 kDa. The addition of multiple Tat-PTDs as well as synthetic Tat derivatives has been demonstrated to mediate membrane translocation. Tat PTD containing fusion proteins have been used as therapeutic moieties in experiments involving cancer, transporting a death-protein into cells, and disease models of neurodegenerative disorders.

The mechanism used by transducing peptides to permeate cell membranes has been the subject of considerable interest in recent years, as researchers have sought to understand the biology behind transduction. Early reports that Tat transduction occurred by a nonendocytic mechanism have largely been dismissed as artifactual though other cell-penetrating peptides might be taken up by way of direct membrane disruption. The recent findings that transduction of Tat and other PTDs occurs by way of macropinocytosis, a specialized form of endocytosis, has created a new paradigm in the study of these peptides. Enhanced knowledge of the mechanism of transduction helped improve transduction efficiency with the ultimate goal of clinical success (Snyder E. and Dowdy, S., Pharm Res., 21(3):389-393, 2004).

The current model for Tat-mediated protein transduction is a multistep process that involves binding of Tat to the cell surface, stimulation of macropinocytosis, uptake of Tat and cargo into macropinosomes, and endosomal escape into the cytoplasm. The first step, binding to the cell surface, is thought to be through ubiquitous glycan chains on the cell surface. Stimulation of macropinocytosis by Tat occurs by an unknown mechanism that might include binding to a cell surface protein or might occur by way of proteoglycans or glycolipids. Uptake by way of macropinocytosis, a form of fluid phase endocytosis used by all cell types, is required for Tat and polyarginine transduction. The final step in Tat transduction is escape from macropinosomes into the cytoplasm; this process is likely to be dependent on the pH drop in endosomes that, along with other factors, facilitates a perturbation of the membrane by Tat and release of Tat and its cargo (i.e. peptide, protein or drug etc.) to the cytoplasm (Snyder E. and Dowdy, S., Pharm Res., 21(3):389-393, 2004).

VP22 is the HSV-1 tegument protein, a structural part of the HSV virion. VP22 is capable of receptor independent translocation and accumulates in the nucleus. This property of VP22 classifies the protein as a PTD containing peptide. Fusion proteins comprising full length VP22 have been translocated efficiently across the plasma membrane.

Homeoproteins with Intercellular Translocation Properties

Homeoproteins are highly conserved, transactivating transcription factors involved in morphological processes. They bind to DNA through a specific sequence of 60 amino acids. The DNA-binding homeodomain is the most highly conserved sequence of the homeoprotein. Several homeoproteins have been described as exhibiting PTD-like activity; they are capable of efficient translocation across cell membranes in an energy-independent and endocytosis-independent manner without cell type specificity.

The Antennapedia protein (Antp) is a trans-activating factor capable of translocation across cell membranes; the minimal sequence capable of translocation is a 16 amino acid peptide corresponding to the third helix of the protein's homeodomain (HD). The internalization of this helix occurs at 4° C., suggesting that this process is not endocytosis dependent. Peptides of up to 100 amino acids produced as fusion proteins with AntpHD penetrate cell membranes.

Other homeodomains capable of translocation include Fushi tarazu (Ftz) and Engrailed (En) homeodomain. Many homeodomains share a highly conserved third helix.

Human PTDs

Human PTDs may circumvent potential immunogenicity issues upon introduction into a human patient. Peptides with PTD sequences include: Hoxa-5, Hox-A4, Hox-B5, Hox-B6, Hox-B7, HOX-D3, GAX, MOX-2, and FtzPTD. These proteins all share the sequence found in AntpPTD. Other PTDs include Islet-1, Interleukin-1 (IL-1), Tumor Necrosis Factor (TNF), and the hydrophobic sequence from Kaposi-fibroblast growth factor or Fibroblast Growth Factor-4 (FGF-4) signal peptide, which is capable of energy-, receptor-, and endocytosis-independent translocation. Unconfirmed PTDs include members of the Fibroblast Growth Factor (FGF) family. FGFs are polypeptide growth factors that regulate proliferation and differentiation of a wide variety of cells. Several publications have reported that basic fibroblast growth factor (FGF-2) exhibits an unconventional internalization similar to that of VP-22, Tat, and homeodomains. It has also been reported that acidic FGF (FGF-1) translocated cell membranes at temperatures as low as 4° C. However, no conclusive evidence exists about the domain responsible for internalization or the translocation properties of fusion proteins (Beerens, A. et al., Curr Gene Ther., 3(5):486-494, 2003).

Synthetic PTDs

Several peptides have been synthesized in an attempt to create more potent PTDs and to elucidate the mechanisms by which PTDs transport proteins across cell membranes. Many of these synthetic PTDs are based on existing and well documented peptides, while others are selected for their basic residues and/or positive charges, which are thought to be crucial for PTD function. A few of these synthetic PTDs showed better translocation properties than the existing ones (Beerens, A. et al., Curr Gene Ther., 3(5):486-494, 2003). Exemplary Tat-derived synthetic PTDs include, for example, but are not limited to, WLRRIKAWLRRIKA (SEQ ID NO: 12); WLRRIKA (SEQ ID NO: 13); YGRKKRRQRRR (SEQ ID NO: 14); WLRRIKAWLRRI (SEQ ID NO: 15); FAKLAARLYR (SEQ ID NO: 16); KAFAKLAARLYR (SEQ ID NO: 17); and HRRIKAWLKKI (SEQ ID NO: 18).

Compositions Comprising PTDs Fused to MK2 Inhibitor Peptide Therapeutic Domains (TD)

Several MK2 inhibitor peptides (TD) have been synthesized, fused to synthetic PTDs and the use of compositions comprising these fused polypeptides has been studied. These polypeptides include, but are not limited to, YARAAARQARAKALARQLGVAA (SEQ ID NO: 1; MMI-0100), YARAAARQARAKALNRQLGVA (SEQ ID NO: 19; MMI-0200), FAKLAARLYRKALARQLGVAA (SEQ ID NO: 3; MMI-0300), KAFAKLAARLYRKALARQLGVAA (SEQ ID NO: 4; MMI-0400), HRRIKAWLKKIKALARQLGVAA (SEQ ID NO: 7; MMI-0500), YARAAARDARAKALNRQLAVAA (SEQ ID NO: 23; MMI-0600), and YARAAARQARAKALNRQLAVA (SEQ ID NO: 24; MMI-0600-2). Both in vitro and in vivo studies have shown that these polypeptides can be useful in the treatment of various diseases, disorders and conditions. These include, without limitation, hyperplasia and neoplasm (U.S. Pat. Nos. 8,536,303 and 8,741,849) inflammatory disorders (U.S. application Ser. No. 12/634,476 and U.S. application Ser. No. 13/934,933), adhesions (U.S. application Ser. No. 12/582,516), failure of a vascular graft due to neospasm (U.S. application Ser. No. 13/114,872), improving neurite outgrowth (U.S. application Ser. No. 12/844,815), cutaneous scarring (U.S. application Ser. No. 13/829,876), coronary artery bypass vascular graft failure (U.S. application Ser. No. 13/700,087) and interstitial lung disease and pulmonary fibrosis (U.S. application Ser. No. 13/445,759).

Peptide compositions present a number of particular challenges to formulation scientists (R. W. Payne and M. C. Manning, "Peptide formulation: challenges and strategies," Innovations in Pharmaceutical Technology, 64-68 (2009)). First, since peptides do not have a globular structure that can sequester reactive groups, the side chains of nearly all residues in a peptide are fully solvent exposed, and can exhibit chemical degradation through hydrolytic reactions, for example, oxidation and deamidation. Second, the conformation in aqueous solution may have little similarity to the structure found when bound to a receptor. Third, many peptides tend to be monomeric at very low concentration, but may self-assemble as the concentration is increased and behave as if in a highly associated state, but these structures are too transient or fluxional to provide any increase in long-term stability. Fourth, the propensity of peptides to self-associate is connected with their physical instability, meaning their likelihood of forming aggregates. Moreover, excipients present in a peptide formulation can chemically degrade, interact with various surfaces during manufacturing, interact with the container or closure, or interact with the peptide itself, thereby negatively affecting critical properties of the preparation (Lars Hovgaard, and Sven Frokjaer, "Pharmaceutical Formulation Development of Peptides and Proteins, $2^{nd}$ Ed., CRC Press (2012) pp. 212-213).

TrkB is Highly Expressed in NSCLC

Aberrant regulation in the invasion of cancer cells is closely associated with their metastatic potential. (Zhang, S. et al., "TrkB is highly expressed in NSCLC and mediates BDNF-induced activation of Pyk2 signaling and the invasion of A549 cells," BMC Cancer 2010, 10: 43). Tropomysin-related kinase B (TrkB), a member of the Trk family, functions as a receptor tyrosine kinase and is considered to facilitate tumor metastasis. Id. Brain-derived neurotrophic factor (BDNF), the primary ligand binding to TrkB, results in the regulation of various cellular activities in neuroblastoma, such as cell differentiation, apoptosis, and invasion. Id. TrkB is up-regulated in a variety of primary human tumors, including neuroblastoma and ovarian cancer. Id. Enhanced TrkB signaling promotes cell survival in an anchorage dependent manner. Id. When activated by BDNF, TrkB leads to the activation of downstream signaling molecules, such as phosphoinositide-3 kinase/protein kinase B (PI3K/Akt), which induces the differential regulation of apoptosis and metastasis. Id.

Proline-rich tyrosine kinase 2 (Pyk2) is an extensively expressed non-receptor tyrosine kinase that integrates signals from receptor tyrosine kinases and intracellular signaling molecules in such essential cellular processes as cell differentiation, proliferation and migration. Id. Pyk2 is rapidly tyrosine phosphorylated in response to various extracellular signals, and activated Pyk2 signaling promotes cell survival and migration in an anchorage-independent manner. Id. The tyrosine 402 (Tyr402) of Pyk2 serves as the primary autophosphorylation site essential for Pyk2 activity and function. Id. High activity of Tyr402 is found in tumor cells with a more invasive and metastatic phenotype. Id.

High expression of TrkB has been reported in NSCLC, particularly correlated with lymph node metastasis and TNM stage. Id. TrkB-siRNA interrupted BDNF-promoted Pyk2 and extracellular regulating kinase (ERK) activation and invasion of lung adenocarcinoma A549 cells. Id. Moreover, Pyk2-siRNA inhibited BDNF-associated ERK phosphorylation and cell invastion. Id. The investigators considered these data as evidence that TrkB/Pyk2/ERK signaling mediates BDNF-induced invasion of A549 cells, and suggested that suppression of TrkB may provide a helpful target for inhibitory therapies of metastasis in NSCLC. Id.

The described invention offers an approach to treat non-small cell lung carcinoma using cell-penetrating, peptide-based inhibitors of MK2, that may be effective to overcome tumor chemoresistance, to enhance tumor chemosensitivity and to slow progression of the non-small cell lung cancer solid tumor comprising the population of tumor cells.

SUMMARY OF THE INVENTION

According to one aspect, the described invention provides a pharmaceutical composition for use in treating a non-small cell lung cancer (NSCLC) solid tumor comprising a population of tumor cells, wherein the pharmaceutical composition comprises a therapeutic amount of a polypeptide of the amino acid sequence YARAAARQARAKALARQLGVAA (SEQ ID NO: 1) or a functional equivalent thereof, and a pharmaceutically acceptable carrier thereof, and wherein the therapeutic amount is effective to inhibit a kinase activity of a kinase selected from the group listed in Table 1 in the population of tumor cells and to reduce cancer cell proliferation, to reduce tumor size, to reduce tumor burden, to induce tumor cell death, to overcome tumor chemoresistance, to enhance tumor chemosensitivity, to slow progression of the population of tumor cells, or a combination thereof.

According to another aspect, the described invention provides a method for treating non-small cell lung cancer solid tumor comprising a population of tumor cells, the method comprising: administering to a subject in need thereof a pharmaceutical composition comprising a therapeutic amount of a polypeptide of the amino acid sequence YARAAARQARAKALARQLGVAA (SEQ ID NO: 1) or a functional equivalent thereof, and a pharmaceutically acceptable carrier thereof, wherein therapeutic amount of the polypeptide is effective to inhibit kinase activity of the population of tumor cells, to reduce cancer cell proliferation, to reduce tumor size, to reduce tumor burden, to induce cancer cell death, to overcome tumor chemoresistance, to enhance tumor chemosensitivity, to slow progression of the population of tumor cells, or a combination thereof.

According to another aspect, the described invention provides a system for the treatment of a non-small cell lung cancer (NSCLC) tumor comprising a population of tumor cells comprising: (a) a pharmaceutical composition, wherein the pharmaceutical composition comprises a therapeutic amount of a polypeptide of the amino acid sequence YARAAARQARAKALARQLGVAA (SEQ ID NO: 1) or a functional equivalent thereof, and a pharmaceutically acceptable carrier thereof, and wherein therapeutic amount may be effective to inhibit a kinase activity of a kinase selected from the group listed in Table 1 in the population of tumor cells and to reduce proliferation of the population of tumor cells, to reduce tumor size, to reduce tumor burden, to induce tumor cell death, to overcome tumor chemoresistance, to enhance tumor chemosensitivity, to slow progression of the population of tumor cells, or a combination thereof; and (b) an inhalation device for pulmonary delivery.

According to one embodiment, the tumor is selected from the group consisting of a primary tumor, a secondary tumor, a recurrent tumor, a refractory tumor and a combination thereof. According to another embodiment, the primary tumor is selected from the group consisting of a squamous cell carcinoma, an adenocarcinoma, a large cell carcinoma and a combination thereof. According to another embodiment, the secondary tumor is a metastatic tumor. According to another embodiment, the metastatic tumor is a selected from the group consisting of an adrenal metastatic tumor, a bone metastatic tumor, a liver metastatic tumor, a brain metastatic tumor and a combination thereof.

According to some embodiments, the step of administering occurs intratracheally, (e.g., by inhalation), parenterally, intravenously, or intraperitoneally. According to some embodiments, the step of administering occurs by pulmonary administration.

According to one embodiment, the pharmaceutical composition further comprises at least one additional therapeutic agent. According to another embodiment, the additional therapeutic agent is a chemotherapeutic agent selected from the group consisting of Abitrexate (Methotrexate), Abraxane (Paclitaxel Albumin-stabilized Nanoparticle Formulation), Afatinib Dimaleate, Alimta (Pemetrexed Disodium), Avastin (Bevacizumab), Bvacizumab, Carboplatin, Ceritinib, Cisplatin, Crizotinib, Cyramza (Ramucirumab), Docetaxel, Erlotinib Hydrochloride, Folex PFS (Methotrexate), Gefitinib, Gilotrif (Afatinib Dmaleate), Gemcitabine Hydrochloride, Gemzar (Gemcitabine Hydrochloride), Iressa (Gefitinib), Mechlorethamine Hydrochloride, Methotrexate, Methotrexate LPF (Methotrexate), Mexate (Methotrexate), Mexate-AQ (Methotrexate), Mustargen (mechlorethamine Hydrochloride), Navelbine (Vinorelbine Tartrate), Paclitaxel, Paclitaxel Albumin-stabilized nanoparticle Formulation, Paraplat (Carboplatin), Paraplatin (Carboplatin), Pemetrexed Disodium, Platinol (Cisplatin), Platinol-AQ (Cisplatin), Ramucirumab, Tarceva (Erlotinib Hydrochloride), Taxol (Paclitaxel), Taxotere (Docetaxel), Vinorelbine Tartrate, Xalkori (Crizotinib), Zykadia (Ceritinib), Carboplatin-Taxol, Gemcitabine-Cisplatin and a combination thereof. According to another embodiment, the additional therapeutic agent is a glucocorticoid selected from the group consisting of prednisone, budesonide, mometasone furoate, fluticasone propionate, fluticasone furoate, and a combination thereof. According to another embodiment, the additional therapeutic agent is a bronchodilator selected from the group consisting of a leukotriene modifer, an anticholinergic bronchodilator, a short-acting β2-agonist, and long-acting β2-agonist, and a combination thereof. According to another embodiment, the additional therapeutic agent is an analgesic agent. According to another embodiment, the additional therapeutic agent is an anti-infective agent.

According to one embodiment, the functional equivalent of the polypeptide YARAAARQARAKALARQLGVAA (SEQ ID NO: 1) is of amino acid sequence FAKLAARLYRKALARQLGVAA (SEQ ID NO: 3). According to another embodiment, the functional equivalent of the polypeptide YARAAARQARAKALARQLGVAA (SEQ ID NO: 1) is of amino acid sequence KAFAKLAARLYRKALARQLGVAA (SEQ ID NO: 4). According to another embodiment, the functional equivalent of the polypeptide YARAAARQARAKALARQLGVAA (SEQ ID NO: 1) is of amino acid sequence YARAAARQARAKALARQLAVA (SEQ ID NO: 5). According to another embodiment, the functional equivalent of the polypeptide YARAAARQARAKALARQLGVAA (SEQ ID NO: 1) is of amino acid sequence YARAAARQARAKALARQLGVA (SEQ ID NO: 6). According to another embodiment, the functional equivalent of the polypeptide YARAAARQARAKALARQLGVAA (SEQ ID NO: 1) is of amino acid sequence HRRIKAWLKKIKALARQLGVAA (SEQ ID NO: 7).

According to one embodiment, therapeutic domain (TD) of the functional equivalent of the polypeptide YARAAARQARAKALARQLGVAA (SEQ ID NO: 1) is made from the fusion of the first polypeptide that is the cell penetrating peptide (CPP) operatively linked to the second polypeptide that is therapeutic domain (TD), is a polypeptide whose sequence has a substantial identity to amino acid sequence KALARQLGVAA (SEQ ID NO: 2). According to another embodiment, the second polypeptide is a polypeptide of amino acid sequence KALARQLAVA (SEQ ID NO: 8). According to another embodiment, the second polypeptide is a polypeptide of amino acid sequence KALARQLGVA (SEQ ID NO: 9). According to another embodiment, the second polypeptide is a polypeptide of amino acid sequence KALARQLGVAA (SEQ ID NO: 10).

According to one embodiment, the functional equivalent of the polypeptide YARAAARQARAKALARQLGVAA (SEQ ID NO: 1) is a fusion protein comprising a first polypeptide operatively linked to a second polypeptide, wherein the first polypeptide is a cell penetrating peptide functionally equivalent to YARAAARQARA (SEQ ID NO: 11) selected from the group consisting of a polypeptide of amino acid sequence WLRRIKAWLRRIKA (SEQ ID NO: 12), WLRRIKA (SEQ ID NO: 13), YGRKKRRQRRR (SEQ ID NO: 14), WLRRIKAWLRRI (SEQ ID NO: 15), FAKLAARLYR (SEQ ID NO: 16), KAFAKLAARLYR (SEQ ID NO: 17) and HRRIKAWLKKI (SEQ ID NO: 18), and the second polypeptide is of amino acid sequence KALARQLGVAA (SEQ ID NO: 2). According to another embodiment, the first polypeptide is a polypeptide of amino acid sequence WLRRIKAWLRRIKA (SEQ ID NO: 12). According to another embodiment, the first polypeptide is a polypeptide of amino acid sequence WLRRIKA (SEQ ID NO: 13).

According to another embodiment, the first polypeptide is a polypeptide of amino acid sequence YGRKKRRQRRR (SEQ ID NO: 14). According to another embodiment, the first polypeptide is a polypeptide of amino acid sequence WLRRIKAWLRRI (SEQ ID NO: 15). According to another embodiment, the first polypeptide is a polypeptide of amino acid sequence FAKLAARLYR (SEQ ID NO: 16). According to another embodiment, the first polypeptide is a polypeptide of amino acid sequence KAFAKLAARLYR (SEQ ID NO: 17). According to another embodiment, the first polypeptide is a polypeptide of amino acid sequence HRRIKAWLKKI (SEQ ID NO: 18).

According to one embodiment, the carrier is selected from the group consisting of a controlled release carrier, a delayed release carrier, a sustained release carrier, and a long-term release carrier.

According to one embodiment, the pharmaceutical composition is in a form of a dry powder. According to another embodiment, the dry powder comprises microparticles with Mass Median Aerodynamic Diameter (MMAD) of 1 to 5 microns.

According to one embodiment, the pharmaceutical composition is administered via an inhalation device. According to another embodiment, the inhalation device is a nebulizer. According to another embodiment, the inhalation device is a metered-dose inhaler (MDI). According to another embodiment, the inhalation device is a dry powder inhaler (DPI). According to another embodiment, the inhalation device is a dry powder nebulizer.

BRIEF DESCRIPTION OF THE DRAWINGS

FIG. 1 shows delivery performance of neat spray-dried insulin.

FIG. 2 shows particle size distribution of spray-dried insulin, which is determined by Anderson Cascade Impaction (ACI).

FIG. 3 shows efficiency and flow rate comparison of MicroDose Dry Powder Inhaler (DPI) vs. two marketed "passive" Dry Powder Inhalers (DPIs).

FIG. 4 shows flow-rate independence of spray-dried neat peptide.

Figure 5:
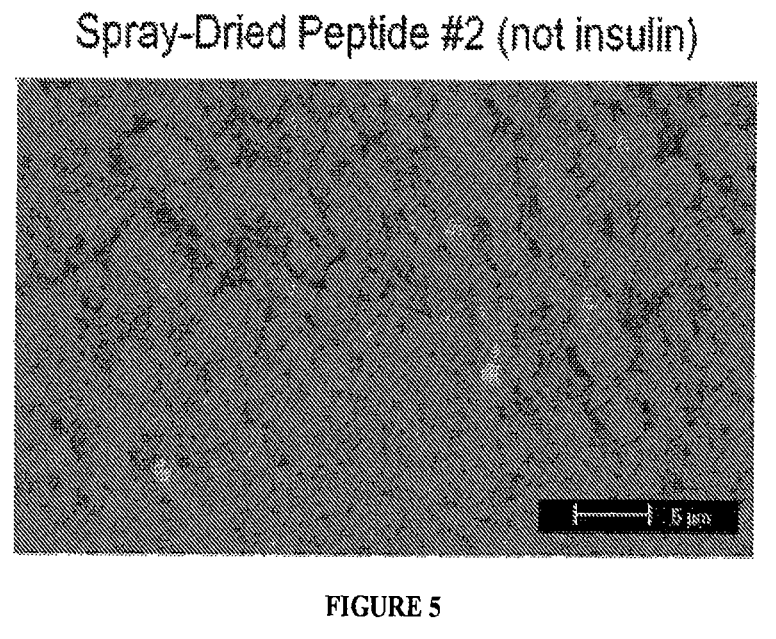

FIG. 5 shows a representative micrograph of a spray-dried peptide (not insulin).

FIG. 6 shows particle size distribution of a spray-dried peptide (not insulin).

FIG. 7 shows particle size distribution of micronized/lactose blend combination, which is determined by Next Generation Impactor (NGI)

FIG. 8 shows delivery performance of micronized small molecule (long-acting muscarinic agents (LAMA)/lactose blend).

DETAILED DESCRIPTION OF THE INVENTION

The described invention provides a composition and method for treating non-small cell lung carcinoma in a subject in need of thereof, the method comprising administering a therapeutic amount of a composition comprising a polypeptide having the amino acid sequence YARAAARQARAKALARQLGVAA (MMI-0100; SEQ ID NO: 1) or a functional equivalent thereof.

Glossary

The term "addition" as used herein refers to the insertion of one or more bases, or of one or more amino acids, into a sequence.

The term "administer" as used herein refers to dispensing, supplying, applying, giving, apportioning or contributing. The terms "administering" or "administration" are used interchangeably and include in vivo administration, as well as administration directly to tissue ex vivo. Generally, compositions may be administered systemically either orally, buccally, parenterally, topically, by inhalation or insufflation (i.e., through the mouth or through the nose), or rectally in dosage unit formulations containing the conventional nontoxic pharmaceutically acceptable carriers, adjuvants, and vehicles as desired, or may be locally administered by means such as, but not limited to, injection, implantation, grafting, topical application, or parenterally. Additional administration may be performed, for example, intravenously, pericardially, orally, via implant, transmucosally, transdermally, topically, intramuscularly, subcutaneously, intraperitoneally, intrathecally, intralymphatically, intralesionally, or epidurally. Administering can be performed, for example, once, a plurality of times, and/or over one or more extended periods.

The term "adjunct therapy" as used herein refers to another treatment used together with the primary treatment.

The term "airway" as used herein refers to the passages through which air enters and leaves the body. The pulmonary airway comprises those parts of the respiratory tract through which air passes during breathing.

The term "airway obstruction" as used herein refers to any abnormal reduction in airflow. Resistance to airflow can occur anywhere in the airway from the upper airway to the terminal bronchi.

The term "alveolus" or "alveoli" as used herein refers to an anatomical structure that has the form of a hollow cavity. Found in the lung, the pulmonary alveoli are spherical outcroppings of the respiratory sites of gas exchange with the blood. The alveoli contain some collagen and elastic fibers. Elastic fibers allow the alveoli to stretch as they fill with air when breathing in. They then spring back during breathing out in order to expel the carbon dioxide-rich air.

The terms "amino acid residue" or "amino acid" or "residue" are used interchangeably to refer to an amino acid that is incorporated into a protein, a polypeptide, or a peptide, including, but not limited to, a naturally occurring amino acid and known analogs of natural amino acids that can function in a similar manner as naturally occurring amino acids. The amino acids may be L- or D-amino acids. An amino acid may be replaced by a synthetic amino acid, which is altered so as to increase the half-life of the peptide, increase the potency of the peptide, or increase the bioavailability of the peptide.

The single letter designation for amino acids is used predominately herein. As is well known by one of skill in the art, such single letter designations are as follows:

A is alanine; C is cysteine; D is aspartic acid; E is glutamic acid; F is phenylalanine; G is glycine; H is histidine; I is isoleucine; K is lysine; L is leucine; M is methionine; N is asparagine; P is proline; Q is glutamine; R is arginine; S is serine; T is threonine; V is valine; W is tryptophan; and Y is tyrosine.

The following represents groups of amino acids that are conservative substitutions for one another: 1) Alanine (A), Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

The terms "apoptosis" or "programmed cell death" refer to a highly regulated and active process that contributes to biologic homeostasis comprised of a series of biochemical events that lead to a variety of morphological changes, including blebbing, changes to the cell membrane, such as loss of membrane asymmetry and attachment, cell shrinkage, nuclear fragmentation, chromatin condensation, and chromosomal DNA fragmentation, without damaging the organism.

Apoptotic cell death is induced by many different factors and involves numerous signaling pathways, some dependent on caspase proteases (a class of cysteine proteases) and others that are caspase independent. It can be triggered by many different cellular stimuli, including cell surface receptors, mitochondrial response to stress, and cytotoxic T cells, resulting in activation of apoptotic signaling pathways The caspases involved in apoptosis convey the apoptotic signal in a proteolytic cascade, with caspases cleaving and activating other caspases that then degrade other cellular targets that lead to cell death. The caspases at the upper end of the cascade include caspase-8 and caspase-9. Caspase-8 is the initial caspase involved in response to receptors with a death domain (DD) like Fas.

Receptors in the TNF receptor family are associated with the induction of apoptosis, as well as inflammatory signaling. The Fas receptor (CD95) mediates apoptotic signaling by Fas-ligand expressed on the surface of other cells. The Fas-FasL interaction plays an important role in the immune system and lack of this system leads to autoimmunity, indicating that Fas-mediated apoptosis removes self-reactive lymphocytes. Fas signaling also is involved in immune surveillance to remove transformed cells and virus infected cells. Binding of Fas to oligimerized FasL on another cell activates apoptotic signaling through a cytoplasmic domain termed the death domain (DD) that interacts with signaling adaptors including FAF, FADD and DAX to activate the caspase proteolytic cascade. Caspase-8 and caspase-10 first are activated to then cleave and activate downstream caspases and a variety of cellular substrates that lead to cell death.

Mitochondria participate in apoptotic signaling pathways through the release of mitochondrial proteins into the cytoplasm. Cytochrome c, a key protein in electron transport, is released from mitochondria in response to apoptotic signals, and activates Apaf-1, a protease released from mitochondria. Activated Apaf-1 activates caspase-9 and the rest of the caspase pathway. Smac/DIABLO is released from mitochondria and inhibits IAP proteins that normally interact with caspase-9 to inhibit apoptosis. Apoptosis regulation by Bcl-2 family proteins occurs as family members form complexes that enter the mitochondrial membrane, regulating the release of cytochrome c and other proteins. TNF family receptors that cause apoptosis directly activate the caspase cascade, but can also activate Bid, a Bcl-2 family member, which activates mitochondria-mediated apoptosis. Bax, another Bcl-2 family member, is activated by this pathway to localize to the mitochondrial membrane and increase its permeability, releasing cytochrome c and other mitochondrial proteins. Bcl-2 and Bcl-xL prevent pore formation, blocking apoptosis. Like cytochrome c, AIF (apoptosis-inducing factor) is a protein found in mitochondria that is released from mitochondria by apoptotic stimuli. While cytochrome C is linked to caspase-dependent apoptotic signaling, AIF release stimulates caspase-independent apoptosis, moving into the nucleus where it binds DNA. DNA binding by AIF stimulates chromatin condensation, and DNA fragmentation, perhaps through recruitment of nucleases.

The mitochondrial stress pathway begins with the release of cytochrome c from mitochondria, which then interacts with Apaf-1, causing self-cleavage and activation of caspase-9. Caspase-3, -6 and -7 are downstream caspases that are activated by the upstream proteases and act themselves to cleave cellular targets.

Granzyme B and perforin proteins released by cytotoxic T cells induce apoptosis in target cells, forming transmembrane pores, and triggering apoptosis, perhaps through cleavage of caspases, although caspase-independent mechanisms of Granzyme B mediated apoptosis have been suggested.

Fragmentation of the nuclear genome by multiple nucleases activated by apoptotic signaling pathways to create a nucleosomal ladder is a cellular response characteristic of apoptosis. One nuclease involved in apoptosis is DNA fragmentation factor (DFF), a caspase-activated DNAse (CAD). DFF/CAD is activated through cleavage of its associated inhibitor ICAD by caspases proteases during apoptosis. DFF/CAD interacts with chromatin components such as topoisomerase II and histone H1 to condense chromatin structure and perhaps recruit CAD to chromatin. Another apoptosis activated protease is endonuclease G (EndoG). EndoG is encoded in the nuclear genome but is localized to mitochondria in normal cells. EndoG may play a role in the replication of the mitochondrial genome, as well as in apoptosis. Apoptotic signaling causes the release of EndoG from mitochondria. The EndoG and DFF/CAD pathways are independent since the EndoG pathway still occurs in cells lacking DFF.

Hypoxia, as well as hypoxia followed by reoxygenation can trigger cytochrome c release and apoptosis. Glycogen synthase kinase (GSK-3) a serine-threonine kinase ubiquitously expressed in most cell types, appears to mediate or potentiate apoptosis due to many stimuli that activate the mitochondrial cell death pathway. Loberg, R D, et al., J. Biol. Chem. 277 (44): 41667-673 (2002). It has been demonstrated to induce caspase 3 activation and to activate the proapoptotic tumor suppressor gene p53. It also has been suggested that GSK-3 promotes activation and translocation of the proapoptotic Bcl-2 family member, Bax, which, upon agregation and mitochondrial localization, induces cytochrome c release. Akt is a critical regulator of GSK-3, and phosphorylation and inactivation of GSK-3 may mediate some of the antiapoptotic effects of Akt.

The term "Body Condition Scoring" or "BCS" as used herein refers to a non-invasive method for assessing health and establishing endpoints for adult animals where body weight is not a viable monitoring tool, such as with animal tumor models, animal ascites production and animal pregnancy, or for young growing animals. BCS is determined by frequent visual and hands-on examination of each animal. A score of BC1=mouse is emaciated: skeletal structure extremely prominent, little or no flesh cover, vertebrae distinctly segmented. A score of BC2=mouse is underconditioned: segmentation of vertebral column evident, dorsal pelvic bones are readily palpable. A score of BC3=mouse is well-conditioned: vertebrae and dorsal pelvis not prominent, palpable with slight pressure. A score of BC4=mouse is overconditioned: spine is a continuous column, vertebrae palpable only with firm pressure. A score of BC5=mouse is obese: mouse is smooth and bulky, bone structure disappears under flesh and subcutaneous fat.

The term "bronchoalveolar lavage" or "BAL" as used herein refers to a medical procedure in which a bronchoscope is passed through the mouth or nose into the lungs and fluid is squirted into a small part of the lung and then recollected for examination. BAL typically is performed to diagnose lung disease. BAL commonly is used to diagnose infections in people with immune system problems, pneumonia in people on ventilators, some types of lung cancer, and scarring of the lung (interstitial lung disease). BAL is the most common manner to sample the components of the epithelial lining fluid (ELF) and to determine the protein composition of the pulmonary airways, and is often used in immunological research as a means of sampling cells or pathogen levels in the lung.

The terms "cancer" or "malignancy" as used herein refer to diseases in which abnormal cells divide without control and can invade nearby tissues. Cancer cells also can spread to other parts of the body through the blood and lymph systems.

The terms "carrier" and "pharmaceutical carrier" as used herein refer to a pharmaceutically acceptable inert agent or vehicle for delivering one or more active agents to a subject, and often is referred to as "excipient." The (pharmaceutical) carrier must be of sufficiently high purity and of sufficiently low toxicity to render it suitable for administration to the subject being treated. The (pharmaceutical) carrier further should maintain the stability and bioavailability of an active agent, e.g., a polypeptide of the described invention. The (pharmaceutical) carrier can be liquid or solid and is selected, with the planned manner of administration in mind, to provide for the desired bulk, consistency, etc., when combined with an active agent and other components of a given composition. The (pharmaceutical) carrier may be, without limitation, a binding agent (e.g., pregelatinized maize starch, polyvinylpyrrolidone or hydroxypropyl methylcellulose, etc.), a filler (e.g., lactose and other sugars, microcrystalline cellulose, pectin, gelatin, calcium sulfate, ethyl cellulose, polyacrylates, calcium hydrogen phosphate, etc.), a lubricant (e.g., magnesium stearate, talc, silica, colloidal silicon dioxide, stearic acid, metallic stearates, hydrogenated vegetable oils, corn starch, polyethylene glycols, sodium benzoate, sodium acetate, etc.), a disintegrant (e.g., starch, sodium starch glycolate, etc.), or a wetting agent (e.g., sodium lauryl sulphate, etc.). Other suitable (pharmaceutical) carriers for the compositions of the described invention include, but are not limited to, water, salt solutions, alcohols, polyethylene glycols, gelatins, amyloses, magnesium stearates, talcs, silicic acids, viscous paraffins, hydroxymethylcelluloses, polyvinylpyrrolidones and the like. Compositions that are for parenteral administration of a polypeptide of the described invention may include (pharmaceutical) carriers such as sterile aqueous solutions, non-aqueous solutions in common solvents such as alcohols, or solutions of the polypeptide in a liquid oil base.

The term "cell" is used herein to refer to the structural and functional unit of living organisms and is the smallest unit of an organism classified as living.

The term "cell line" as used herein refers to an immortalized cell, which have undergone transformation and can be passed indefinitely in culture.

The term "cell penetrating peptide" (also referred to as "CPP," "protein transduction domain," "PTD", "Trojan peptide", "membrane translocating sequence", and "cell permeable protein") as used herein refers to a class of peptides generally capable of penetrating the plasma membrane of mammalian cells. It also refers to a peptide, peptide segment, or variant or derivative thereof, with substantial identity to peptide YARAAARQARA (SEQ ID NO: 11), or a functional segment thereof, and to a peptide, peptide segment, or variant or derivative thereof, which is functionally equivalent to SEQ ID NO: 11. CPPs generally are 10-16 amino acids in length and are capable of transporting compounds of many types and molecular weights across mammalian cells. Such compounds include, but are not limited to, effector molecules, such as proteins, DNA, conjugated peptides, oligonucleotides, and small particles such as liposomes. CPPs chemically linked or fused to other proteins ("fusion proteins") still are able to penetrate the plasma membrane and enter cells.

The term "chemoresistance" as used herein refers to the development of a cell phenotype resistant to a variety of structurally and functionally distinct agents. Tumors can be intrinsically resistant prior to chemotherapy, or resistance may be acquired during treatment by tumors that are initially sensitive to chemotherapy. Drug resistance is a multifactorial phenomenon involving multiple interrelated or independent mechanisms. A heterogeneous expression of involved mechanisms may characterize tumors of the same type or cells of the same tumor and may at least in part reflect tumor progression. Exemplary mechanisms that can contribute to cellular resistance include: increased expression of defense factors involved in reducing intracellular drug concentration; alterations in drug-target interaction; changes in cellular response, in particular increased cell ability to repair DNA damage or tolerate stress conditions, and defects in apoptotic pathways.

The term "chemosensitive", "chemosensitivity" or "chemosensitive tumor" as used herein refers to a tumor that is responsive to a chemotherapy or a chemotherapeutic agent. Characteristics of a chemosensitive tumor include, but are not limit to, reduced proliferation of the population of tumor cells, reduced tumor size, reduced tumor burden, tumor cell death, and slowed/inhibited progression of the population of tumor cells.

The term "chemotherapeutic agent" as used herein refers to chemicals useful in the treatment or control of a disease.

The term "chemotherapy" as used herein refers to a course of treatment with one or more chemotherapeutic agent.

The term "chemotherapy regimen" ("combination chemotherapy") means chemotherapy with more than one drug in order to benefit from the dissimilar toxicities of the more than one drug. A principle of combination cancer therapy is that different drugs work through different cytotoxic mechanisms; since they have different dose-limiting adverse effects, they can be given together at full doses.

The term "condition" as used herein refers to a variety of health states and is meant to include disorders or diseases caused by any underlying mechanism, disorder, or injury.

The term "contact" and all its grammatical forms as used herein refers to a state or condition of touching or of immediate or local proximity.

The term "controlled release" as used herein refers to any drug-containing formulation in which the manner and profile of drug release from the formulation are regulated. This refers to immediate as well as non-immediate release formulations, with non-immediate release formulations including, but not limited to, sustained release and delayed release formulations.

The term "cytokine," which refers to small soluble protein substances secreted by cells that have a variety of effects on other cells, is generically used to refer to many signaling molecules including, without limitation, lymphokines, interleukins, and chemokines. Cytokines mediate many important physiological functions including growth, development, wound healing, and the immune response. They act by binding to their cell-specific receptors located in the cell membrane that allows a distinct signal transduction cascade to start in the cell, which eventually will lead to biochemical and phenotypic changes in target cells. Generally, cytokines act locally, although some have been found to have systemic immunomodulatory effects, with pleiotropic autocrine, paracrine, and endocrine effects similar to hormones. They include type I cytokines, which encompass many of the interleukins, as well as several hematopoietic growth factors; type II cytokines, including the interferons and interleukin-10; tumor necrosis factor ("TNF")-related molecules, including TNF-α and lymphotoxin; immunoglobulin superfamily members, including interleukin 1 ("IL-1"); and the chemokines, a family of molecules that play a critical role in a wide variety of immune and inflammatory functions. The same cytokine can have different effects on a cell depending on the state of the cell. Cytokines often regulate the expression of, and trigger cascades of, other cytokines.

The term "delayed release" is used herein in its conventional sense to refer to a drug formulation in which there is a time delay between administration of the formulation and the release of the drug there from. "Delayed release" may or may not involve gradual release of drug over an extended period of time, and thus may or may not be "sustained release."

The term "derivative" as used herein means a compound that may be produced from another compound of similar structure in one or more steps. A "derivative" or "derivatives" of a peptide or a compound retains at least a degree of the desired function of the peptide or compound. Accordingly, an alternate term for "derivative" may be "functional derivative." Derivatives can include chemical modifications of the peptide, such as akylation, acylation, carbamylation, iodination or any modification that derivatizes the peptide. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formal groups. Free carboxyl groups can be derivatized to form salts, esters, amides, or hydrazides. Free hydroxyl groups can be derivatized to form O-acyl or O-alkyl derivatives. The imidazole nitrogen of histidine can be derivatized to form N-im-benzylhistidine. Also included as derivatives or analogues are those peptides that contain one or more naturally occurring amino acid derivative of the twenty standard amino acids, for example, 4-hydroxyproline, 5-hydroxylysine, 3-methylhistidine, homoserine, ornithine or carboxyglutamiate, and can include amino acids that are not linked by peptide bonds. Such peptide derivatives can be incorporated during synthesis of a peptide, or a peptide can be modified by well-known chemical modification methods (see, e.g., Glazer et al., Chemical Modification of Proteins, Selected Methods and Analytical Procedures, Elsevier Biomedical Press, New York (1975)).

The terms "disease" or "disorder" as used herein refer to an impairment of health or a condition of abnormal functioning, regardless of cause (whether heritable, environmental, dietary, infectious, due to trauma, or otherwise).

The term "domain" as used herein refers to a region of a protein with a characteristic tertiary structure and function and to any of the three-dimensional subunits of a protein that together makes up its tertiary structure formed by folding its linear peptide chain. The term "therapeutic domain" (also referred to as "TD") as used herein refers to a peptide, peptide segment or variant, or derivative thereof, with substantial identity to peptide KALARQLGVAA (SEQ ID NO: 2), or segment thereof. Therapeutic domains by themselves generally are not capable of penetrating the plasma membrane of mammalian cells. Once inside the cell, therapeutic domains can inhibit the kinase activity of a specific group of kinases.

The term "dry powder inhaler" or "DPI" as used herein refers to a device similar to a metered-dose inhaler, but where the drug is in powder form. The patient exhales out a full breath, places the lips around the mouthpiece, and then quickly breathes in the powder. Dry powder inhalers do not require the timing and coordination that are necessary with metered-dose inhalers.

The term "effective amount" as used herein refers to the amount necessary or sufficient to realize a desired biologic effect.

The term "endogenous" as used herein refers to growing or originating from within, or derived internally.

The term "endothelium" as used herein refers to a thin layer of cells that lines the interior surface of blood vessels, forming an interface between circulating blood in the lumen and the rest of the vessel wall. Endothelial cells will line the entire circulatory system, from the heart to the smallest capillary. These cells reduce turbulence of the flow of blood allowing the fluid to be pumped farther.

The term "eosinophils" or "eosinophil granulocytes" as used herein refers to white blood cells responsible for combating multicellular parasites and certain infections in vertebrates. They are granulocytes that develop during hematopoiesis in the bone marrow before migrating into blood. Along with mast cells, they also control mechanisms associated with allergy and asthma. Following activation, eosinophils exert diverse functions, including (1) production of cationic granule proteins and their release by degranulation, (2) production of reactive oxygen species, such as, superoxide, peroxide, and hypobromite (hypobromous acid, which is preferentially produced by eosinophil peroxidase), (3) production of lipid mediators, such as, eicosanoids from leukotriene and prostaglandin families, (4) production of growth factors, such as transforming growth factor (TGF-β), vascular endothelial growth factor (VEGF), and platelet-derived growth factor (PDGF), and (5) production of cytokines such as IL-1, IL-2, IL-4, IL-5, IL-6, IL-8, IL-13, and TNF-α.

The term "epithelium" as used herein refers to a tissue composed of cells that line the cavities and surfaces of structures throughout the body. The basal surface of the epithelium faces underlying connective tissue, and the two layers are separated by a basement membrane.

The term "extravasation" as used herein refers to the movement of blood cell components from the capillaries to the tissues surrounding them (diapedesis). In the case of malignant cancer metastasis, it refers to cancer cells exiting the capillaries and entering organs.

The term "exudation" as used herein refers to a process by which a fluid from the circulatory system passes through the walls of the blood vessels into lesions or areas of inflammation. Blood exudates contain some or all plasma proteins, white blood cells, platelets and red blood cells.

The terms "functional equivalent" or "functionally equivalent" are used interchangeably herein to refer to substances, molecules, polynucleotides, proteins, peptides, or polypeptides having similar or identical effects or use. A polypeptide functionally equivalent to polypeptide YARAAARQARAKALARQLGVAA (SEQ ID NO: 1), for example, may have a biologic activity, e.g., an inhibitory activity, kinetic parameters, salt inhibition, a cofactor-dependent activity, and/or a functional unit size that is substantially similar or identical to the expressed polypeptide of SEQ ID NO: 1.

Examples of polypeptides functionally equivalent to YARAAARQARAKALARQLGVAA (SEQ ID NO: 1) include, but are not limited to, a polypeptide of amino acid sequence FAKLAARLYRKALARQLGVAA (SEQ ID NO: 3), a polypeptide of amino acid sequence KAFAKLAARLYRKALARQLGVAA (SEQ ID NO: 4), a polypeptide of amino acid sequence YARAAARQARAKALARQLAVA (SEQ ID NO: 5), a polypeptide of amino acid sequence YARAAARQARAKALARQLGVA (SEQ ID NO: 6), and a polypeptide of amino acid sequence HRRIKAWLKKIKALARQLGVAA (SEQ ID NO: 7).

The MMI-0100 (YARAAARQARAKALARQLGVAA; SEQ ID NO: 1) peptide of amino acid sequence YARAAARQARAKALARQLGVAA (SEQ ID NO: 1) described in the present invention comprises a fusion protein in which a cell penetrating peptide (CPP; YARAAARQARA; SEQ ID NO: 11) is operatively linked to a therapeutic domain (KALARQLGVAA; SEQ ID NO: 2) in order to enhance therapeutic efficacy.

Examples of polypeptides functionally equivalent to therapeutic domain (TD; KALARQLGVAA; SEQ ID NO: 2) of the polypeptide YARAAARQARAKALARQLGVAA (SEQ ID NO: 1) include, but are not limited to, a polypeptide of amino acid sequence KALARQLAVA (SEQ ID NO: 8), a polypeptide of amino acid sequence KALARQLGVA (SEQ ID NO: 9), and a polypeptide of amino acid sequence KALARQLGVAA (SEQ ID NO: 10).

Examples of polypeptides functionally equivalent to the cell penetrating peptide (CPP; YARAAARQARA; SEQ ID NO: 11) of the polypeptide YARAAARQARAKALARQLGVAA (SEQ ID NO: 1) include, but are not limited to, a polypeptide of amino acid sequence WLRRIKAWLRRIKA (SEQ ID NO: 12), a polypeptide of amino acid sequence WLRRIKA (SEQ ID NO: 13), a polypeptide of amino acid sequence YGRKKRRQRRR (SEQ ID NO: 14), a polypeptide of amino acid sequence WLRRIKAWLRRI (SEQ ID NO: 15), a polypeptide of amino acid sequence FAKLAARLYR (SEQ ID NO: 16), a polypeptide of amino acid sequence KAFAKLAARLYR (SEQ ID NO: 17), and a polypeptide of amino acid sequence HRRIKAWLKKI (SEQ ID NO: 18).

The term "fusion protein" as used herein refers to a protein or polypeptide constructed by combining multiple protein domains or polypeptides for the purpose of creating a single polypeptide or protein with functional properties derived from each of the original proteins or polypeptides. Creation of a fusion protein may be accomplished by operatively ligating or linking two different nucleotides sequences that encode each protein domain or polypeptide via recombinant DNA technology, thereby creating a new polynucleotide sequences that codes for the desired fusion protein. Alternatively, a fusion protein maybe created by chemically joining the desired protein domains.

The term "growth" as used herein refers to a process of becoming larger, longer or more numerous, or an increase in size, number, or volume.

The term "inflammation" as used herein refers to the physiologic process by which vascularized tissues respond to injury. See, e.g., FUNDAMENTAL IMMUNOLOGY, 4th Ed., William E. Paul, ed. Lippincott-Raven Publishers, Philadelphia (1999) at 1051-1053, incorporated herein by reference. During the inflammatory process, cells involved in detoxification and repair are mobilized to the compromised site by inflammatory mediators. Inflammation is often characterized by a strong infiltration of leukocytes at the site of inflammation, particularly neutrophils (polymorphonuclear cells). These cells promote tissue damage by releasing toxic substances at the vascular wall or in uninjured tissue. Traditionally, inflammation has been divided into acute and chronic responses.

The term "acute inflammation" as used herein refers to the rapid, short-lived (minutes to days), relatively uniform response to acute injury characterized by accumulations of fluid, plasma proteins, and neutrophilic leukocytes. Examples of injurious agents that cause acute inflammation include, but are not limited to, pathogens (e.g., bacteria, viruses, parasites), foreign bodies from exogenous (e.g. asbestos) or endogenous (e.g., urate crystals, immune complexes), sources, and physical (e.g., burns) or chemical (e.g., caustics) agents.

The term "chronic inflammation" as used herein refers to inflammation that is of longer duration and which has a vague and indefinite termination. Chronic inflammation takes over when acute inflammation persists, either through incomplete clearance of the initial inflammatory agent (e.g., cigarette smoking) or as a result of multiple acute events occurring in the same location. Chronic inflammation, which includes the influx of lymphocytes and macrophages and fibroblast growth, may result in tissue scarring at sites of prolonged or repeated inflammatory activity.

The term "inflammatory mediators" as used herein refers to the molecular mediators of the inflammatory and immune processes. These soluble, diffusible molecules act both locally at the site of tissue damage and infection and at more distant sites. Some inflammatory mediators are activated by the inflammatory process, while others are synthesized and/or released from cellular sources in response to acute inflammation or by other soluble inflammatory mediators; still others exhibit anti-inflammatory properties. Examples of inflammatory mediators of the inflammatory response include, but are not limited to, plasma proteases, complement, kinins, clotting and fibrinolytic proteins, lipid mediators, prostaglandins, leukotrienes, platelet-activating factor (PAF), peptides, hormones (including steroid hormones such as glucocorticoids), and amines, including, but not limited to, histamine, serotonin, and neuropeptides, and proinflammatory cytokines, including, but not limited to, interleukin-1-beta (IL-1β), interleukin-4 (IL-4), interleukin-6 (IL-6), interleukin-8 (IL-8), tumor necrosis factor-alpha (TNF-α), interferon-gamma (IF-γ), interleukin-12 (IL-12), and interleukin-17 (IL-17).

Among the pro-inflammatory mediators, IL-1, IL-6, and TNF-α are known to activate hepatocytes in an acute phase response to synthesize acute-phase proteins that activate complement. Complement is a system of plasma proteins that interact with pathogens to mark them for destruction by phagocytes. Complement proteins can be activated directly by pathogens or indirectly by pathogen-bound antibody, leading to a cascade of reactions that occurs on the surface of pathogens and generates active components with various effector functions. IL-1, IL-6, and TNF-α also activate bone marrow endothelium to mobilize neutrophils, and function as endogenous pyrogens, raising body temperature, which helps eliminating infections from the body. A major effect of the cytokines is to act on the hypothalamus, altering the body's temperature regulation, and on muscle and fat cells, stimulating the catabolism of the muscle and fat cells to elevate body temperature. At elevated temperatures, bacterial and viral replications are decreased, while the adaptive immune system operates more efficiently.

The term "inhalation" as used herein refers to the act of drawing in a medicated vapor with the breath.

The term "inhalation delivery device" as used herein refers to a machine/apparatus or component that produces small droplets or an aerosol from a liquid or dry powder aerosol formulation and is used for administration through the mouth in order to achieve pulmonary administration of a drug, e.g., in solution, powder, and the like. Examples of inhalation delivery device include, but are not limited to, a nebulizer, a metered-dose inhaler, and a dry powder inhaler (DPI).

The terms "inhibiting", "inhibit" or "inhibition" are used herein to refer to reducing the amount or rate of a process, to stopping the process entirely, or to decreasing, limiting, or blocking the action or function thereof. Inhibition may include a reduction or decrease of the amount, rate, action function, or process of a substance by at least 5%, at least 10%, at least 15%, at least 20%, at least 25%, at least 30%, at least 40%, at least 45%, at least 50%, at least 55%, at least 60%, at least 65%, at least 70%, at least 75%, at least 80%, at least 85%, at least 90%, at least 95%, at least 98%, or at least 99%.

The term "inhibitor" as used herein refers to a second molecule that binds to a first molecule thereby decreasing the first molecule's activity. Enzyme inhibitors are molecules that bind to enzymes thereby decreasing enzyme activity. The binding of an inhibitor may stop a substrate from entering the active site of the enzyme and/or hinder the enzyme from catalyzing its reaction. Inhibitor binding is either reversible or irreversible. Irreversible inhibitors usually react with the enzyme and change it chemically, for example, by modifying key amino acid residues needed for enzymatic activity. In contrast, reversible inhibitors bind non-covalently and produce different types of inhibition depending on whether these inhibitors bind the enzyme, the enzyme-substrate complex, or both. Enzyme inhibitors often are evaluated by their specificity and potency.

The term "injury" as used herein refers to damage or harm to a structure or function of the body caused by an outside agent or force, which may be physical or chemical.

The term "insufflation" as used herein refers to the act of delivering air, a gas, or a powder under pressure to a cavity or chamber of the body. For example, nasal insufflation relates to the act of delivering air, a gas, or a powder under pressure through the nose.

The term "interleukin (IL)" as used herein refers to a cytokine from a class of homologously related proteins that were first observed to be secreted by, and acting on, leukocytes. It has since been found that interleukins are produced by a wide variety of body cells. Interleukins regulate cell growth, differentiation, and motility, and stimulates immune responses, such as inflammation. Examples of interleukins include, interleukin-1 (IL-1), interleukin-1β (IL-1β), interleukin-6 (IL-6), interleukin-8 (IL-8), interleukin-12 (IL-12), and interleukin-17 (IL-17).

The term "invasion" or "invasiveness" as used herein refers to a process in malignant cells that includes penetration of and movement through surrounding tissues.

The term "isolated" is used herein to refer to material, such as, but not limited to, a nucleic acid, peptide, polypeptide, or protein, which is: (1) substantially or essentially free from components that normally accompany or interact with it as found in its naturally occurring environment. The terms "substantially free" or "essentially free" are used herein to refer to considerably or significantly free of, or more than about 95% free of, or more than about 99% free of such components. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material may be performed on the material within, or removed, from its natural state. For example, a naturally occurring nucleic acid becomes an isolated nucleic acid if it is altered, or if it is transcribed from DNA that has been altered, by means of human intervention performed within the cell from which it originates. See, for example, Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868, each incorporated herein by reference in its entirety. Likewise, a naturally occurring nucleic acid (for example, a promoter) becomes isolated if it is introduced by non-naturally occurring means to a locus of the genome not native to that nucleic acid. Nucleic acids that are "isolated" as defined herein also are referred to as "heterologous" nucleic acids.

The term "Kaplan Meier plot" or "Kaplan Meier survival curve" as used herein refers to the plot of probability of clinical study subjects surviving in a given length of time while considering time in many small intervals. The Kaplan Meier plot assumes that: (i) at any time subjects who are censored (i.e., lost) have the same survival prospects as subjects who continue to be followed; (ii) the survival probabilities are the same for subjects recruited early and late in the study; and (iii) the event (e.g., death) happens at the time specified. Probabilities of occurrence of event are computed at a certain point of time with successive probabilities multiplied by any earlier computed probabilities to get a final estimate. The survival probability at any particular time is calculated as the number of subjects surviving divided by the number of subjects at risk. Subjects who have died, dropped out, or have been censored from the study are not counted as at risk.

The term "kinase" as used herein refers to a type of enzyme that transfers phosphate groups from high-energy donor molecules to specific target molecules or substrates. High-energy donor groups may include, but are not limited, to ATP.

The term "leukocyte" or "white blood cell (WBC)" as used herein refers to a type of immune cell. Most leukocytes are made in the bone marrow and are found in the blood and lymph tissue. Leukocytes help the body fight infections and other diseases. Granulocytes, monocytes, and lymphocytes are leukocytes.

The term "long-term" release, as used herein, refers to delivery of therapeutic levels of the active ingredient for at least 7 days, and potentially up to about 30 to about 60 days. Terms such as "long-acting", "sustained-release" or "controlled release" are used generally to describe a formulation, dosage form, device or other type of technologies used, such as, for example, in the art to achieve the prolonged or extended release or bioavailability of a bioactive agent to a subject; it may refer to technologies that provide prolonged or extended release or bioavailability of a bioactive agent to the general systemic circulation or a subject or to local sites of action in a subject including (but not limited to) cells, tissues, organs, joints, regions, and the like. Furthermore, these terms may refer to a technology that is used to prolong or extend the release of a bioactive agent from a formulation or dosage form or they may refer to a technology used to extend or prolong the bioavailability or the pharmacokinetics or the duration of action of a bioactive agent to a subject or they may refer to a technology that is used to extend or prolong the pharmacodynamic effect elicited by a formulation. A "long-acting formulation," a "sustained release formulation," or a "controlled release formulation" (and the like) is a pharmaceutical formulation, dosage form, or other technology that is used to provide long-acting release of a bioactive agent to a subject.

The terms "lung interstitium" or "pulmonary interstitium" are used interchangeably herein to refer to an area located between the airspace epithelium and pleural mesothelium in the lung. Fibers of the matrix proteins, collagen and elastin, are the major components of the pulmonary interstitium. The primary function of these fibers is to form a mechanical scaffold that maintains structural integrity during ventilation.

The term "lymphocytes" as used herein refers to a small white blood cell (leukocyte) that plays a large role in defending the body against disease. There are two main types of lymphocytes: B cells and T cells. The B cells make antibodies that attack bacteria and toxins while the T cells themselves attack body cells when they have been taken over by viruses or have become cancerous. Lymphocytes secrete products (lymphokines) that modulate the functional activities of many other types of cells and are often present at sites of chronic inflammation.

The term "macrophage" as used herein refers to a type of white blood cell that surrounds and kills microorganisms, removes dead cells, and stimulates the action of other immune system cells. After digesting a pathogen, a macrophage presents an antigen (a molecule, most often a protein found on the surface of the pathogen, used by the immune system for identification) of the pathogen to the corresponding helper T cell. The presentation is done by integrating it into the cell membrane and displaying it attached to an MHC class II molecule, indicating to other white blood cells that the macrophage is not a pathogen, despite having antigens on its surface. Eventually, the antigen presentation results in the production of antibodies that attach to the antigens of pathogens, making them easier for macrophages to adhere to with their cell membrane and phagocytose.

The terms "marker" and "cell surface marker" are used interchangeably herein to refer to a receptor, a combination of receptors, or an antigenic determinant or epitope found on the surface of a cell that allows a cell type to be distinguishable from other kinds of cells. Specialized protein receptors (markers) that have the capability of selectively binding or adhering to other signaling molecules coat the surface of every cell in the body. Cells use these receptors and the molecules that bind to them as a way of communicating with other cells and to carry out their proper function in the body. Cell sorting techniques are based on cellular biomarkers where a cell surface marker(s) may be used for either positive selection or negative selection, i.e., for inclusion or exclusion, from a cell population.

The term "maximum tolerated dose" as used herein refers to the highest dose of a drug that does not produce unacceptable toxicity.

The term "median survival" as used herein refers to the time after which 50% of individuals with a particular condition are still living and 50% have died. For example, a median survival of 6 months indicates that after 6 months, 50% of individuals with non-small cell lung cancer would be alive, and 50% would have passed away. Median survival is often used to described the prognosis (i.e., chance of survival) of a condition when the average survival rate is relatively short, such as for lung cancer. Median survival is also used in clinical studies when a drug or treatment is being evaluated to determine whether or not the drug or treatment will extend life.

The term "mesenchymal cell" or "mesenchyme" as used herein refers to a cell derived from all three germ layers, which can develop into connective tissue, bone, cartilage, the lymphatic system, and the circulatory system.

The term "metered-dose inhaler", "MDI", or "puffer" as used herein refers to a pressurized, hand-held device that uses propellants to deliver a specific amount of medicine ("metered dose") to the lungs of a patient. The term "propellant" as used herein refers to a material that is used to expel a substance usually by gas pressure through a convergent, divergent nozzle. The pressure may be from a compressed gas, or a gas produced by a chemical reaction. The exhaust material may be a gas, liquid, plasma, or, before the chemical reaction, a solid, liquid or gel. Propellants used in pressurized metered dose inhalers are liquefied gases, traditionally chlorofluorocarbons (CFCs) and increasingly hydrofluoroalkanes (HFAs). Suitable propellants include, for example, a chlorofluorocarbon (CFC), such as trichlorofluoromethane (also referred to as propellant 11), dichlorodifluoromethane (also referred to as propellant 12), and 1,2-dichloro-1,1,2,2-tetrafluoroethane (also referred to as propellant 114), a hydrochlorofluorocarbon, a hydrofluorocarbon (HFC), such as 1,1,1,2-tetrafluoroethane (also referred to as propellant 134a, HFC-134a, or HFA-134a) and 1,1,1,2,3,3,3-heptafluoropropane (also referred to as propellant 227, HFC-227, or HFA-227), carbon dioxide, dimethyl ether, butane, propane, or mixtures thereof. In other embodiments, the propellant includes a chlorofluorocarbon, a hydrochlorofluorocarbon, a hydrofluorocarbon, or mixtures thereof. In other embodiments, a hydrofluorocarbon is used as the propellant. In other embodiments, HFC-227 and/or HFC-134a are used as the propellant.

The term "migration" as used herein refers to a movement of a population of cells from one place to another.

The term "MK2 kinase" or "MK2" as used herein refers to mitogen-activated protein kinase-activated protein kinase 2 (also referred to as "MAPKAPK2", "MAPKAP-K2", "MK2"), which is a member of the serine/threonine (Ser/Thr) protein kinase family.

The term "modulate" as used herein means to regulate, alter, adapt, or adjust to a certain measure or proportion.

The term "monocyte" as used herein refers to a type of immune cell that is made in the bone marrow and travels through the blood to tissues in the body where it becomes a macrophage. A monocyte is a type of white blood cell and a type of phagocyte.

The term "nebulizer" as used herein refers to a device used to administer liquid medication in the form of a mist inhaled into the lungs.

The term "neutrophils" or "polymorphonuclear neutrophils (PMNs)" as used herein refers to the most abundant type of white blood cells in mammals, which form an essential part of the innate immune system. They form part of the polymorphonuclear cell family (PMNs) together with basophils and eosinophils. Neutrophils are normally found in the blood stream. During the beginning (acute) phase of inflammation, particularly as a result of bacterial infection and some cancers, neutrophils are one of the first-responders of inflammatory cells to migrate toward the site of inflammation. They migrate through the blood vessels, then through interstitial tissue, following chemical signals such as interleukin-8 (IL-8) and C5a in a process called chemotaxis, the directed motion of a motile cell or part along a chemical concentration gradient toward environmental conditions it deems attractive and/or away from surroundings it finds repellent.

The term "non-small cell lung cancer" as used herein refers to a group of lung cancers named for the kinds of cells found in the cancer and how the cells look microscopically. It is the most common type of lung cancer. The three main types of non-small cell lung cancer are squamous cell carcinoma, large cell carcinoma, and adenocarcinoma. The term "squamous cell carcinoma" as used herein refers to a non-small cell lung cancer that begins in squamous cells, which are thin, flat cells found in the tissue that forms the lining of the respiratory tract. Squamous cell carcinomas are found in the center of the lung next to a bronchus. The term "large cell carcinoma" refers to a lung cancer in which the cells are large and look abnormal when viewed microscopically. Large cell carcinomas can occur in any part of the lung, and tend to grow and spread faster than the other two types. The term "adenocarcinoma" as used herein refers to a cancer that begins in glandular (secretory) cells; adenocarcinomas are found in an outer area of the lung. The term "adenocarcinoma in situ" as used herein refers to a condition in which abnormal cells are found in the glandular tissue, which may become cancer and spread to nearby normal tissue.

The term "normal healthy control subject" as used herein refers to a subject having no symptoms or other clinical evidence of airway or lung tissue disease.

The term "nucleic acid" is used herein to refer to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

The term "nucleotide" is used herein to refer to a chemical compound that consists of a heterocyclic base, a sugar, and one or more phosphate groups. In the most common nucleotides, the base is a derivative of purine or pyrimidine, and the sugar is the pentose deoxyribose or ribose. Nucleotides are the monomers of nucleic acids, with three or more bonding together in order to form a nucleic acid. Nucleotides are the structural units of RNA, DNA, and several cofactors, including, but not limited to, CoA, FAD, DMN, NAD, and NADP. Purines include adenine (A), and guanine (G); pyrimidines include cytosine (C), thymine (T), and uracil (U).

The following terms are used herein to describe the sequence relationships between two or more nucleic acids or polynucleotides: (a) "reference sequence", (b) "comparison window", (c) "sequence identity", (d) "percentage of sequence identity", and (e) "substantial identity."

(a) The term "reference sequence" refers to a sequence used as a basis for sequence comparison. A reference sequence may be a subset or the entirety of a specified sequence; for example, as a segment of a full-length cDNA or gene sequence, or the complete cDNA or gene sequence.

(b) The term "comparison window" refers to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be at least 30 contiguous nucleotides in length, at least 40 contiguous nucleotides in length, at least 50 contiguous nucleotides in length, at least 100 contiguous nucleotides in length, or longer. Those of skill in the art understand that to avoid a high similarity to a reference sequence due to inclusion of gaps in the polynucleotide sequence, a gap penalty typically is introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73:237-244 (1988); Higgins and Sharp, *CABIOS* 5:151-153 (1989); Corpet, et al., Nucleic Acids Research 16:10881-90 (1988); Huang, et al., Computer Applications in the *Biosciences,* 8:155-65 (1992), and Pearson, et al., *Methods in Molecular Biology,* 24:307-331 (1994). The BLAST family of programs, which can be used for database similarity searches, includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et al., *Nucleic Acids Res.* 25:3389-3402 (1997). Software for performing BLAST analyses is publicly available, e.g., through the National Center for Biotechnology-Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits then are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Natl. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. BLAST searches assume that proteins may be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs may be employed to reduce such low-complexity alignments. For example, the SEG (Wooten and Federhen, *Comput. Chem.*, 17:149-163 (1993)) and XNU (Claverie and States, *Comput. Chem.*, 17:191-201 (1993)) low-complexity filters may be employed alone or in combination.

(c) The term "sequence identity" or "identity" in the context of two nucleic acid or polypeptide sequences is used herein to refer to the residues in the two sequences that are the same when aligned for maximum correspondence over a specified comparison window. When percentage of sequence identity is used in reference to proteins it is recognized that residue positions that are not identical often differ by conservative amino acid substitutions, i.e., where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.*, 4:11-17 (1988) e.g., as implemented in the program PC/GENE (Intelligenetics, Mountain View, Calif., USA).

(d) The term "percentage of sequence identity" is used herein mean the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) The term "substantial identity" of polynucleotide sequences means that a polynucleotide comprises a sequence that has at least 70% sequence identity, at least 80% sequence identity, at least 90% sequence identity and at least 95% sequence identity, compared to a reference sequence using one of the alignment programs described using standard parameters. One of skill will recognize that these values may be adjusted appropriately to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or at least 70%, at least 80%, at least 90%, or at least 95%. Another indication that nucleotide sequences are substantially identical is if two molecules hybridize to each other under stringent conditions. However, nucleic acids that do not hybridize to each other under stringent conditions are still substantially identical if the polypeptides that they encode are substantially identical. This may occur, e.g., when a copy of a nucleic acid is created using the maximum codon degeneracy permitted by the genetic code. One indication that two nucleic acid sequences are substantially identical is that the polypeptide that the first nucleic acid encodes is immunologically cross reactive with the polypeptide encoded by the second nucleic acid.

The phrase "operatively linked" as used herein refers to a linkage in which two or more protein domains or polypeptides are ligated or combined via recombinant DNA technology or chemical reaction such that each protein domain or polypeptide of the resulting fusion protein retains its original function. For example, SEQ ID NO: 1 is constructed by operatively linking a cell penetrating peptide (SEQ ID NO: 11) with a therapeutic domain (SEQ ID NO: 2), thereby creating a fusion peptide that possesses both the cell penetrating function of SEQ ID NO: 11 and the kinase inhibitor function of SEQ ID NO: 2.

The term "outcome" as used herein refers to a specific result or effect that can be measured. Nonlimiting examples of outcomes include decreased pain, reduced tumor size, and improvement of disease.

The term "overall survival" or "OS" as used herein refers to the length of time from either the date of diagnosis or the start of treatment for a disease, such as cancer, that patients diagnosed with the disease are still alive.

The term "parenchyma" as used herein refers to an animal tissue that constitutes the essential part of an organ as contrasted with connective tissue or blood vessels. The term "parenchymal" means pertaining to the parenchyma of an organ.

The term "parenteral" as used herein refers to introduction into the body by way of an injection (i.e., administration by injection), including, for example, subcutaneously (i.e., an injection beneath the skin), intramuscularly (i.e., an injection into a muscle), intravenously (i.e., an injection into a vein), intrathecally (i.e., an injection into the space around the spinal cord or under the arachnoid membrane of the brain), intrasternal injection or infusion techniques, and including intraperitoneal injection or infusion into the body cavity (e.g. peritoneum). A parenterally administered composition is delivered using a needle, e.g., a surgical needle, or other corporal access device. The term "surgical needle" as used herein, refers to any access device adapted for delivery of fluid (i.e., capable of flow) compositions into a selected anatomical structure. Injectable preparations, such as sterile injectable aqueous or oleaginous suspensions, may be formulated according to the known art using suitable dispersing or wetting agents and suspending agents.

The term "particulate" as used herein refers to fine particles of solid or liquid matter suspended in a gas or liquid.

The term "particle" as used herein refers to an extremely small constituent (e.g., femoparticles ($10^{-15}$ m), picoparticles ($10^{-12}$), nanoparticles ($10^{-9}$ m), microparticles ($10^{-6}$ m), milliparticles ($10^{-3}$ m)) in or on which is contained the composition as described herein. The particles may be of any order release kinetics, including zero order release, first order release, second order release, delayed release, sustained release, immediate release, etc., and any combination thereof. The particle may include, in addition to a therapeutic agent(s), any of those materials routinely used in the art of pharmacy and medicine, including, but not limited to, erodible, nonerodible, biodegradable, or nonbiodegradable material or combinations thereof.

As used herein the term "pharmaceutically acceptable carrier" refers to any substantially non-toxic carrier conventionally useable for administration of pharmaceuticals in which the isolated polypeptide of the present invention will remain stable and bioavailable. The pharmaceutically acceptable carrier must be of sufficiently high purity and of sufficiently low toxicity to render it suitable for administration to the mammal being treated. It further should maintain the stability and bioavailability of an active agent. The pharmaceutically acceptable carrier can be liquid or solid and is selected, with the planned manner of administration in mind, to provide for the desired bulk, consistency, etc., when combined with an active agent and other components of a given composition.

The term "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, the protein is specifically reactive to antibodies elicited to the same protein but consisting entirely of naturally occurring amino acids.

The terms "polypeptide" and "protein" also are used herein in their broadest sense to refer to a sequence of subunit amino acids, amino acid analogs, or peptidomimetics. The subunits are linked by peptide bonds, except where noted. The polypeptides described herein may be chemically synthesized or recombinantly expressed. Polypeptides of the described invention also can be synthesized chemically. Synthetic polypeptides, prepared using the well known techniques of solid phase, liquid phase, or peptide condensation techniques, or any combination thereof, can include natural and unnatural amino acids. Amino acids used for peptide synthesis may be standard Boc (N-α-amino protected N-α-t-butyloxycarbonyl) amino acid resin with the standard deprotecting, neutralization, coupling and wash protocols of the original solid phase procedure of Merrifield (1963, *J. Am. Chem. Soc.* 85:2149-2154), or the base-labile N-α-amino protected 9-fluorenylmethoxycarbonyl (Fmoc) amino acids first described by Carpino and Han (1972, *J. Org. Chem.* 37:3403-3409). Both Fmoc and Boc N-α-amino protected amino acids can be obtained from Sigma, Cambridge Research Biochemical, or other chemical companies familiar to those skilled in the art. In addition, the polypeptides can be synthesized with other N-α-protecting groups that are familiar to those skilled in this art. Solid phase peptide synthesis may be accomplished by techniques familiar to those in the art and provided, for example, in Stewart and Young, 1984, *Solid Phase Synthesis*, Second Edition, Pierce Chemical Co., Rockford, Ill.; Fields and Noble, 1990, *Int. J. Pept. Protein Res.* 35:161-214, or using automated synthesizers. The polypeptides of the invention may comprise D-amino acids (which are resistant to L-amino acid-specific proteases in vivo), a combination of D- and L-amino acids, and various "designer" amino acids (e.g., β-methyl amino acids, C-α-methyl amino acids, and N-α-methyl amino acids, etc.) to convey special properties. Synthetic amino acids include ornithine for lysine, and norleucine for leucine or isoleucine. In addition, the polypeptides can have peptidomimetic bonds, such as ester bonds, to prepare peptides with novel properties. For example, a peptide may be generated that incorporates a reduced peptide bond, i.e., R1-$CH_2$—NH—R2, where R1 and R2 are amino acid residues or sequences. A reduced peptide bond may be introduced as a dipeptide subunit. Such a polypeptide would be resistant to protease activity, and would possess an extended half-live in vivo. Accordingly, these terms also apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, the protein is specifically reactive to antibodies elicited to the same protein but consisting entirely of naturally occurring amino acids.

The terms "polypeptide", "peptide" and "protein" also are inclusive of modifications including, but not limited to, glycosylation, lipid attachment, sulfation, gamma-carboxylation of glutamic acid residues, hydroxylation, and ADP-ribosylation. It will be appreciated, as is well known and as noted above, that polypeptides may not be entirely linear. For instance, polypeptides may be branched as a result of ubiquitination, and they may be circular, with or without branching, generally as a result of posttranslational events, including natural processing event and events brought about by human manipulation which do not occur naturally. Circular, branched and branched circular polypeptides may be synthesized by non-translation natural process and by entirely synthetic methods, as well. In some embodiments, the peptide is of any length or size.

The terms "primary tumor" or "primary cancer" are used interchangeably to refer to the original, or first, tumor in the body. Cancer cells from a primary cancer may spread to other parts of the body and form new, or secondary tumors. This is called metastasis. The secondary tumors are the same type of cancer as the primary cancer.

The term "proenzyme" or "zymogen" as used herein refers to an inactive enzyme precursor. A zymogen requires a biochemical change (such as a hydrolysis reaction revealing the active site, or changing the configuration to reveal the active site) for it to become an active enzyme. The biochemical change usually occurs in a lysosome where a specific part of the precursor enzyme is cleaved in order to activate it. The amino acid chain that is released upon activation is called the activation peptide.

The term "progression" as used herein, refers to the course of a disease, such as cancer, as it becomes worse or spreads in the body.

The term "progression-free survival" or PFS, as used herein, refers to the length of time during and after the treatment of a disease, such as cancer, that a patient lives with the disease but it does not get worse.

The term "proliferation" as used herein refers to expansion of a population of cells by the continuous division of single cells into identical daughter cells.

The term "pulmonary interstitium" as used herein refers to the tissue and space around the air sacs of the lungs.

The term "pulmonary alveolus" as used herein refers to an anatomical structure that has the form of a hollow cavity. The alveoli are located in the respiratory zone of the lungs, at the distal termination of the alveolar ducts and atria, forming the termination point of the respiratory tract. The pulmonary alveoli are spherical outcroppings of the respiratory sites of gas exchange with the blood and only found in the mammalian lungs. The alveolar membrane is the gas-exchange surface. The blood brings carbon dioxide from the rest of the body for release into the alveoli, and the oxygen in the alveoli is taken up by the blood in the alveolar blood vessels, to be transported to all the cells in the body. The alveoli contain some collagen and elastic fibers. The elastic fibers allow the alveoli to stretch as they fill with air when breathing in. They then spring back during breathing out in order to expel the carbon dioxide-rich air. There are three major alveolar cell types in the alveolar wall, (1) sequamous alveolar cells that form the structure of an alveolar wall, (2) great alveolar cells that secrete pulmonary surfactant to lower the surface tension of water and allows the membrane to separate, thereby increasing the capability to exchange gasses, (3) macrophages that destroy foreign pathogens, such as bacteria.

The term "recurrent cancer" or "recurrence" as used herein that has recurred (come back), usually after a period of time during which the cancer could not be detected. The cancer may come back to the same place as the original (primary) tumor or to another place in the body.

The term "reduce" or "reducing" as used herein refers to a diminution, a decrease, an attenuation, limitation or abatement of the degree, intensity, extent, size, amount, density, number or occurrence of disorder in individuals at risk of developing the disorder.

The term "refractory" as used herein refers to a cancer that does not respond to treatment.

The term "remission" as used herein refers to a decrease in or disappearance of signs and symptoms of cancer. In partial remission, some, but not all signs and symptoms of cancer have disappeared. In complete remission, all signs and symptoms of cancer have disappeared, although cancer may still be in the body.

The term Response Evaluation Criteria in Solid Tumors (or "RECIST") as used herein refers to a standard way to measure how well a cancer patient responds to treatment. It is based on whether tumors shrink, stay the same, or get bigger. To use RECIST, there must be at least one tumor that can be measured on x-rays, CT scans, or MRI scans. The types of response a patient can have are a complete response (CR), a partial response (PR), progressive disease (PD), and stable disease (SD).

The term "sign" as used herein refers to something found during a physical exam or from a laboratory test that shows that a person may have a condition or disease.

The term "similar" is used interchangeably with the terms analogous, comparable, or resembling, meaning having traits or characteristics in common.

The term "solution" as used herein refers to a homogeneous mixture of two or more substances. It is frequently, though not necessarily, a liquid. In a solution, the molecules of the solute (or dissolved substance) are uniformly distributed among those of the solvent.

The terms "soluble" and "solubility" refer to the property of being susceptible to being dissolved in a specified fluid (solvent). The term "insoluble" refers to the property of a material that has minimal or limited solubility in a specified solvent. In a solution, the molecules of the solute (or dissolved substance) are uniformly distributed among those of the solvent.

The term "stress fiber" as used herein refers to high order structures in cells consisting of actin filaments, crosslinking proteins (proteins that bind two or more filaments together), and myosin II motors. Actin is a globular protein (~43 kDa), which polymerizes and forms into an ordered filament structure which has two protofilaments wrapping around each other, to form a single "actin filament" also known as a "microfilament." The myosin motors in the stress fibers move, sliding actin filaments past one another, so the fiber can contract. In order for contraction to generate forces, the fibers must be anchored to something. Stress fibers can anchor to the cell membrane, and frequently the sites where this anchoring occurs are also connected to structures outside the cell (the matrix or some other substrate). These connection sites are called focal adhesions. Many proteins are required for proper focal adhesion production and maintenance. Contraction against these fixed external substrates is what allows the force generated by myosin motors and filament growth and rearrangement to move and reshape the cell.

The terms "subject" or "individual" or "patient" are used interchangeably to refer to a member of an animal species of mammalian origin, including but not limited to, a mouse, a rat, a cat, a goat, sheep, horse, hamster, ferret, platypus, pig, a dog, a guinea pig, a rabbit and a primate, such as, for example, a monkey, ape, or human.

The phrase "subject in need of such treatment" as used herein refers to a patient who suffers from a disease, disorder, condition, or pathological process. In some embodiments, the term "subject in need of such treatment" also is used to refer to a patient who (i) will be administered at least one polypeptide of the invention; (ii) is receiving at least one polypeptide of the invention; or (iii) has received at least one polypeptide of the invention, unless the context and usage of the phrase indicates otherwise.

The terms "substantial inhibition", "substantially inhibited" and the like as used herein refer to inhibition of at least 50%, inhibition of at least 55%, inhibition of at least 60%, inhibition of at least 65%, inhibition of at least 70%, inhibition of at least 75%, inhibition of at least 80%, inhibition of at least 85%, inhibition of at least 90%, inhibition of at least 95%, or inhibition of at least 99%.

The term "substitution" is used herein to refer to a situation in which a base or bases are exchanged for another base or bases in a DNA sequence. Substitutions may be synonymous substitutions or nonsynonymous substitutions. As used herein, "synonymous substitutions" refer to substitutions of one base for another in an exon of a gene coding for a protein, such that the amino acid sequence produced is not modified. The term "nonsynonymous substitutions" as used herein refer to substitutions of one base for another in an exon of a gene coding for a protein, such that the amino acid sequence produced is modified.

The term "survival rate" as used herein refers to the percent of individuals who survive a disease (e.g., cancer) for a specified amount of time. For example, if the 5-year survival rate for a particular cancer is 34%, this means that 34 out of 100 individuals initially diagnosed with that cancer would be alive after 5 years.

The term "suspension" as used herein refers to a dispersion (mixture) in which a finely-divided species is combined with another species, with the former being so finely divided and mixed that it doesn't rapidly settle out. In everyday life, the most common suspensions are those of solids in liquid.

The term "sustained release" (also referred to as "extended release") is used herein in its conventional sense to refer to a drug formulation that provides for gradual release of a drug over an extended period of time, and that may results in substantially constant levels of the drug over an extended time period.

The term "symptom" as used herein refers to a sign or a disease or condition. The terms "symptom management", "palliative care," and "supportive care" are used interchangeably herein to refer to care given to improve the quality of life (QOL) of patients who have a serious or life-threatening disease.

The terms "therapeutic amount," an "amount effective," or "pharmaceutically effective amount" of an active agent are used interchangeably to refer to an amount that is sufficient to provide the intended benefit of treatment. For example, the "therapeutic amount" of a kinase inhibiting composition of the described invention includes, but is not limited to, an amount sufficient to reduce cancer cell proliferation, to reduce tumor size, to reduce tumor burden, to induce cancer cell death, to overcome tumor chemoresistance, to enhance tumor chemosensitivity, or a combination thereof. The term also encompasses an amount sufficient to suppress or alleviate at least one symptom of a non-small cell lung cancer patient, wherein the symptom includes, but is not limited to, chest pain, cough, coughing up blood, fatigue, loss of appetite, losing weight without trying, shortness of breadth, wheezing, recurring infections such as bronchitis and pneumonia, bone pain (e.g., in the back or hips), nervous system changes (e.g., headache, weakness or numbness of an arm or leg, dizziness, balance problems, seizures), yellowing of the skin and eyes (i.e, jaundice), lumps near the surface of the body, drooping or weakness of one eyelid with a smaller pupil in the same eye and reduced or absent sweating on the same side of the face (Horner syndrome), swelling in the face, neck, arms and upper chest often accompanied by a bluish-red skin color (superior vena cava syndrome), retention of water by kidneys resulting in fatigue, loss of appetite, muscle weakness, cramps, nausea, vomiting, restlessness, and confusion (syndrome of inappropriate anti-diuretic hormone), secretion of cortisol by the adrenal glands resulting in weight gain, easy bruising weakness, drowsiness, and fluid retention (cushing syndrome), weakness in the muscles around the hips (Lanbert-Eaton syndrome), loss of balance and usteadiness in arm and leg movements (paraneoplastic cerebellar degeneration), high blood calcium levels (hypercalcemia), excess growth of certain bones (e.g., bones of the fingertips), blood clots, and excess breast growth in men (gynecomastia).

An effective amount of an active agent that can be employed according to the described invention generally ranges from generally about 0.001 mg/kg body weight to about 10 g/kg body weight. However, dosage levels are based on a variety of factors, including the type of injury, the age, weight, sex, medical condition of the patient, the severity of the condition, the route and frequency of administration, and the particular active agent employed. Thus the dosage regimen may vary widely, but can be determined routinely by a physician using standard methods.

The term "treat" or "treating" includes abrogating, substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder (s) in patients that have previously had the disorder(s); and (e) limiting recurrence of symptoms in patients that were previously asymptomatic for the disorder(s).

The term "tumor" as used herein refers to a disease involving abnormal cell growth in numbers (proliferation) or in size with the potential to invade or spread to other parts of the body (metastasis).

The term "tumor burden" or "tumor load" are used interchangeably herein fers to the number of cancer cells, the size of a tumor, or the amount of cancer in the body.

The term "tumor necrosis factor" as used herein refers to a cytokine made by white blood cells in response to an antigen or infection, which induce necrosis (death) of tumor cells and possesses a wide range of pro-inflammatory actions. Tumor necrosis factor also is a multifunctional cytokine with effects on lipid metabolism, coagulation, insulin resistance, and the function of endothelial cells lining blood vessels.

The terms "variants", "mutants", and "derivatives" are used herein to refer to nucleotide or polypeptide sequences with substantial identity to a reference nucleotide or polypeptide sequence. The differences in the sequences may be the result of changes, either naturally or by design, in sequence or structure. Natural changes may arise during the course of normal replication or duplication in nature of the particular nucleic acid sequence. Designed changes may be specifically designed and introduced into the sequence for specific purposes. Such specific changes may be made in vitro using a variety of mutagenesis techniques. Such sequence variants generated specifically may be referred to as "mutants" or "derivatives" of the original sequence.

A skilled artisan likewise can produce polypeptide variants of polypeptide YARAAARQARAKALARQLGVAA (SEQ ID NO: 1) having single or multiple amino acid substitutions, deletions, additions or replacements, but functionally equivalent to SEQ ID NO: 1. These variants may include inter alia: (a) variants in which one or more amino acid residues are substituted with conservative or non-conservative amino acids; (b) variants in which one or more amino acids are added; (c) variants in which at least one amino acid includes a substituent group; (d) variants in which amino acid residues from one species are substituted for the corresponding residue in another species, either at conserved or non-conserved positions; and (d) variants in which a target protein is fused with another peptide or polypeptide such as a fusion partner, a protein tag or other chemical moiety, that may confer useful properties to the target protein, for example, an epitope for an antibody. The techniques for obtaining such variants, including, but not limited to, genetic (suppressions, deletions, mutations, etc.), chemical, and enzymatic techniques, are known to the skilled artisan. As used herein, the term "mutation" refers to a change of the DNA sequence within a gene or chromosome of an organism resulting in the creation of a new character or trait not found in the parental type, or the process by which such a change occurs in a chromosome, either through an alteration in the nucleotide sequence of the DNA coding for a gene or through a change in the physical arrangement of a chromosome. Three mechanisms of mutation include substitution (exchange of one base pair for another), addition (the insertion of one or more bases into a sequence), and deletion (loss of one or more base pairs).

The term "vehicle" as used herein refers to a substance that facilitates the use of a drug or other material that is mixed with it.

I. Compositions: Therapeutic Peptides for Treating Signs or Symptoms of Non-Small Cell Lung Cancer (NSCLC)

According to one aspect, the described invention provides a pharmaceutical composition for use in the treatment of a non-small cell lung cancer (NSCLC) solid tumor comprising a population of tumor cells, wherein the pharmaceutical composition comprises a therapeutic amount of a polypeptide of the amino acid sequence YARAAARQARAKALARQLGVAA (SEQ ID NO: 1) or a functional equivalent thereof, and a pharmaceutically acceptable carrier thereof, and wherein the therapeutic amount may be effective to inhibit a kinase activity of a kinase selected from the group listed in Table 1 in the population of tumor cells and to reduce cancer cell proliferation, to reduce tumor size, to reduce tumor burden, to induce tumor cell death, to overcome tumor chemoresistance, to enhance tumor chemosensitivity, or a combination thereof.

According to one embodiment, the tumor is a primary tumor. According to another embodiment, the tumor is a secondary tumor. According to another embodiment, the tumor is a recurrent tumor. According to another embodiment, the tumor is a tumor refractory to chemotherapy.

According to some embodiments, the primary tumor is a squamous cell carcinoma, an adenocarcinoma, or a large cell carcinoma.

According to the some embodiments, the secondary tumor or site of metastasis is one or more of lung tissue, adrenal tissue, bone tissue, liver tissue or brain tissue.

According to some embodiments, cancer cell death may include, but is not limited to, apoptosis.

According to some embodiments, inhibitory profiles of MMI inhibitors in vivo depend on dosages, routes of administration, and cell types responding to the inhibitors.

According to another embodiment, the pharmaceutical composition is effective to inhibit at least 50% of the kinase activity of the kinase. According to another embodiment, the pharmaceutical composition inhibits at least 65% of the kinase activity of the kinase. According to another embodiment, the pharmaceutical composition inhibits at least 75% of the kinase activity of that kinase. According to another embodiment, the pharmaceutical composition inhibits at least 80% of the kinase activity of that kinase. According to another embodiment, the pharmaceutical composition inhibits at least 85% of the kinase activity of that kinase. According to another embodiment, the pharmaceutical composition inhibits at least 90% of the kinase activity of that kinase. According to another embodiment, the pharmaceutical composition inhibits at least 95% of the kinase activity of that kinase.

According to some embodiments, the pharmaceutical composition is effective to inhibit a kinase activity of Mitogen-Activated Protein Kinase-Activated Protein Kinase 2 (MK2 kinase). According to some other embodiments, the pharmaceutical composition inhibits at least 50% of the kinase activity of MK2 kinase. According to some other embodiments, the pharmaceutical composition inhibits at least 65% of the kinase activity of MK2 kinase. According to another embodiment, the pharmaceutical composition inhibits at least 75% of the kinase activity of MK2 kinase. According to another embodiment, the pharmaceutical composition inhibits at least 80% of the kinase activity of MK2 kinase. According to another embodiment, the pharmaceutical composition inhibits at least 85% of the kinase activity of MK2 kinase. According to another embodiment, the pharmaceutical composition inhibits at least 90% of the kinase activity of MK2 kinase. According to another embodiment, the pharmaceutical composition inhibits at least 95% of the kinase activity of MK2 kinase.

According to another embodiment, the pharmaceutical composition is effective to inhibit a kinase activity of Mitogen-Activated Protein Kinase-Activated Protein Kinase 3 (MK3 kinase). According to another embodiment, the pharmaceutical composition inhibits at least 50% of the kinase activity of MK3 kinase. According to another embodiment, the pharmaceutical composition inhibits at least 65% of the kinase activity of MK3 kinase. According to another embodiment, the pharmaceutical composition inhibits at least 70% of the kinase activity of MK3 kinase. According to another embodiment, the pharmaceutical composition inhibits at least 75% of the kinase activity of MK3 kinase. According to another embodiment, the pharmaceutical composition inhibits at least 80% of the kinase activity of MK3 kinase. According to another embodiment, the pharmaceutical composition inhibits at least 85% of the kinase activity of MK3 kinase. According to another embodiment, the pharmaceutical composition inhibits at least 90% of the kinase activity of MK3 kinase. According to another embodiment, the pharmaceutical composition inhibits at least 95% of the kinase activity of MK3 kinase.

According to another embodiment, the pharmaceutical composition is effective to inhibit a kinase activity of calcium/calmodulin-dependent protein kinase I (CaMKI). According to another embodiment, the pharmaceutical composition further inhibits at least 50% of the kinase activity of $Ca^{2+}$/calmodulin-dependent protein kinase I (CaMKI). According to another embodiment, the pharmaceutical composition further inhibits at least 65% of the kinase activity of $Ca^{2+}$/calmodulin-dependent protein kinase I (CaMKI). According to another embodiment, the pharmaceutical composition further inhibits at least 70% of the kinase activity of $Ca^{2+}$/calmodulin-dependent protein kinase I (CaMKI). According to another embodiment, the pharmaceutical composition further inhibits at least 75% of the kinase activity of $Ca^{2+}$/calmodulin-dependent protein kinase I (CaMKI). According to another embodiment, the pharmaceutical composition further inhibits at least 80% of the kinase activity of $Ca^{2+}$/calmodulin-dependent protein kinase I (CaMKI). According to another embodiment, the pharmaceutical composition further inhibits at least 85% of the kinase activity of $Ca^{2+}$/calmodulin-dependent protein kinase I (CaMKI). According to another embodiment, the pharmaceutical composition further inhibits at least 90% of the kinase activity of $Ca^{2+}$/calmodulin-dependent protein kinase I (CaMKI). According to another embodiment, the pharmaceutical composition further inhibits at least 95% of the kinase activity of $Ca^{2+}$/calmodulin-dependent protein kinase I (CaMKI).

According to another embodiment, the pharmaceutical composition is effective to inhibit a kinase activity of BDNF/NT-3 growth factors receptor (TrkB). According to another embodiment, the pharmaceutical further inhibits at least 50% of the kinase activity of BDNF/NT-3 growth factors receptor (TrkB). According to another embodiment, the pharmaceutical further inhibits at least 65% of the kinase activity of BDNF/NT-3 growth factors receptor (TrkB). According to another embodiment, the pharmaceutical further inhibits at least 70% of the kinase activity of BDNF/NT-3 growth factors receptor (TrkB). According to another embodiment, the pharmaceutical further inhibits at least 75% of the kinase activity of BDNF/NT-3 growth factors receptor (TrkB).

According to another embodiment, the pharmaceutical composition is effective to inhibit a kinase activity of Mitogen-Activated Protein Kinase-Activated Protein Kinase 2 (MK2) and a kinase activity of Mitogen-Activated Protein Kinase-Activated Protein Kinase 3 (MK3).

According to another embodiment, the pharmaceutical composition is effective to inhibit a kinase activity of Mitogen-Activated Protein Kinase-Activated Protein Kinase 2 (MK2) and a kinase activity of calcium/calmodulin-dependent protein kinase I (CaMKI).

According to another embodiment, the pharmaceutical composition is effective to inhibit a kinase activity of Mitogen-Activated Protein Kinase-Activated Protein Kinase 2 (MK2) and a kinase activity of BDNF/NT-3 growth factors receptor (TrkB).

According to another embodiment, the pharmaceutical composition is effective to inhibit a kinase activity of Mitogen-Activated Protein Kinase-Activated Protein Kinase 2 (MK2), a kinase activity of Mitogen-Activated Protein Kinase-Activated Protein Kinase 3 (MK3), a kinase activity of calcium/calmodulin-dependent protein kinase I (CaMKI), and a kinase activity of BDNF/NT-3 growth factors receptor (TrkB).

According to another embodiment, the pharmaceutical composition is effective to inhibit a kinase activity of Mitogen-Activated Protein Kinase-Activated Protein Kinase 2 (MK2), a kinase activity of calcium/calmodulin-dependent protein kinase I (CaMKI), and a kinase activity of BDNF/NT-3 growth factors receptor (TrkB).

According to another embodiment, the pharmaceutical composition is effective to inhibit at least 65% of the kinase activity of Mitogen-Activated Protein Kinase-Activated Protein Kinase 2 (MK2).

According to another embodiment, the pharmaceutical composition is effective to inhibit at least 65% of the kinase activity of Mitogen-Activated Protein Kinase-Activated Protein Kinase 3 (MK3).

According to another embodiment, the pharmaceutical composition is effective to inhibit at least 65% of the kinase activity of calcium/calmodulin-dependent protein kinase I (CaMKI).

According to another embodiment, the pharmaceutical composition is effective to inhibit at least 65% of the kinase activity of BDNF/NT-3 growth factors receptor (TrkB).

According to another embodiment, the pharmaceutical composition is effective to inhibit at least 65% of the kinase activity of Mitogen-Activated Protein Kinase-Activated Protein Kinase 2 (MK2) and at least 65% of the kinase activity of Mitogen-Activated Protein Kinase-Activated Protein Kinase 3 (MK3).

According to another embodiment, the pharmaceutical composition is effective to inhibit at least 65% of the kinase activity of Mitogen-Activated Protein Kinase-Activated Protein Kinase 2 (MK2) and at least 65% of the kinase activity of calcium/calmodulin-dependent protein kinase I (CaMKI).

According to another embodiment, the pharmaceutical composition is effective to inhibit at least 65% of the kinase activity of Mitogen-Activated Protein Kinase-Activated Protein Kinase 2 (MK2) and at least 65% of the kinase activity of BDNF/NT-3 growth factors receptor (TrkB).

According to another embodiment, the pharmaceutical composition is effective to inhibit at least 65% of the kinase activity of Mitogen-Activated Protein Kinase-Activated Protein Kinase 2 (MK2), at least 65% of the kinase activity of Mitogen-Activated Protein Kinase-Activated Protein Kinase 3 (MK3), at least 65% of the kinase activity of calcium/calmodulin-dependent protein kinase I (CaMKI), and at least 65% of the kinase activity of BDNF/NT-3 growth factors receptor (TrkB).

According to another embodiment, the pharmaceutical composition is effective to inhibit the kinase activity of at least one kinase selected from the group of MK2, MK3, CaMKI, TrkB, without substantially inhibiting the activity of one or more other selected kinases from the remaining group listed in Table 1 herein.

According to some embodiments, inhibitory profiles of MMI inhibitors in vivo depend on dosages, routes of administration, and cell types responding to the inhibitors.

According to such embodiments, the pharmaceutical composition is effective to inhibit less than 50% of the kinase activity of the other selected kinase(s). According to such embodiment, the pharmaceutical composition is effective to inhibit less than 65% of the kinase activity of the other selected kinase(s). According to another embodiment, the pharmaceutical composition is effective to inhibit less than 50% of the kinase activity of the other selected kinase(s). According to another embodiment, the pharmaceutical composition is effective to inhibit less than 40% of the kinase activity of the other selected kinase(s). According to another embodiment, the pharmaceutical composition is effective to inhibit less than 20% of the kinase activity of the other selected kinase(s). According to another embodiment, the pharmaceutical composition is effective to inhibit less than 15% of the kinase activity of the other selected kinase(s). According to another embodiment, the pharmaceutical composition is effective to inhibit less than 10% of the kinase activity of the other selected kinase(s). According to another embodiment, the pharmaceutical composition is effective to inhibit less than 5% of the kinase activity of the other selected kinase(s). According to another embodiment, the pharmaceutical composition is effective to inhibit the kinase activity of the other selected kinases.

According to the embodiments of the immediately preceding paragraph, the one or more other selected kinase not substantially inhibited is a kinase selected from the group of $Ca^{2+}$/calmodulin-dependent protein kinase II (CaMKII, including its subunit CaMKIIδ), Proto-oncogene serine/threonine-protein kinase (PIM-1), cellular-Sarcoma (c-SRC), Spleen Tyrosine Kinase (SYK), C-src Tyrosine Kinase (CSK), and Insulin-like Growth Factor 1 Receptor (IGF-1R).

According to some embodiments, the pharmaceutical composition further comprises at least one additional therapeutic agent.

According to some such embodiments, the additional therapeutic agent is a chemotherapeutic agent. Examples of chemotherapeutic agents include, but are not limited to, Abitrexate (Methotrexate), Abraxane (Paclitaxel Albumin-stabilized Nanoparticle Formulation), Afatinib Dimaleate, Alimta (Pemetrexed Disodium), Avastin (Bevacizumab), Bvacizumab, Carboplatin, Ceritinib, Cisplatin, Crizotinib, Cyramza (Ramucirumab), Docetaxel, Erlotinib Hydrochloride, Folex PFS (Methotrexate), Gefitinib, Gilotrif (Afatinib Dmaleate), Gemcitabine Hydrochloride, Gemzar (Gemcitabine Hydrochloride), Iressa (Gefitinib), Mechlorethamine Hydrochloride, Methotrexate, Methotrexate LPF (Methotrexate), Mexate (Methotrexate), Mexate-AQ (Methotrexate), Mustargen (mechlorethamine Hydrochloride), Navelbine (Vinorelbine Tartrate), Paclitaxel, Paclitaxel Albumin-stabilized nanoparticle Formulation, Paraplat (Carboplatin), Paraplatin (Carboplatin), Pemetrexed Disodium, Platinol (Cisplatin), Platinol-AQ (Cisplatin), Ramucirumab, Tarceva (Erlotinib Hydrochloride), Taxol (Paclitaxel), Taxotere (Docetaxel), Vinorelbine Tartrate, Xalkori (Crizotinib), Zykadia (Ceritinib), Carboplatin-Taxol, and Gemcitabine-Cisplatin.

According to another embodiment, the additional therapeutic agent is an analgesic agent. According to some embodiments, the analgesic agent relieves pain by elevating the pain threshold without disturbing consciousness or altering other sensory modalities. According to some such embodiments, the analgesic agent is a non-opioid analgesic. "Non-opioid analgesics" are natural or synthetic substances that reduce pain but are not opioid analgesics. Examples of non-opioid analgesics include, but are not limited to, etodolac, indomethacin, sulindac, tolmetin, nabumetone, piroxicam, acetaminophen, fenoprofen, flurbiprofen, ibuprofen, ketoprofen, naproxen, naproxen sodium, oxaprozin, aspirin, choline magnesium trisalicylate, diflunisal, meclofenamic acid, mefenamic acid, and phenylbutazone. According to some other embodiments, the analgesic is an opioid analgesic. "Opioid analgesics", "opioid", or "narcotic analgesics" are natural or synthetic substances that bind to opioid receptors in the central nervous system, producing an agonist action. Examples of opioid analgesics include, but are not limited to, codeine, fentanyl, hydromorphone, levorphanol, meperidine, methadone, morphine, oxycodone, oxymorphone, propoxyphene, buprenorphine, butorphanol, dezocine, nalbuphine, and pentazocine.

According to another embodiment, the additional therapeutic agent is an anti-infective agent. According to another embodiment, the anti-infective agent is an antibiotic agent. The term "antibiotic agent" as used herein means any of a group of chemical substances having the capacity to inhibit the growth of, or to destroy bacteria and other microorganisms, used chiefly in the treatment of infectious diseases. Examples of antibiotic agents include, but are not limited to, Penicillin G; Methicillin; Nafcillin; Oxacillin; Cloxacillin; Dicloxacillin; Ampicillin; Amoxicillin; Ticarcillin; Carbenicillin; Mezlocillin; Azlocillin; Piperacillin; Imipenem; Aztreonam; Cephalothin; Cefaclor; Cefoxitin; Cefuroxime; Cefonicid; Cefmetazole; Cefotetan; Cefprozil; Loracarbef; Cefetamet; Cefoperazone; Cefotaxime; Ceftizoxime; Ceftriaxone; Ceftazidime; Cefepime; Cefixime; Cefpodoxime; Cefsulodin; Fleroxacin; Nalidixic acid; Norfloxacin; Ciprofloxacin; Ofloxacin; Enoxacin; Lomefloxacin; Cinoxacin; Doxycycline; Minocycline; Tetracycline; Amikacin; Gentamicin; Kanamycin; Netilmicin; Tobramycin; Streptomycin; Azithromycin; Clarithromycin; Erythromycin; Erythromycin estolate; Erythromycin ethyl succinate; Erythromycin glucoheptonate; Erythromycin lactobionate; Erythromycin stearate; Vancomycin; Teicoplanin; Chloramphenicol; Clindamycin; Trimethoprim; Sulfamethoxazole; Nitrofurantoin; Rifampin; Mupirocin; Metronidazole; Cephalexin; Roxithromycin; Co-amoxiclavuanate; combinations of Piperacillin and Tazobactam; and their various salts, acids, bases, and other derivatives. Anti-bacterial antibiotic agents include, but are not limited to, penicillins, cephalosporins, carbacephems, cephamycins, carbapenems, monobactams, aminoglycosides, glycopeptides, quinolones, tetracyclines, macrolides, and fluoroquinolones.

According to some other embodiments, the additional therapeutic agent comprises a bronchodilator including, but not limited to, a leukotriene modifier, an anticholinergic bronchodilator, a β2-agonist, or a combination thereof.

According to another embodiment, the additional therapeutic agent comprises a corticosteroid including, but not limited to, prednisone, budesonide, mometasone, beclemethasone, or a combination thereof.

According to some other embodiments, the additional therapeutic agent comprises a bronchodilator including, but not limited to, a leukotriene modifier, an anticholinergic bronchodilator, a β2-agonist, or a combination thereof.

According to another embodiment, the additional therapeutic agent comprises a corticosteroid including, but not limited to, prednisone, budesonide, mometasone, beclemethasone, or a combination thereof.

According to another embodiment, the additional therapeutic agent is an anti-inflammatory agent.

According to another embodiment, the anti-inflammatory agent is a nonsteroidal anti-inflammatory agent. Mixtures of non-steroidal anti-inflammatory agents also may be employed.

According to another embodiment, the nonsteroidal anti-inflammatory agent comprises Transforming Growth Factor-β3 (TGF-β3), an anti-Tumor Necrosis Factor-alpha (TNF-α) agent, or a combination thereof.

According to another embodiment, the anti-inflammatory agent is a steroidal anti-inflammatory agent. According to another embodiment, the steroidal anti-inflammatory agent comprises at least one corticosteroid selected from the group consisting of prednisone, budesonide, mometasone, beclemethasone, and a combination thereof.

According to another embodiment, the additional therapeutic agent comprises a methylxanthine.

According to another embodiment, the additional therapeutic agent comprises a neutrophil elastase inhibitor.

According to another embodiment, the additional therapeutic agent is at least one neutrophil elastase inhibitor, including, but not limited to, ICI 200355, ONO-5046, MR-889, L-694,458, CE-1037, GW-311616, TEI-8362, ONO-6818, AE-3763, FK-706, ICI-200,880, ZD-0892, ZD-8321, and a combination thereof.

According to another embodiment, the additional therapeutic agent comprises at least one phosphodiesterase inhibitor, including, but not limited to, phosphodiesterase 4 inhibitor. Examples of phosphodiesterase 4 inhibitors include, but are not limited to, roflumilast, cilomilast or a combination thereof.

According to some embodiments, the functional equivalent of the polypeptide YARAAARQARAKALARQLGVAA (SEQ ID NO: 1) has a substantial sequence identity to amino acid sequence YARAAARQARAKALARQLGVAA (SEQ ID NO: 1).

According to another embodiment, the functional equivalent of the polypeptide YARAAARQARAKALARQLGVAA (SEQ ID NO: 1) has at least 70 percent sequence identity to amino acid sequence YARAAARQARAKALARQLGVAA (SEQ ID NO: 1). According to another embodiment, the functional equivalent of the polypeptide YARAAARQARAKALARQLGVAA (SEQ ID NO: 1) has at least 80 percent sequence identity to amino acid sequence YARAAARQARAKALARQLGVAA (SEQ ID NO: 1). According to another embodiment, the functional equivalent of the polypeptide YARAAARQARAKALARQLGVAA (SEQ ID NO: 1) has at least 90 percent sequence identity to amino acid sequence YARAAARQARAKALARQLGVAA (SEQ ID NO: 1). According to another embodiment, the functional equivalent of the polypeptide YARAAARQARAKALARQLGVAA (SEQ ID NO: 1) has at least 95 percent sequence identity to amino acid sequence YARAAARQARAKALARQLGVAA (SEQ ID NO: 1).

According to another embodiment, the functional equivalent of the polypeptide YARAAARQARAKALARQLGVAA (SEQ ID NO: 1) is of amino acid sequence FAKLAARLYRKALARQLGVAA (SEQ ID NO: 3).

According to another embodiment, the functional equivalent of the polypeptide YARAAARQARAKALARQLGVAA (SEQ ID NO: 1) is of amino acid sequence KAFAKLAARLYRKALARQLGVAA (SEQ ID NO: 4).

According to another embodiment, the functional equivalent of the polypeptide YARAAARQARAKALARQLGVAA (SEQ ID NO: 1) is of amino acid sequence YARAAARQARAKALARQLAVA (SEQ ID NO: 5).

According to another embodiment, the functional equivalent of the polypeptide YARAAARQARAKALARQLGVAA (SEQ ID NO: 1) is of amino acid sequence YARAAARQARAKALARQLGVA (SEQ ID NO: 6).

According to another embodiment, the functional equivalent of the polypeptide YARAAARQARAKALARQLGVAA (SEQ ID NO: 1) is of amino acid sequence HRRIKAWLKKIKALARQLGVAA (SEQ ID NO: 7).

According to some other embodiments, the functional equivalent of the polypeptide YARAAARQARAKALARQLGVAA (SEQ ID NO: 1) is a fusion protein comprising a first polypeptide operatively linked to a second polypeptide, wherein the first polypeptide is of amino acid sequence YARAAARQARA (SEQ ID NO: 11), and the second polypeptide comprises a therapeutic domain whose sequence has substantial identity to amino acid sequence KALARQLGVAA (SEQ ID NO: 2).

According to some such embodiments, the second polypeptide has at least 70 percent sequence identity to amino acid sequence KALARQLGVAA (SEQ ID NO: 2). According some other embodiments, the second polypeptide has at least 80 percent sequence identity to amino acid sequence KALARQLGVAA (SEQ ID NO: 2). According to some other embodiments, the second polypeptide has at least 90 percent sequence identity to amino acid sequence KALARQLGVAA (SEQ ID NO: 2). According to some other embodiments, the second polypeptide has at least 95 percent sequence identity to amino acid sequence KALARQLGVAA (SEQ ID NO: 2).

According to some embodiments, the second polypeptide is a polypeptide of amino acid sequence KALARQLAVA (SEQ ID NO: 8).

According to another embodiment, the second polypeptide is a polypeptide of amino acid sequence KALARQLGVA (SEQ ID NO: 9).

According to another embodiment, the second polypeptide is a polypeptide of amino acid sequence KALARQLGVAA (SEQ ID NO: 10).

According to some other embodiments, the functional equivalent of the polypeptide YARAAARQARAKALARQLGVAA (SEQ ID NO: 1) is a fusion protein comprising a first polypeptide operatively linked to a second polypeptide, wherein the first polypeptide comprises a cell penetrating peptide functionally equivalent to YARAAARQARA (SEQ ID NO: 11), and the second polypeptide is of amino acid sequence KALARQLGVAA (SEQ ID NO: 2).

According to another embodiment, the first polypeptide is a polypeptide of amino acid sequence WLRRIKAWLRRIKA (SEQ ID NO: 12). According to another embodiment, the first polypeptide is a polypeptide of amino acid sequence WLRRIKA (SEQ ID NO: 13). According to another embodiment, the first polypeptide is a polypeptide of amino acid sequence YGRKKRRQRRR (SEQ ID NO: 14).

According to another embodiment, the first polypeptide is a polypeptide of amino acid sequence WLRRIKAWLRRI (SEQ ID NO: 15). According to another embodiment, the first polypeptide is a polypeptide of amino acid sequence FAKLAARLYR (SEQ ID NO: 16). According to another embodiment, the first polypeptide is a polypeptide of amino acid sequence KAFAKLAARLYR (SEQ ID NO: 17). According to another embodiment, the first polypeptide is a polypeptide of amino acid sequence HRRIKAWLKKI (SEQ ID NO: 18).

According to another aspect, the described invention also provides an isolated nucleic acid that encodes a protein sequence with at least 70% amino acid sequence identity to amino acid sequence YARAAARQARAKALARQLGVAA (SEQ ID NO: 1). According to some embodiments, the isolated nucleic acid encodes a protein sequence with at least 80% amino acid sequence identity to amino acid sequence YARAAARQARAKALARQLGVAA (SEQ ID NO: 1). According to some other embodiments, the isolated nucleic acid encodes a protein sequence with at least 90% amino acid sequence identity to amino acid sequence YARAAARQARAKALARQLGVAA (SEQ ID NO: 1). According to some other embodiments, the isolated nucleic acid encodes a protein sequence with at least 95% amino acid sequence identity to amino acid sequence YARAAARQARAKALARQLGVAA (SEQ ID NO: 1).

According to some other embodiments, the therapeutic amount of therapeutic inhibitor peptide of the pharmaceutical composition is of an amount from about 0.000001 mg/kg body weight to about 100 mg/kg body weight. According to another embodiment, the therapeutic amount of therapeutic inhibitory peptide of the pharmaceutical composition is of an amount from about 0.00001 mg/kg body weight to about 100 mg/kg body weight. According to another embodiment, the therapeutic amount of therapeutic inhibitory peptide of the pharmaceutical composition is of an amount from about 0.0001 mg/kg body weight to about 100 mg/kg body weight. According to another embodiment, the therapeutic amount of therapeutic inhibitory peptide of the pharmaceutical composition is of an amount from about 0.001 mg/kg body weight to about 10 mg/kg body weight. According to another embodiment, the therapeutic amount of therapeutic inhibitory peptide of the pharmaceutical composition is of an amount from about 0.01 mg/kg body weight to about 10 mg/kg body weight. According to another embodiment, the therapeutic amount of therapeutic inhibitory peptide of the pharmaceutical composition is of an amount from about 0.1 mg/kg (or 100 µg/kg) body weight to about 10 mg/kg body weight. According to another embodiment, the therapeutic amount of therapeutic inhibitory peptide of the pharmaceutical composition is of an amount from about 1 mg/kg body weight to about 10 mg/kg body weight. According to another embodiment, the therapeutic amount of therapeutic inhibitory peptide of the pharmaceutical composition is of an amount from about 10 mg/kg body weight to about 100 mg/kg body weight. According to another embodiment, the therapeutic amount of therapeutic inhibitory peptide of the pharmaceutical composition is of an amount from about 2 mg/kg body weight to about 10 mg/kg body weight. According to another embodiment, the therapeutic amount of therapeutic inhibitory peptide of the pharmaceutical composition is of an amount from about 3 mg/kg body weight to about 10 mg/kg body weight. According to another embodiment, the therapeutic amount of therapeutic inhibitory peptide of the pharmaceutical composition is of an amount from about 4 mg/kg body weight to about 10 mg/kg body weight. According to another embodiment, the therapeutic amount of therapeutic inhibitory peptide of the pharmaceutical composition is of an amount from about 5 mg/kg body weight to about 10 mg/kg body weight. According to another embodiment, the therapeutic amount of therapeutic inhibitory peptide of the pharmaceutical composition is of an amount from about 60 mg/kg body weight to about 100 mg/kg body weight. According to another embodiment, the therapeutic amount of therapeutic inhibitory peptide of the pharmaceutical composition is of an amount from about 70 mg/kg body weight to about 100 mg/kg body weight. According to another embodiment, the therapeutic amount of therapeutic inhibitory peptide of the pharmaceutical composition is of an amount from about 80 mg/kg body weight to about 100 mg/kg body weight. According to another embodiment, the therapeutic amount of therapeutic inhibitory peptide of the pharmaceutical composition is of an amount from about 90 mg/kg body weight to about 100 mg/kg body weight. According to another embodiment, the therapeutic amount of therapeutic inhibitor peptide of the pharmaceutical composition is of an amount from about 0.000001 mg/kg body weight to about 90 mg/kg body weight. According to another embodiment, the therapeutic amount of therapeutic inhibitor peptide of the pharmaceutical composition is of an amount from about 0.000001 mg/kg body weight to about 80 mg/kg body weight. According to another embodiment, the therapeutic amount of therapeutic inhibitor peptide of the pharmaceutical composition is of an amount from about 0.000001 mg/kg body weight to about 70 mg/kg body weight. According to another embodiment, the therapeutic amount of therapeutic inhibitor peptide of the pharmaceutical composition is of an amount from about 0.000001 mg/kg body weight to about 60 mg/kg body weight. According to another embodiment, the therapeutic amount of therapeutic inhibitor peptide of the pharmaceutical composition is of an amount from about 0.000001 mg/kg body weight to about 50 mg/kg body weight. According to another embodiment, the therapeutic amount of therapeutic inhibitor peptide of the pharmaceutical composition is of an amount from about 0.000001 mg/kg body weight to about 40 mg/kg body weight. According to another embodiment, the therapeutic amount of therapeutic inhibitor peptide is of an amount from about 0.000001 mg/kg body weight to about 30 mg/kg body weight. According to another embodiment, the therapeutic amount of therapeutic inhibitor peptide of the pharmaceutical composition is of an amount from about 0.000001 mg/kg body weight to about 20 mg/kg body weight. According to another embodiment, the therapeutic amount of therapeutic inhibitor peptide of the pharmaceutical composition is of an amount from about 0.000001 mg/kg body weight to about 10 mg/kg body weight. According to another embodiment, the therapeutic amount of therapeutic inhibitor peptide of the pharmaceutical composition is of an amount from about 0.000001 mg/kg body weight to about 1 mg/kg body weight. According to another embodiment, the therapeutic amount of therapeutic inhibitor peptide of the pharmaceutical composition is of an amount from about 0.000001 mg/kg body weight to about 0.1 mg/kg body weight. According to another embodiment, the therapeutic amount of therapeutic inhibitor peptide of the pharmaceutical composition is of an amount from about 0.000001 mg/kg body weight to about 0.1 mg/kg body weight. According to another embodiment, the therapeutic amount of therapeutic inhibitor peptide of the pharmaceutical composition is of an amount from about 0.000001 mg/kg body weight to about 0.01 mg/kg body weight. According to another embodiment, the therapeutic amount of therapeutic inhibitor peptide of the pharmaceutical composition is of an amount from about 0.000001 mg/kg body weight to about 0.001 mg/kg body weight. According to another embodiment, the therapeutic amount of therapeutic inhibitor peptide of the pharmaceutical composition is of an amount from about 0.000001 mg/kg body weight to about 0.0001 mg/kg body weight. According to another embodiment, the therapeutic amount of therapeutic inhibitor peptide of the pharmaceutical composition is of an amount from about 0.000001 mg/kg body weight to about 0.00001 mg/kg body weight.

According to some other embodiments, the therapeutic dose of therapeutic inhibitor peptide of the pharmaceutical composition ranges from 1 µg/kg/day to 25 µg/kg/day. According to some other embodiments, the therapeutic dose of therapeutic inhibitor peptide of the pharmaceutical composition ranges from 1 µg/kg/day to 2 µg/kg/day. According to some other embodiments, the therapeutic dose of therapeutic inhibitor peptide of the pharmaceutical composition ranges from 2 µg/kg/day to 3 µg/kg/day. According to some other embodiments, the therapeutic dose of therapeutic inhibitor peptide of the pharmaceutical composition ranges from 3 µg/kg/day to 4 µg/kg/day. According to some other embodiments, the therapeutic dose of therapeutic inhibitor peptide of the pharmaceutical ranges from 4 µg/kg/day to 5 µg/kg/day. According to some other embodiments, the therapeutic dose of therapeutic inhibitor peptide of the pharmaceutical composition ranges from 5 µg/kg/day to 6 µg/kg/day. According to some other embodiments, the therapeutic dose of therapeutic inhibitor peptide of the pharmaceutical composition ranges from 6 µg/kg/day to 7 µg/kg/day. According to some other embodiments, the therapeutic dose of therapeutic inhibitor peptide of the pharmaceutical composition ranges from 7 µg/kg/day to 8 µg/kg/day. According to some other embodiments, the therapeutic dose of therapeutic inhibitor peptide of the pharmaceutical composition ranges from 8 µg/kg/day to 9 µg/kg/day. According to some other embodiments, the therapeutic dose of therapeutic inhibitor peptide of the pharmaceutical composition ranges from 9 µg/kg/day to 10 µg/kg/day. According to some other embodiments, the therapeutic dose of therapeutic inhibitor peptide of the pharmaceutical composition ranges from 1 µg/kg/day to 5 µg/kg/day. According to some other embodiments, the therapeutic dose of therapeutic inhibitor peptide of the pharmaceutical composition ranges from 5 µg/kg/day to 10 µg/kg/day. According to some other embodiments, the therapeutic dose of therapeutic inhibitor peptide of the pharmaceutical composition ranges from 10 µg/kg/day to 15 µg/kg/day. According to some other embodiments, the therapeutic dose of therapeutic inhibitor peptide of the pharmaceutical composition ranges from 15 µg/kg/day to 20 µg/kg/day. According to some other embodiments, the therapeutic dose of therapeutic inhibitor peptide of the pharmaceutical composition ranges from 25 µg/kg/day to 30 µg/kg/day. According to some other embodiments, the therapeutic dose of therapeutic inhibitor peptide of the pharmaceutical composition ranges from 30 µg/kg/day to 35 µg/kg/day. According to some other embodiments, the therapeutic dose of therapeutic inhibitor peptide of the pharmaceutical composition ranges from 35 µg/kg/day to 40 µg/kg/day. According to some other embodiments, the therapeutic dose of therapeutic inhibitor peptide of the pharmaceutical composition ranges from 40 µg/kg/day to 45 µg/kg/day. According to some other embodiments, the therapeutic dose of therapeutic inhibitor peptide of the pharmaceutical composition ranges from 45 µg/kg/day to 50 µg/kg/day. According to some other embodiments, the therapeutic dose of therapeutic inhibitor peptide of the pharmaceutical composition ranges from 50

μg/kg/day to 55 μg/kg/day. According to some other embodiments, the therapeutic dose of therapeutic inhibitor peptide of the pharmaceutical composition ranges from 55 μg/kg/day to 60 μg/kg/day. According to some other embodiments, the therapeutic dose of therapeutic inhibitor peptide of the pharmaceutical composition ranges from 60 μg/kg/day to 65 μg/kg/day. According to some other embodiments, the therapeutic dose of therapeutic inhibitor peptide of the pharmaceutical composition ranges from 65 μg/kg/day to 70 μg/kg/day. According to some other embodiments, the therapeutic dose of therapeutic inhibitor peptide of the pharmaceutical composition ranges from 70 μg/kg/day to 75 μg/kg/day. According to some other embodiments, the therapeutic dose of therapeutic inhibitor peptide of the pharmaceutical composition ranges from 80 μg/kg/day to 85 μg/kg/day. According to some other embodiments, the therapeutic dose of therapeutic inhibitor peptide of the pharmaceutical composition ranges from 85 μg/kg/day to 90 μg/kg/day. According to some other embodiments, the therapeutic dose of therapeutic inhibitor peptide of the pharmaceutical composition ranges from 90 μg/kg/day to 95 μg/kg/day. According to some other embodiments, the therapeutic dose of therapeutic inhibitor peptide of the pharmaceutical composition ranges from 95 μg/kg/day to 100 μg/kg/day.

According to another embodiment, the therapeutic dose of therapeutic inhibitor peptide of the pharmaceutical composition is 1 μg/kg/day.

According to another embodiment, the therapeutic dose of therapeutic inhibitor peptide of the pharmaceutical composition is 2 μg/kg/day.

According to another embodiment, the therapeutic dose of therapeutic inhibitor peptide of the pharmaceutical composition is 5 μg/kg/day.

According to another embodiment, the therapeutic dose of therapeutic inhibitor peptide of the pharmaceutical composition is 10 μg/kg/day.

According to some embodiments, the polypeptide of the invention comprises D-amino acids (which are resistant to L-amino acid-specific proteases in vivo), a combination of D- and L-amino acids, and various "designer" amino acids (e.g., β-methyl amino acids, C-α-methyl amino acids, and N-α-methyl amino acids, etc.) to convey special properties. Examples of synthetic amino acid substitutions include ornithine for lysine, and norleucine for leucine or isoleucine.

According to some embodiments, the polypeptide may be linked to other compounds to promote an increased half-life in vivo, such as polyethylene glycol or dextran. Such linkage can be covalent or non-covalent as is understood by those of skill in the art. According to some other embodiments, the polypeptide may be encapsulated in a micelle such as a micelle made of poly(ethyleneglycol)-block-poly(polypropylenglycol) or poly(ethyleneglycol)-block-polylactide. According to some other embodiments, the polypeptide may be encapsulated in degradable nano- or micro-particles composed of degradable polyesters including, but not limited to, polylactic acid, polyglycolide, and polycaprolactone.

According to another embodiment, the polypeptide may be prepared in a solid form (including granules, powders or suppositories) or in a liquid form (e.g., solutions, suspensions, or emulsions).

According to another embodiment, the compositions of the described invention may be in the form of a dispersible dry powder for delivery by inhalation or insufflation (either through the mouth or through the nose, respectively). Dry powder compositions may be prepared by processes known in the art, such as lyophilization and jet milling, as disclosed in International Patent Publication No. WO 91/16038 and as disclosed in U.S. Pat. No. 6,921,527, the disclosures of which are incorporated by reference. The composition of the described invention is placed within a suitable dosage receptacle in an amount sufficient to provide a subject with a unit dosage treatment. The dosage receptacle is one that fits within a suitable inhalation device to allow for the aerosolization of the dry powder composition by dispersion into a gas stream to form an aerosol and then capturing the aerosol so produced in a chamber having a mouthpiece attached for subsequent inhalation by a subject in need of treatment. Such a dosage receptacle includes any container enclosing the composition known in the art such as gelatin or plastic capsules with a removable portion that allows a stream of gas (e.g., air) to be directed into the container to disperse the dry powder composition. Such containers are exemplified by those shown in U.S. Pat. Nos. 4,227,522; 4,192,309; and 4,105,027. Suitable containers also include those used in conjunction with Glaxo's Ventolin® Rotohaler brand powder inhaler or Fison's Spinhaler® brand powder inhaler. Another suitable unit-dose container which provides a superior moisture barrier is formed from an aluminum foil plastic laminate. The pharmaceutical-based powders is filled by weight or by volume into the depression in the formable foil and hermetically sealed with a covering foil-plastic laminate. Such a container for use with a powder inhalation device is described in U.S. Pat. No. 4,778,054 and is used with Glaxo's Diskhaler® (U.S. Pat. Nos. 4,627,432; 4,811,731; and 5,035,237). All of these references are incorporated herein by reference in their entireties.

According to another embodiment, the carrier of the composition of the described invention includes a release agent, such as a sustained release or delayed release carrier. In such embodiments, the carrier can be any material capable of sustained or delayed release of the polypeptide to provide a more efficient administration, e.g., resulting in less frequent and/or decreased dosage of the polypeptide, improving ease of handling, and extending or delaying effects on diseases, disorders, conditions, syndromes, and the like, being treated, prevented or promoted. Non-limiting examples of such carriers include liposomes, microsponges, microspheres, or microcapsules of natural and synthetic polymers and the like. Liposomes may be formed from a variety of phospholipids, including, but not limited to, cholesterol, stearylamines or phosphatidylcholines.

Methods for synthesis and preparation of small peptides are well known in the art and are disclosed, for example, in U.S. Pat. Nos. 5,352,461; 5,503,852; 6,071,497; 6,331,318; 6,428,771 and U.S. Publication No. 20060040953. U.S. Pat. Nos. 6,444,226 and 6,652,885 describe preparing and providing microparticles of diketopiperazines in aqueous suspension to which a solution of active agent is added in order to bind the active agent to the particle. These patents further describe a method of removing a liquid medium by lyophilization to yield microparticles comprising an active agent. Altering the solvent conditions of such suspension to promote binding of the active agent to the particle is disclosed in U.S. Application No. 60/717,524; Ser. Nos. 11/532,063; and 11/532,065; U.S. Pat. No. 6,440,463; and U.S. application Ser. Nos. 11/210,709 and 11/208,087. Each of these patents and patent applications is incorporated by reference herein.

According to some embodiments, MMI-0100 (YARAAARQARAKALARQLGVAA; SEQ ID NO: 1) and its functional equivalents of the present invention can be dried by a method of spraying drying as disclosed in, for example, U.S. application Ser. No. 11/678,046 (incorporated by reference herein).

According to another embodiment, the polypeptide of the invention may be applied in a variety of solutions. A suitable formulation is sterile, dissolves sufficient amounts of the polypeptides, and is not harmful for the proposed application. For example, the compositions of the described invention may be formulated as aqueous suspensions wherein the active ingredient(s) is (are) in admixture with excipients suitable for the manufacture of aqueous suspensions.

Such excipients include, without limitation, suspending agents (e.g., sodium carboxymethylcellulose, methylcellulose, hydroxy-propylmethylcellulose, sodium alginate, polyvinylpyrrolidone, gum tragacanth, and gum acacia), dispersing or wetting agents including, a naturally-occurring phosphatide (e.g., lecithin), or condensation products of an alkylene oxide with fatty acids (e.g., polyoxyethylene stearate), or condensation products of ethylene oxide with long chain aliphatic alcohols (e.g., heptadecaethyl-eneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate).

Compositions of the described invention also may be formulated as oily suspensions by suspending the active ingredient in a vegetable oil (e.g., *arachis* oil, olive oil, sesame oil or coconut oil) or in a mineral oil (e.g., liquid paraffin). The oily suspensions may contain a thickening agent (e.g., beeswax, hard paraffin or cetyl alcohol).

Compositions of the described invention also may be formulated in the form of dispersible powders and granules suitable for preparation of an aqueous suspension by the addition of water. The active ingredient in such powders and granules is provided in admixture with a dispersing or wetting agent, suspending agent, and one or more preservatives. Suitable dispersing or wetting agents and suspending agents are exemplified by those already mentioned above. Additional excipients also may be present.

According to some embodiments, the dry powder is produced by a spray drying process.

According to some other embodiments, the dry powder is produced by micronization According to another embodiment, the dry powder comprises microparticles with Mass Median Aerodynamic Diameter (MMAD) of 1 to 5 microns.

According to another embodiment, the dry powder comprises microparticles with Mass Median Aerodynamic Diameter (MMAD) of about 2 micron.

According to another embodiment, the pharmaceutical composition is packaged in an inhalation device, including, for example, but not limited to a nebulizer, a metered-dose inhaler (MDI), and a dry powder inhaler (DPI).

According to some other embodiments, the pharmaceutical composition is a liquid for aerosolized delivery using a nebulizer. According to some such embodiments, the flowrate of the pharmaceutical composition is at least 0.3 ml/min, and the pharmaceutical composition is delivered as 2 mm particles, with distribution into deepest alveoli.

Compositions of the described invention also may be in the form of an emulsion. An emulsion is a two-phase system prepared by combining two immiscible liquid carriers, one of which is disbursed uniformly throughout the other and consists of globules that have diameters equal to or greater than those of the largest colloidal particles. The globule size is critical and must be such that the system achieves maximum stability. Usually, separation of the two phases will not occur unless a third substance, an emulsifying agent, is incorporated. Thus, a basic emulsion contains at least three components, the two immiscible liquid carriers and the emulsifying agent, as well as the active ingredient. Most emulsions incorporate an aqueous phase into a non-aqueous phase (or vice versa). However, it is possible to prepare emulsions that are basically non-aqueous, for example, anionic and cationic surfactants of the non-aqueous immiscible system glycerin and olive oil. Thus, the compositions of the invention may be in the form of an oil-in-water emulsion. The oily phase may be a vegetable oil, for example, olive oil or arachis oil, or a mineral oil, for example a liquid paraffin, or a mixture thereof. Suitable emulsifying agents may be naturally-occurring gums, for example, gum acacia or gum tragacanth, naturally-occurring phosphatides, for example soy bean, lecithin, and esters or partial esters derived from fatty acids and hexitol anhydrides, for example sorbitan monooleate, and condensation products of the partial esters with ethylene oxide, for example, polyoxyethylene sorbitan monooleate.

Compositions of the described invention also may be formulated with or without mannitol.

According to some embodiments, the polypeptide of the described invention is chemically synthesized. Such a synthetic polypeptide, prepared using the well known techniques of solid phase, liquid phase, or peptide condensation techniques, or any combination thereof, may include natural and unnatural amino acids. Amino acids used for peptide synthesis may be standard Boc (N-α-amino protected N-α-t-butyloxycarbonyl) amino acid resin with the standard deprotecting, neutralization, coupling and wash protocols of the original solid phase procedure of Merrifield (1963, *J. Am. Chem. Soc.* 85:2149-2154), or the base-labile N-α-amino protected 9-fluorenylmethoxycarbonyl (Fmoc) amino acids first described by Carpino and Han (1972, *J. Org. Chem.* 37:3403-3409). Both Fmoc and Boc N-α-amino protected amino acids can be obtained from Sigma, Cambridge Research Biochemical, or other chemical companies familiar to those skilled in the art. In addition, the polypeptide may be synthesized with other N-α-protecting groups that are familiar to those skilled in this art. Solid phase peptide synthesis may be accomplished by techniques familiar to those in the art and provided, for example, in Stewart and Young, 1984, *Solid Phase Synthesis*, Second Edition, Pierce Chemical Co., Rockford, Ill.; Fields and Noble, 1990, *Int. J. Pept. Protein Res.* 35:161-214, or using automated synthesizers, each incorporated by reference herein in its entirety.

II. Methods for Treating Non-Small Cell Lung Cancer (NSCLC)

According to another aspect, the described invention provides a method for treating a non-small cell lung cancer solid tumor comprising a population of tumor cells, the method comprising:

administering to the subject a pharmaceutical composition comprising a therapeutic amount of a polypeptide of the amino acid sequence YARAAARQARAKALARQLGVAA (SEQ ID NO: 1) or a functional equivalent thereof, and a pharmaceutically acceptable carrier thereof, wherein therapeutic amount is effective to inhibit a kinase activity of the population of tumor cells, to reduce proliferation of the population of tumor cells, to reduce tumor size, to reduce tumor burden, to induce tumor cell death, or a combination thereof.

According to the some embodiments, the therapeutic amount may be effective to slow progression of the non-small cell lung cancer solid tumor comprising the population of tumor cells.

According to one embodiment, the tumor is a primary tumor. According to another embodiment, the tumor is a secondary tumor. According to another embodiment, the tumor is a recurrent tumor. According to another embodiment, the tumor is a tumor refractory to chemotherapy.

According to some embodiments, the primary tumor is a squamous cell carcinoma, an adenocarcinoma, or a large cell carcinoma.

According to the some embodiments, the secondary tumor or site of metastasis is one or more of lung tissue, adrenal tissue, bone tissue, liver tissue or brain tissue.

According to some embodiments, cancer cell death may include, but is not limited to, apoptosis.

According to one embodiment, the method is effective to inhibit a kinase activity of Mitogen-Activated Protein Kinase-Activated Protein Kinase 2 (MK2 kinase) in the population of tumor cells. According to another embodiment, the method is effective to inhibit at least 50% of the kinase activity of MK2 kinase in the population of tumor cells. According to another embodiment, the method is effective to inhibit at least 65% of the kinase activity of MK2 kinase in the population of tumor cells. According to another embodiment, the method is effective to inhibit at least 75% of the kinase activity of MK2 kinase in the population of tumor cells. According to another embodiment, the method is effective to inhibit at least 80% of the kinase activity of MK2 kinase in the population of tumor cells. According to another embodiment, the method is effective to inhibit at least 85% of the kinase activity of MK2 kinase in the population of tumor cells. According to another embodiment, the method is effective to inhibit at least 90% of the kinase activity of MK2 kinase in the population of tumor cells. According to another embodiment, the method is effective to inhibit at least 95% of the kinase activity of MK2 kinase in the population of tumor cells.

According to another embodiment, the method is effective to inhibit a kinase activity of Mitogen-Activated Protein Kinase-Activated Protein Kinase 3 (MK3 kinase) in the population of tumor cells. According to another embodiment, the method is effective to inhibit at least 50% of the kinase activity of MK3 kinase in the population of tumor cells. According to another embodiment, the method is effective to inhibit at least 65% of the kinase activity of MK3 kinase in the population of tumor cells. According to another embodiment, the method is effective to inhibit at least 70% of the kinase activity of MK3 kinase in the population of tumor cells. According to another embodiment, the method is effective to inhibit at least 75% of the kinase activity of MK3 kinase in the population of tumor cells. According to another embodiment, the method is effective to inhibit at least 80% of the kinase activity of MK3 kinase in the population of tumor cells. According to another embodiment, the method is effective to inhibit at least 85% of the kinase activity of MK3 kinase in the population of tumor cells. According to another embodiment, the method is effective to inhibit at least 90% of the kinase activity of MK3 kinase in the population of tumor cells. According to another embodiment, the method is effective to inhibit at least 95% of the kinase activity of MK3 kinase in the population of tumor cells.

According to another embodiment, the method is effective to inhibit a kinase activity of calcium/calmodulin-dependent protein kinase I (CaMKI). According to another embodiment, the method is effective to inhibit at least 50% of the kinase activity of $Ca^{2+}$/calmodulin-dependent protein kinase I (CaMKI) in the population of tumor cells. According to another embodiment, the method is effective to inhibit at least 65% of the kinase activity of $Ca^{2+}$/calmodulin-dependent protein kinase I (CaMKI) in the population of tumor cells. According to another embodiment, the method is effective to inhibit at least 70% of the kinase activity of $Ca^{2+}$/calmodulin-dependent protein kinase I (CaMKI) in the population of tumor cells. According to another embodiment, the method is effective to inhibit at least 75% of the kinase activity of $Ca^{2+}$/calmodulin-dependent protein kinase I (CaMKI) in the population of tumor cells. According to another embodiment, the method is effective to inhibit at least 80% of the kinase activity of $Ca^{2+}$/calmodulin-dependent protein kinase I (CaMKI) in the population of tumor cells. According to another embodiment, the method is effective to inhibit at least 85% of the kinase activity of $Ca^{2+}$/calmodulin-dependent protein kinase I (CaMKI) in the population of tumor cells. According to another embodiment, the method is effective to inhibit at least 90% of the kinase activity of $Ca^{2+}$/calmodulin-dependent protein kinase I (CaMKI) in the population of tumor cells. According to another embodiment, the method is effective to inhibit at least 95% of the kinase activity of $Ca^{2+}$/calmodulin-dependent protein kinase I (CaMKI) in the population of tumor cells.

According to another embodiment, the method is effective to inhibit a kinase activity of BDNF/NT-3 growth factors receptor (TrkB) in the population of tumor cells.

According to another embodiment, the method is effective to inhibit at least 50% of the kinase activity of BDNF/NT-3 growth factors receptor (TrkB) in the population of tumor cells. According to another embodiment, the method is effective to inhibit at least 65% of the kinase activity of BDNF/NT-3 growth factors receptor (TrkB) in the population of tumor cells. According to another embodiment, the method is effective to inhibit at least 70% of the kinase activity of BDNF/NT-3 growth factors receptor (TrkB) in the population of tumor cells. According to another embodiment, the method is effective to inhibit at least 75% of the kinase activity of BDNF/NT-3 growth factors receptor (TrkB) in the population of tumor cells.

According to another embodiment, the method is effective to inhibit a kinase activity of Mitogen-Activated Protein Kinase-Activated Protein Kinase 2 (MK2) and a kinase activity of Mitogen-Activated Protein Kinase-Activated Protein Kinase 3 (MK3) in the population of tumor cells.

According to another embodiment, the method is effective to inhibit a kinase activity of Mitogen-Activated Protein Kinase-Activated Protein Kinase 2 (MK2) and a kinase activity of calcium/calmodulin-dependent protein kinase I (CaMKI) in the population of tumor cells.

According to another embodiment, the method is effective to inhibit a kinase activity of Mitogen-Activated Protein Kinase-Activated Protein Kinase 2 (MK2) and a kinase activity of BDNF/NT-3 growth factors receptor (TrkB) in the population of tumor cells.

According to another embodiment, the method is effective to inhibit a kinase activity of Mitogen-Activated Protein Kinase-Activated Protein Kinase 2 (MK2), a kinase activity of Mitogen-Activated Protein Kinase-Activated Protein Kinase 3 (MK3), a kinase activity of calcium/calmodulin-dependent protein kinase I (CaMKI), and a kinase activity of BDNF/NT-3 growth factors receptor (TrkB) in the population of tumor cells.

According to another embodiment, the method is effective to inhibit a kinase activity of Mitogen-Activated Protein Kinase-Activated Protein Kinase 2 (MK2), a kinase activity of calcium/calmodulin-dependent protein kinase I (CaMKI), and a kinase activity of BDNF/NT-3 growth factors receptor (TrkB) in the population of tumor cells.

According to another embodiment, the method is effective to inhibit at least 65% of the kinase activity of Mitogen-Activated Protein Kinase-Activated Protein Kinase 2 (MK2) in the population of tumor cells.

According to another embodiment, the method is effective to inhibit at least 65% of the kinase activity of Mitogen-Activated Protein Kinase-Activated Protein Kinase 3 (MK3) in the population of tumor cells.

According to another embodiment, the method is effective to inhibit at least 65% of the kinase activity of calcium/calmodulin-dependent protein kinase I (CaMKI) in the population of tumor cells.

According to another embodiment, the method is effective to inhibit at least 65% of the kinase activity of BDNF/NT-3 growth factors receptor (TrkB) in the population of tumor cells.

According to another embodiment, the method is effective to inhibit at least 65% of the kinase activity of Mitogen-Activated Protein Kinase-Activated Protein Kinase 2 (MK2) and at least 65% of the kinase activity of Mitogen-Activated Protein Kinase-Activated Protein Kinase 3 (MK3) in the population of tumor cells.

According to another embodiment, the method is effective to inhibit s at least 65% of the kinase activity of Mitogen-Activated Protein Kinase-Activated Protein Kinase 2 (MK2) and at least 65% of the kinase activity of calcium/calmodulin-dependent protein kinase I (CaMKI) in the population of tumor cells.

According to another embodiment, the method is effective to inhibit at least 65% of the kinase activity of Mitogen-Activated Protein Kinase-Activated Protein Kinase 2 (MK2) and at least 65% of the kinase activity of BDNF/NT-3 growth factors receptor (TrkB) in the population of tumor cells.

According to another embodiment, the method is effective to inhibit at least 65% of the kinase activity of Mitogen-Activated Protein Kinase-Activated Protein Kinase 2 (MK2), at least 65% of the kinase activity of Mitogen-Activated Protein Kinase-Activated Protein Kinase 3 (MK3), at least 65% of the kinase activity of calcium/calmodulin-dependent protein kinase I (CaMKI), and at least 65% of the kinase activity of BDNF/NT-3 growth factors receptor (TrkB) in the population of tumor cells.

According to another embodiment, the method is effective to inhibit the kinase activity of at least one kinase selected from the group of MK2, MK3, CaMKI, TrkB in the population of tumor cells, without substantially inhibiting the activity of one or more other selected kinases from the remaining group listed in Table 1 herein in the population of tumor cells.

According to another embodiment, the method is effective to inhibit a kinase activity of a kinase selected from the group listed in Table 1 herein in the population of tumor cells.

According to another embodiment, this inhibition may, for example, be effective to reduce proliferation of the population of tumor cells, to reduce tumor size, to reduce tumor burden, to induce tumor cell death, or a combination thereof.

According to another embodiment, the method may be effective to slow progression of the non-small cell lung cancer solid tumor comprising the population of tumor cells.

According to another embodiment, tumor cell death may include, but is not limited to, apoptosis.

According to some embodiments, inhibitory profiles of MMI inhibitors in vivo depend on dosages, routes of administration, and cell types responding to the inhibitors.

According to such embodiments, the method is effective to inhibit less than 50% of the kinase activity of the other selected kinase(s). According to such embodiments, the method is effective to inhibit less than 65% of the kinase activity of the other selected kinase(s) in the population of tumor cells. According to another embodiment, the method is effective to inhibit less than 50% of the kinase activity of the other selected kinase(s) in the population of tumor cells. According to another embodiment, the method is effective to inhibit less than 40% of the kinase activity of the other selected kinase(s) in the population of tumor cells. According to another embodiment, the method is effective to inhibit less than 20% of the kinase activity of the other selected kinase(s) in the population of tumor cells. According to another embodiment, the method is effective to inhibit less than 15% of the kinase activity of the other selected kinase (s) in the population of tumor cells. According to another embodiment, the method is effective to inhibit less than 10% of the kinase activity of the other selected kinase(s) in the population of tumor cells. According to another embodiment, the method is effective to inhibit less than 5% of the kinase activity of the other selected kinase(s) in the population of tumor cells. According to another embodiment, the method is effective to increase the kinase activity of one or more of the other selected kinases in the population of tumor cells. According to the embodiments of the immediately preceding paragraph, the one or more of the other selected kinases not substantially inhibited is selected from the group of $Ca^{2+}$/calmodulin-dependent protein kinase II (CaMKII, including its subunit CaMKIIδ), Proto-oncogene serine/threonine-protein kinase (PIM-1), cellular-Sarcoma (c-SRC), Spleen Tyrosine Kinase (SYK), C-src Tyrosine Kinase (CSK), and Insulin-like Growth Factor 1 Receptor (IGF-1R).

According to some embodiments, the pharmaceutical composition further comprises at least one additional therapeutic agent.

According to some such embodiments, the additional therapeutic agent is a chemotherapeutic agent. Examples of chemotherapeutic agents include, but are not limited to, Abitrexate (Methotrexate), Abraxane (Paclitaxel Albumin-stabilized Nanoparticle Formulation), Afatinib Dimaleate, Alimta (Pemetrexed Disodium), Avastin (Bevacizumab), Bvacizumab, Carboplatin, Ceritinib, Cisplatin, Crizotinib, Cyramza (Ramucirumab), Docetaxel, Erlotinib Hydrochloride, Folex PFS (Methotrexate), Gefitinib, Gilotrif (Afatinib Dmaleate), Gemcitabine Hydrochloride, Gemzar (Gemcitabine Hydrochloride), Iressa (Gefitinib), Mechlorethamine Hydrochloride, Methotrexate, Methotrexate LPF (Methotrexate), Mexate (Methotrexate), Mexate-AQ (Methotrexate), Mustargen (mechlorethamine Hydrochloride), Navelbine (Vinorelbine Tartrate), Paclitaxel, Paclitaxel Albumin-stabilized nanoparticle Formulation, Paraplat (Carboplatin), Paraplatin (Carboplatin), Pemetrexed Disodium, Platinol (Cisplatin), Platinol-AQ (Cisplatin), Ramucirumab, Tarceva (Erlotinib Hydrochloride), Taxol (Paclitaxel), Taxotere (Docetaxel), Vinorelbine Tartrate, Xalkori (Crizotinib), Zykadia (Ceritinib), Carboplatin-Taxol, and Gemcitabine-Cisplatin.

According to another embodiment, the additional therapeutic agent is an analgesic agent. According to some embodiments, the analgesic agent relieves pain by elevating the pain threshold without disturbing consciousness or altering other sensory modalities. According to some such embodiments, the analgesic agent is a non-opioid analgesic.

"Non-opioid analgesics" are natural or synthetic substances that reduce pain but are not opioid analgesics. Examples of non-opioid analgesics include, but are not limited to, etodolac, indomethacin, sulindac, tolmetin, nabumetone, piroxicam, acetaminophen, fenoprofen, flurbiprofen, ibuprofen, ketoprofen, naproxen, naproxen sodium, oxaprozin, aspirin, choline magnesium trisalicylate, diflunisal, meclofenamic acid, mefenamic acid, and phenylbutazone. According to some other embodiments, the analgesic is an opioid analgesic. "Opioid analgesics", "opioid", or "narcotic analgesics" are natural or synthetic substances that bind to opioid receptors in the central nervous system, producing an agonist action. Examples of opioid analgesics include, but are not limited to, codeine, fentanyl, hydromorphone, levorphanol, meperidine, methadone, morphine, oxycodone, oxymorphone, propoxyphene, buprenorphine, butorphanol, dezocine, nalbuphine, and pentazocine.

According to another embodiment, the additional therapeutic agent is an anti-infective agent. According to another embodiment, the anti-infective agent is an antibiotic agent. The term "antibiotic agent" as used herein means any of a group of chemical substances having the capacity to inhibit the growth of, or to destroy bacteria and other microorganisms, used chiefly in the treatment of infectious diseases. Examples of antibiotic agents include, but are not limited to, Penicillin G; Methicillin; Nafcillin; Oxacillin; Cloxacillin; Dicloxacillin; Ampicillin; Amoxicillin; Ticarcillin; Carbenicillin; Mezlocillin; Azlocillin; Piperacillin; Imipenem; Aztreonam; Cephalothin; Cefaclor; Cefoxitin; Cefuroxime; Cefonicid; Cefmetazole; Cefotetan; Cefprozil; Loracarbef; Cefetamet; Cefoperazone; Cefotaxime; Ceftizoxime; Ceftriaxone; Ceftazidime; Cefepime; Cefixime; Cefpodoxime; Cefsulodin; Fleroxacin; Nalidixic acid; Norfloxacin; Ciprofloxacin; Ofloxacin; Enoxacin; Lomefloxacin; Cinoxacin; Doxycycline; Minocycline; Tetracycline; Amikacin; Gentamicin; Kanamycin; Netilmicin; Tobramycin; Streptomycin; Azithromycin; Clarithromycin; Erythromycin; Erythromycin estolate; Erythromycin ethyl succinate; Erythromycin glucoheptonate; Erythromycin lactobionate; Erythromycin stearate; Vancomycin; Teicoplanin; Chloramphenicol; Clindamycin; Trimethoprim; Sulfamethoxazole; Nitrofurantoin; Rifampin; Mupirocin; Metronidazole; Cephalexin; Roxithromycin; Co-amoxiclavuanate; combinations of Piperacillin and Tazobactam; and their various salts, acids, bases, and other derivatives. Anti-bacterial antibiotic agents include, but are not limited to, penicillins, cephalosporins, carbacephems, cephamycins, carbapenems, monobactams, aminoglycosides, glycopeptides, quinolones, tetracyclines, macrolides, and fluoroquinolones.

According to some other embodiments, the additional therapeutic agent comprises a bronchodilator including, but not limited to, a leukotriene modifier, an anticholinergic bronchodilator, a β2-agonist, or a combination thereof.

According to another embodiment, the additional therapeutic agent comprises a corticosteroid including, but not limited to, prednisone, budesonide, mometasone, beclemethasone, or a combination thereof.

According to some other embodiments, the additional therapeutic agent comprises a bronchodilator including, but not limited to, a leukotriene modifier, an anticholinergic bronchodilator, a β2-agonist, or a combination thereof.

According to another embodiment, the additional therapeutic agent comprises a corticosteroid including, but not limited to, prednisone, budesonide, mometasone, beclemethasone, or a combination thereof.

According to another embodiment, the additional therapeutic agent is an anti-inflammatory agent.

According to another embodiment, the anti-inflammatory agent is a nonsteroidal anti-inflammatory agent. Mixtures of non-steroidal anti-inflammatory agents also may be employed, as well as the dermatologically acceptable salts and esters of these agents. For example, etofenamate, a flufenamic acid derivative, is particularly useful for topical application.

According to another embodiment, wherein the nonsteroidal anti-inflammatory agent comprises Transforming Growth Factor-β3 (TGF-β3), an anti-Tumor Necrosis Factor-alpha (TNF-α) agent, or a combination thereof.

According to another embodiment, the anti-inflammatory agent is a steroidal anti-inflammatory agent. According to another embodiment, the steroidal anti-inflammatory agent comprises at least one corticosteroid selected from the group consisting of prednisone, budesonide, mometasone, beclemethasone, and a combination thereof.

According to another embodiment, the additional therapeutic agent comprises a methylxanthine.

According to another embodiment, the additional therapeutic agent comprises a neutrophil elastase inhibitor.

According to another embodiment, the additional therapeutic agent is at least one neutrophil elastase inhibitor, including, but not limited to, ICI 200355, ONO-5046, MR-889, L-694,458, CE-1037, GW-311616, TEI-8362, ONO-6818, AE-3763, FK-706, ICI-200,880, ZD-0892, ZD-8321, and a combination thereof.

According to another embodiment, the additional therapeutic agent comprises at least one phosphodiesterase inhibitor, including, but not limited to, phosphodiesterase 4 inhibitor. Examples of phosphodiesterase 4 inhibitors include, but are not limited to, roflumilast, cilomilast or a combination thereof.

According to some embodiments, the functional equivalent of the polypeptide YARAAARQARAKALARQLGVAA (SEQ ID NO: 1) has a substantial sequence identity to amino acid sequence YARAAARQARAKALARQLGVAA (SEQ ID NO: 1).

According to some such embodiments, the functional equivalent of the polypeptide YARAAARQARAKALARQLGVAA (SEQ ID NO: 1) has at least 70 percent sequence identity to amino acid sequence YARAAARQARAKALARQLGVAA (SEQ ID NO: 1). According to another embodiment, the functional equivalent of the polypeptide YARAAARQARAKALARQLGVAA (SEQ ID NO: 1) has at least 80 percent sequence identity to amino acid sequence YARAAARQARAKALARQLGVAA (SEQ ID NO: 1). According to another embodiment, the functional equivalent of the polypeptide YARAAARQARAKALARQLGVAA (SEQ ID NO: 1) has at least 90 percent sequence identity to amino acid sequence YARAAARQARAKALARQLGVAA (SEQ ID NO: 1). According to another embodiment, the functional equivalent of the polypeptide YARAAARQARAKALARQLGVAA (SEQ ID NO: 1) has at least 95 percent sequence identity to amino acid sequence YARAAARQARAKALARQLGVAA (SEQ ID NO: 1).

According to another embodiment, the functional equivalent of the polypeptide YARAAARQARAKALARQLGVAA (SEQ ID NO: 1) is of amino acid sequence FAKLAARLYRKALARQLGVAA (SEQ ID NO: 3).

According to another embodiment, the functional equivalent of the polypeptide YARAAARQARAKALARQLGVAA (SEQ ID NO: 1) is of amino acid sequence KAFAKLAARLYRKALARQLGVAA (SEQ ID NO: 4).

According to another embodiment, the functional equivalent of the polypeptide YARAAARQARAKALARQL- GVAA (SEQ ID NO: 1) is of amino acid sequence YARAAARQARAKALARQLAVA (SEQ ID NO: 5).

According to another embodiment, the functional equivalent of the polypeptide YARAAARQARAKALARQLGVAA (SEQ ID NO: 1) is of amino acid sequence YARAAARQARAKALARQLGVA (SEQ ID NO: 6).

According to another embodiment, the functional equivalent of the polypeptide YARAAARQARAKALARQLGVAA (SEQ ID NO: 1) is of amino acid sequence HRRIKAWLKKIKALARQLGVAA (SEQ ID NO: 7).

According to some other embodiments, the functional equivalent of the polypeptide YARAAARQARAKALARQLGVAA (SEQ ID NO: 1) is a fusion protein comprising a first polypeptide operatively linked to a second polypeptide, wherein the first polypeptide is of amino acid sequence YARAAARQARA (SEQ ID NO: 11), and the second polypeptide comprises a therapeutic domain whose sequence has a substantial identity to amino acid sequence KALARQLGVAA (SEQ ID NO: 2).

According to another embodiment, the second polypeptide has at least 70 percent sequence identity to amino acid sequence KALARQLGVAA (SEQ ID NO: 2). According to some other embodiments, the second polypeptide has at least 80 percent sequence identity to amino acid sequence KALARQLGVAA (SEQ ID NO: 2). According to some other embodiments, the second polypeptide has at least 90 percent sequence identity to amino acid sequence KALARQLGVAA (SEQ ID NO: 2). According to some other embodiments, the second polypeptide has at least 95 percent sequence identity to amino acid sequence KALARQLGVAA (SEQ ID NO: 2).

According to another embodiment, the second polypeptide is a polypeptide of amino acid sequence KALARQLAVA (SEQ ID NO: 8).

According to another embodiment, the second polypeptide is a polypeptide of amino acid sequence KALARQLGVA (SEQ ID NO: 9).

According to another embodiment, the second polypeptide is a polypeptide of amino acid sequence KALARQLGVAA (SEQ ID NO: 10).

According to some embodiments, the functional equivalent of the polypeptide YARAAARQARAKALARQLGVAA (SEQ ID NO: 1) is a fusion protein comprising a first polypeptide operatively linked to a second polypeptide, wherein the first polypeptide comprises a cell penetrating peptide functionally equivalent to YARAAARQARA (SEQ ID NO: 11), and the second polypeptide is of amino acid sequence KALARQLGVAA (SEQ ID NO: 2), and the pharmaceutical composition inhibits both the kinase activity of Mitogen-Activated Protein Kinase-Activated Protein Kinase 2 (MK2).

According to another embodiment, the first polypeptide is a polypeptide of amino acid sequence WLRRIKAWLRRIKA (SEQ ID NO: 12).

According to another embodiment, the first polypeptide is a polypeptide of amino acid sequence WLRRIKA (SEQ ID NO: 13).

According to another embodiment, the first polypeptide is a polypeptide of amino acid sequence YGRKKRRQRRR (SEQ ID NO: 14).

According to another embodiment, the first polypeptide is a polypeptide of amino acid sequence WLRRIKAWLRRI (SEQ ID NO: 15).

According to another embodiment, the first polypeptide is a polypeptide of amino acid sequence FAKLAARLYR (SEQ ID NO: 16). According to some such embodiments, the first polypeptide is a polypeptide of amino acid sequence KAFAKLAARLYR (SEQ ID NO: 17). According to some such embodiments, the first polypeptide is a polypeptide of amino acid sequence HRRIKAWLKKI (SEQ ID NO: 18).

According to another aspect, the described invention also provides an isolated nucleic acid that encodes a protein sequence with at least 70% amino acid sequence identity to amino acid sequence YARAAARQARAKALARQLGVAA (SEQ ID NO: 1).

According to some such embodiments, the isolated nucleic acid encodes a protein sequence with at least 80% amino acid sequence identity to amino acid sequence YARAAARQARAKALARQLGVAA (SEQ ID NO: 1). According to some other embodiments, the isolated nucleic acid encodes a protein sequence with at least 90% amino acid sequence identity to amino acid sequence YARAAARQARAKALARQLGVAA (SEQ ID NO: 1). According to some other embodiments, the isolated nucleic acid encodes a protein sequence with at least 95% amino acid sequence identity to amino acid sequence YARAAARQARAKALARQLGVAA (SEQ ID NO: 1).

According to another embodiment, the step of administering occurs by pulmonary delivery. According to some embodiments, the step of administering may occur systemically either orally, buccally, parenterally, topically, by inhalation, by insufflation, or rectally, or may occur locally by means such as, but not limited to, injection, implantation, grafting, topical application, or parenterally. Additional administration may be performed, for example, intravenously, transmucosally, transdermally, intramuscularly, subcutaneously, intratracheally (including by pulmonary inhalation), intraperitoneally, intrathecally, intralymphatically, intralesionally, or epidurally. Administering can be performed, for example, once, a plurality of times, and/or over one or more extended periods either as individual unit doses or in the form of a treatment regimen comprising multiple unit doses of multiple drugs and/or substances.

According to some other embodiments, the step of administering occurs at one time as a single dose. According to some other embodiments, the step of administering is performed as a plurality of doses over a period of time. According to some such embodiments, the period of time is a day, a week, a month, a month, a year, or multiples thereof. According to some embodiments, the step of administering is performed daily for a period of at least one week. According to some embodiments, the step of administering is performed weekly for a period of at least one month. According to some embodiments, the step of administering is performed monthly for a period of at least two months. According to another embodiment, the step of administering is performed repeatedly over a period of at least one year. According to another embodiment, the step of administering is performed at least once monthly. According to another embodiment, the step of administering is performed at least once weekly. According to another embodiment, the step of administering is performed at least once daily.

According to some other embodiments, the therapeutic amount of the pharmaceutical composition is administered via an inhalation device. Examples of the inhalation device that can be used for administering the pharmaceutical composition include, but are not limited to, a nebulizer, a metered-dose inhaler (MDI), a dry powder inhaler (DPI), and a dry powder nebulizer.

According to another embodiment, the dry powder comprises microparticles with Mass Median Aerodynamic Diameter (MMAD) of 1 to 5 microns. According to another embodiment, the dry powder comprises microparticles with Mass Median Aerodynamic Diameter (MMAD) of about 2 micron.

According to some other embodiments, the therapeutic amount of therapeutic inhibitor peptide of the pharmaceutical composition is of an amount from about 0.000001 mg/kg body weight to about 100 mg/kg body weight. According to another embodiment, the therapeutic amount of therapeutic inhibitory peptide of the pharmaceutical composition is of an amount from about 0.00001 mg/kg body weight to about 100 mg/kg body weight. According to another embodiment, the therapeutic amount of therapeutic inhibitory peptide of the pharmaceutical composition is of an amount from about 0.0001 mg/kg body weight to about 100 mg/kg body weight. According to another embodiment, the therapeutic amount of therapeutic inhibitory peptide of the pharmaceutical composition is of an amount from about 0.001 mg/kg body weight to about 10 mg/kg body weight. According to another embodiment, the therapeutic amount of therapeutic inhibitory peptide of the pharmaceutical composition is of an amount from about 0.01 mg/kg body weight to about 10 mg/kg body weight. According to another embodiment, the therapeutic amount of therapeutic inhibitory peptide of the pharmaceutical composition is of an amount from about 0.1 mg/kg (or 100 µg/kg) body weight to about 10 mg/kg body weight. According to another embodiment, the therapeutic amount of therapeutic inhibitory peptide of the pharmaceutical composition is of an amount from about 1 mg/kg body weight to about 10 mg/kg body weight. According to another embodiment, the therapeutic amount of therapeutic inhibitory peptide of the pharmaceutical composition is of an amount from about 10 mg/kg body weight to about 100 mg/kg body weight. According to another embodiment, the therapeutic amount of therapeutic inhibitory peptide of the pharmaceutical composition is of an amount from about 2 mg/kg body weight to about 10 mg/kg body weight. According to another embodiment, the therapeutic amount of therapeutic inhibitory peptide of the pharmaceutical composition is of an amount from about 3 mg/kg body weight to about 10 mg/kg body weight. According to another embodiment, the therapeutic amount of therapeutic inhibitory peptide of the pharmaceutical composition is of an amount from about 4 mg/kg body weight to about 10 mg/kg body weight. According to another embodiment, the therapeutic amount of therapeutic inhibitory peptide of the pharmaceutical composition is of an amount from about 5 mg/kg body weight to about 10 mg/kg body weight. According to another embodiment, the therapeutic amount of therapeutic inhibitory peptide of the pharmaceutical composition is of an amount from about 60 mg/kg body weight to about 100 mg/kg body weight. According to another embodiment, the therapeutic amount of therapeutic inhibitory peptide of the pharmaceutical composition is of an amount from about 70 mg/kg body weight to about 100 mg/kg body weight. According to another embodiment, the therapeutic amount of therapeutic inhibitory peptide of the pharmaceutical composition is of an amount from about 80 mg/kg body weight to about 100 mg/kg body weight. According to another embodiment, the therapeutic amount of therapeutic inhibitory peptide of the pharmaceutical composition is of an amount from about 90 mg/kg body weight to about 100 mg/kg body weight. According to another embodiment, the therapeutic amount of therapeutic inhibitor peptide of the pharmaceutical composition is of an amount from about 0.000001 mg/kg body weight to about 90 mg/kg body weight. According to another embodiment, the therapeutic amount of therapeutic inhibitor peptide of the pharmaceutical composition is of an amount from about 0.000001 mg/kg body weight to about 80 mg/kg body weight. According to another embodiment, the therapeutic amount of therapeutic inhibitor peptide of the pharmaceutical composition is of an amount from about 0.000001 mg/kg body weight to about 70 mg/kg body weight. According to another embodiment, the therapeutic amount of therapeutic inhibitor peptide of the pharmaceutical composition is of an amount from about 0.000001 mg/kg body weight to about 60 mg/kg body weight. According to another embodiment, the therapeutic amount of therapeutic inhibitor peptide of the pharmaceutical composition is of an amount from about 0.000001 mg/kg body weight to about 50 mg/kg body weight. According to another embodiment, the therapeutic amount of therapeutic inhibitor peptide of the pharmaceutical composition is of an amount from about 0.000001 mg/kg body weight to about 40 mg/kg body weight. According to another embodiment, the therapeutic amount of therapeutic inhibitor peptide is of an amount from about 0.000001 mg/kg body weight to about 30 mg/kg body weight. According to another embodiment, the therapeutic amount of therapeutic inhibitor peptide of the pharmaceutical composition is of an amount from about 0.000001 mg/kg body weight to about 20 mg/kg body weight. According to another embodiment, the therapeutic amount of therapeutic inhibitor peptide of the pharmaceutical composition is of an amount from about 0.000001 mg/kg body weight to about 10 mg/kg body weight. According to another embodiment, the therapeutic amount of therapeutic inhibitor peptide of the pharmaceutical composition is of an amount from about 0.000001 mg/kg body weight to about 1 mg/kg body weight. According to another embodiment, the therapeutic amount of therapeutic inhibitor peptide of the pharmaceutical composition is of an amount from about 0.000001 mg/kg body weight to about 0.1 mg/kg body weight. According to another embodiment, the therapeutic amount of therapeutic inhibitor peptide of the pharmaceutical composition is of an amount from about 0.000001 mg/kg body weight to about 0.1 mg/kg body weight. According to another embodiment, the therapeutic amount of therapeutic inhibitor peptide of the pharmaceutical composition is of an amount from about 0.000001 mg/kg body weight to about 0.01 mg/kg body weight. According to another embodiment, the therapeutic amount of therapeutic inhibitor peptide of the pharmaceutical composition is of an amount from about 0.000001 mg/kg body weight to about 0.001 mg/kg body weight. According to another embodiment, the therapeutic amount of therapeutic inhibitor peptide of the pharmaceutical composition is of an amount from about 0.000001 mg/kg body weight to about 0.0001 mg/kg body weight. According to another embodiment, the therapeutic amount of therapeutic inhibitor peptide of the pharmaceutical composition is of an amount from about 0.000001 mg/kg body weight to about 0.00001 mg/kg body weight.

According to some other embodiments, the therapeutic dose of therapeutic inhibitor peptide of the pharmaceutical composition ranges from 1 µg/kg/day to 25 µg/kg/day. According to some other embodiments, the therapeutic dose of therapeutic inhibitor peptide of the pharmaceutical composition ranges from 1 µg/kg/day to 2 µg/kg/day. According to some other embodiments, the therapeutic dose of therapeutic inhibitor peptide of the pharmaceutical composition ranges from 2 µg/kg/day to 3 µg/kg/day. According to some other embodiments, the therapeutic dose of therapeutic inhibitor peptide of the pharmaceutical composition ranges from 3 µg/kg/day to 4 µg/kg/day. According to some other embodiments, the therapeutic dose of therapeutic inhibitor peptide of the pharmaceutical ranges from 4 µg/kg/day to 5 µg/kg/day. According to some other embodiments, the therapeutic dose of therapeutic inhibitor peptide of the pharmaceutical composition ranges from 5 µg/kg/day to 6 µg/kg/day. According to some other embodiments, the therapeutic dose of therapeutic inhibitor peptide of the pharmaceutical composition ranges from 6 µg/kg/day to 7 µg/kg/day. According to some other embodiments, the therapeutic dose of therapeutic inhibitor peptide of the pharmaceutical composition ranges from 7 µg/kg/day to 8 µg/kg/day. According to some other embodiments, the therapeutic dose of therapeutic inhibitor peptide of the pharmaceutical composition ranges from 8 µg/kg/day to 9 µg/kg/day. According to some other embodiments, the therapeutic dose of therapeutic inhibitor peptide of the pharmaceutical composition ranges from 9 µg/kg/day to 10 µg/kg/day. According to some other embodiments, the therapeutic dose of therapeutic inhibitor peptide of the pharmaceutical composition ranges from 1 µg/kg/day to 5 µg/kg/day. According to some other embodiments, the therapeutic dose of therapeutic inhibitor peptide of the pharmaceutical composition ranges from 5 µg/kg/day to 10 µg/kg/day. According to some other embodiments, the therapeutic dose of therapeutic inhibitor peptide of the pharmaceutical composition ranges from 10 µg/kg/day to 15 µg/kg/day. According to some other embodiments, the therapeutic dose of therapeutic inhibitor peptide of the pharmaceutical composition ranges from 15 µg/kg/day to 20 µg/kg/day. According to some other embodiments, the therapeutic dose of therapeutic inhibitor peptide of the pharmaceutical composition ranges from 25 µg/kg/day to 30 µg/kg/day. According to some other embodiments, the therapeutic dose of therapeutic inhibitor peptide of the pharmaceutical composition ranges from 30 µg/kg/day to 35 µg/kg/day. According to some other embodiments, the therapeutic dose of therapeutic inhibitor peptide of the pharmaceutical composition ranges from 35 µg/kg/day to 40 µg/kg/day. According to some other embodiments, the therapeutic dose of therapeutic inhibitor peptide of the pharmaceutical composition ranges from 40 µg/kg/day to 45 µg/kg/day. According to some other embodiments, the therapeutic dose of therapeutic inhibitor peptide of the pharmaceutical composition ranges from 45 µg/kg/day to 50 µg/kg/day. According to some other embodiments, the therapeutic dose of therapeutic inhibitor peptide of the pharmaceutical composition ranges from 50 µg/kg/day to 55 µg/kg/day. According to some other embodiments, the therapeutic dose of therapeutic inhibitor peptide of the pharmaceutical composition ranges from 55 µg/kg/day to 60 µg/kg/day. According to some other embodiments, the therapeutic dose of therapeutic inhibitor peptide of the pharmaceutical composition ranges from 60 µg/kg/day to 65 µg/kg/day. According to some other embodiments, the therapeutic dose of therapeutic inhibitor peptide of the pharmaceutical composition ranges from 65 µg/kg/day to 70 µg/kg/day. According to some other embodiments, the therapeutic dose of therapeutic inhibitor peptide of the pharmaceutical composition ranges from 70 µg/kg/day to 75 µg/kg/day. According to some other embodiments, the therapeutic dose of therapeutic inhibitor peptide of the pharmaceutical composition ranges from 80 µg/kg/day to 85 µg/kg/day. According to some other embodiments, the therapeutic dose of therapeutic inhibitor peptide of the pharmaceutical composition ranges from 85 µg/kg/day to 90 µg/kg/day. According to some other embodiments, the therapeutic dose of therapeutic inhibitor peptide of the pharmaceutical composition ranges from 90 µg/kg/day to 95 µg/kg/day. According to some other embodiments, the therapeutic dose of therapeutic inhibitor peptide of the pharmaceutical composition ranges from 95 µg/kg/day to 100 µg/kg/day.

According to another embodiment, the therapeutic dose of therapeutic inhibitor peptide of the pharmaceutical composition is 1 µg/kg/day.

According to another embodiment, the therapeutic dose of therapeutic inhibitor peptide of the pharmaceutical composition is 2 µg/kg/day.

According to another embodiment, the therapeutic dose of therapeutic inhibitor peptide of the pharmaceutical composition is 5 µg/kg/day.

According to another embodiment, the therapeutic dose of therapeutic inhibitor peptide of the pharmaceutical composition is 10 µg/kg/day.

According to another embodiment the treatment further comprises an adjunct therapy. According to some such embodiments, the adjunct therapy comprises one or more of surgical resection of the tumor, radiotherapy, or insertion of an expandable metal stent.

III. Systems for Treating Signs and Symptoms of Non-Small Cell Lung Cancer (NSCLC)

According to another aspect, the described invention provides a system for the treatment of a non-small cell lung cancer (NSCLC) tumor comprising a population of tumor cells comprising (a) a pharmaceutical composition, wherein the pharmaceutical composition comprises a therapeutic amount of a polypeptide of the amino acid sequence YARAAAR-QARAKALARQLGVAA (SEQ ID NO: 1) or a functional equivalent thereof, and a pharmaceutically acceptable carrier thereof, and wherein therapeutic amount may be effective to inhibit a kinase activity of a kinase selected from the group listed in Table 1 in the population of tumor cells and to reduce proliferation of the population of tumor cells, to reduce tumor size, to reduce tumor burden, to induce tumor cell death, to overcome tumor chemoresistance, to enhance tumor chemosensitivity, or a combination thereof;

and (b) an inhalation device for pulmonary delivery.

According to one embodiment, the tumor is a primary tumor. According to another embodiment, the tumor is a secondary tumor. According to another embodiment, the tumor is a recurrent tumor. According to another embodiment, the tumor is a tumor refractory to chemotherapy.

According to some embodiments, the primary tumor is a squamous cell carcinoma, an adenocarcinoma, or a large cell carcinoma.

According to the some embodiments, the secondary tumor or site of metastasis is one or more of lung tissue, adrenal tissue, bone tissue, liver tissue or brain tissue.

According to another embodiment, the tumor cell death may include, but is not limited to, apoptosis.

According to another embodiment, the pharmaceutically acceptable carrier includes, but is not limited to, a controlled release carrier, a delayed release carrier, a sustained release carrier, and a long-term release carrier.

According to another embodiment, the inhalation device is a nebulizer.

According to another embodiment, the inhalation device is a metered-dose inhaler (MDI).

According to another embodiment, the inhalation device is a dry powder inhaler (DPI).

According to another embodiment, the inhalation device is a dry powder nebulizer.

According to another embodiment, the pharmaceutical composition is in a form of a dry powder.

According to another embodiment, the dry powder comprises microparticles with Mass Median Aerodynamic Diameter (MMAD) of 1 to 5 microns.

According to another embodiment, the dry powder comprises microparticles with Mass Median Aerodynamic Diameter (MMAD) of about 2 micron.

According to some embodiments, the pharmaceutical composition further comprises at least one additional therapeutic agent.

According to some such embodiments, the additional therapeutic agent is a chemotherapeutic agent. Examples of chemotherapeutic agents include, but are not limited to, Abitrexate (Methotrexate), Abraxane (Paclitaxel Albumin-stabilized Nanoparticle Formulation), Afatinib Dimaleate, Alimta (Pemetrexed Disodium), Avastin (Bevacizumab), Bvacizumab, Carboplatin, Ceritinib, Cisplatin, Crizotinib, Cyramza (Ramucirumab), Docetaxel, Erlotinib Hydrochloride, Folex PFS (Methotrexate), Gefitinib, Gilotrif (Afatinib Dmaleate), Gemcitabine Hydrochloride, Gemzar (Gemcitabine Hydrochloride), Iressa (Gefitinib), Mechlorethamine Hydrochloride, Methotrexate, Methotrexate LPF (Methotrexate), Mexate (Methotrexate), Mexate-AQ (Methotrexate), Mustargen (mechlorethamine Hydrochloride), Navelbine (Vinorelbine Tartrate), Paclitaxel, Paclitaxel Albumin-stabilized nanoparticle Formulation, Paraplat (Carboplatin), Paraplatin (Carboplatin), Pemetrexed Disodium, Platinol (Cisplatin), Platinol-AQ (Cisplatin), Ramucirumab, Tarceva (Erlotinib Hydrochloride), Taxol (Paclitaxel), Taxotere (Docetaxel), Vinorelbine Tartrate, Xalkori (Crizotinib), Zykadia (Ceritinib), Carboplatin-Taxol, and Gemcitabine-Cisplatin.

According to another embodiment, the additional therapeutic agent is an analgesic agent. According to some embodiments, the analgesic agent relieves pain by elevating the pain threshold without disturbing consciousness or altering other sensory modalities. According to some such embodiments, the analgesic agent is a non-opioid analgesic. "Non-opioid analgesics" are natural or synthetic substances that reduce pain but are not opioid analgesics. Examples of non-opioid analgesics include, but are not limited to, etodolac, indomethacin, sulindac, tolmetin, nabumetone, piroxicam, acetaminophen, fenoprofen, flurbiprofen, ibuprofen, ketoprofen, naproxen, naproxen sodium, oxaprozin, aspirin, choline magnesium trisalicylate, diflunisal, meclofenamic acid, mefenamic acid, and phenylbutazone. According to some other embodiments, the analgesic is an opioid analgesic. "Opioid analgesics", "opioid", or "narcotic analgesics" are natural or synthetic substances that bind to opioid receptors in the central nervous system, producing an agonist action. Examples of opioid analgesics include, but are not limited to, codeine, fentanyl, hydromorphone, levorphanol, meperidine, methadone, morphine, oxycodone, oxymorphone, propoxyphene, buprenorphine, butorphanol, dezocine, nalbuphine, and pentazocine.

According to another embodiment, the additional therapeutic agent is an anti-infective agent. According to another embodiment, the anti-infective agent is an antibiotic agent. The term "antibiotic agent" as used herein means any of a group of chemical substances having the capacity to inhibit the growth of, or to destroy bacteria and other microorganisms, used chiefly in the treatment of infectious diseases. Examples of antibiotic agents include, but are not limited to, Penicillin G; Methicillin; Nafcillin; Oxacillin; Cloxacillin; Dicloxacillin; Ampicillin; Amoxicillin; Ticarcillin; Carbenicillin; Mezlocillin; Azlocillin; Piperacillin; Imipenem; Aztreonam; Cephalothin; Cefaclor; Cefoxitin; Cefuroxime; Cefonicid; Cefmetazole; Cefotetan; Cefprozil; Loracarbef; Cefetamet; Cefoperazone; Cefotaxime; Ceftizoxime; Ceftriaxone; Ceftazidime; Cefepime; Cefixime; Cefpodoxime; Cefsulodin; Fleroxacin; Nalidixic acid; Norfloxacin; Ciprofloxacin; Ofloxacin; Enoxacin; Lomefloxacin; Cinoxacin; Doxycycline; Minocycline; Tetracycline; Amikacin; Gentamicin; Kanamycin; Netilmicin; Tobramycin; Streptomycin; Azithromycin; Clarithromycin; Erythromycin; Erythromycin estolate; Erythromycin ethyl succinate; Erythromycin glucoheptonate; Erythromycin lactobionate; Erythromycin stearate; Vancomycin; Teicoplanin; Chloramphenicol; Clindamycin; Trimethoprim; Sulfamethoxazole; Nitrofurantoin; Rifampin; Mupirocin; Metronidazole; Cephalexin; Roxithromycin; Co-amoxiclavuanate; combinations of Piperacillin and Tazobactam; and their various salts, acids, bases, and other derivatives. Anti-bacterial antibiotic agents include, but are not limited to, penicillins, cephalosporins, carbacephems, cephamycins, carbapenems, monobactams, aminoglycosides, glycopeptides, quinolones, tetracyclines, macrolides, and fluoroquinolones.

According to some other embodiments, the additional therapeutic agent comprises a bronchodilator including, but not limited to, a leukotriene modifier, an anticholinergic bronchodilator, a β2-agonist, or a combination thereof.

According to another embodiment, the additional therapeutic agent comprises a corticosteroid including, but not limited to, prednisone, budesonide, mometasone, beclemethasone, or a combination thereof.

According to some other embodiments, the additional therapeutic agent comprises a bronchodilator including, but not limited to, a leukotriene modifier, an anticholinergic bronchodilator, a β2-agonist, or a combination thereof.

According to another embodiment, the additional therapeutic agent comprises a corticosteroid including, but not limited to, prednisone, budesonide, mometasone, beclemethasone, or a combination thereof.

According to another embodiment, the additional therapeutic agent is an anti-inflammatory agent.

According to another embodiment, the anti-inflammatory agent is a nonsteroidal anti-inflammatory agent. Mixtures of non-steroidal anti-inflammatory agents also may be employed, as well as the dermatologically acceptable salts and esters of these agents. For example, etofenamate, a flufenamic acid derivative, is particularly useful for topical application.

According to another embodiment, wherein the nonsteroidal anti-inflammatory agent comprises Transforming Growth Factor-β3 (TGF-β3), an anti-Tumor Necrosis Factor-alpha (TNF-α) agent, or a combination thereof.

According to another embodiment, the anti-inflammatory agent is a steroidal anti-inflammatory agent. According to another embodiment, the steroidal anti-inflammatory agent comprises at least one corticosteroid selected from the group consisting of prednisone, budesonide, mometasone, beclemethasone, and a combination thereof.

According to another embodiment, the additional therapeutic agent comprises a methylxanthine.

According to another embodiment, the additional therapeutic agent comprises a neutrophil elastase inhibitor.

According to another embodiment, the additional therapeutic agent is at least one neutrophil elastase inhibitor, including, but not limited to, ICI 200355, ONO-5046, MR-889, L-694,458, CE-1037, GW-311616, TEI-8362, ONO-6818, AE-3763, FK-706, ICI-200,880, ZD-0892, ZD-8321, and a combination thereof.

According to another embodiment, the additional therapeutic agent comprises at least one phosphodiesterase inhibitor, including, but not limited to, phosphodiesterase 4 inhibitor. Examples of phosphodiesterase 4 inhibitors include, but are not limited to, roflumilast, cilomilast or a combination thereof.

According to another embodiment, the pharmaceutical composition inhibits a kinase activity of a kinase selected from the group listed in Table 1 herein.

According to another embodiment, the inhibition may be effective to slow progression of the non-small cell lung cancer solid tumor comprising the population of tumor cells.

According to another embodiment, the pharmaceutical composition is effective to inhibit at least 50% of the kinase activity of the kinase in the population of tumor cells. According to another embodiment, the pharmaceutical composition is effective to inhibit at least 65% of the kinase activity of the kinase in the population of tumor cells. According to another embodiment, the pharmaceutical composition is effective to inhibit at least 75% of the kinase activity of that kinase in the population of tumor cells. According to another embodiment, the pharmaceutical composition is effective to inhibit at least 80% of the kinase activity of that kinase in the population of tumor cells. According to another embodiment, the pharmaceutical composition is effective to inhibit at least 85% of the kinase activity of that kinase in the population of tumor cells. According to another embodiment, the pharmaceutical composition is effective to inhibit at least 90% of the kinase activity of that kinase in the population of tumor cells. According to another embodiment, the pharmaceutical composition is effective to inhibit s at least 95% of the kinase activity of that kinase in the population of tumor cells.

According to some embodiments, inhibitory profiles of MMI inhibitors in vivo depend on dosages, routes of administration, and cell types responding to the inhibitors.

According to another embodiment, the pharmaceutical composition is effective to inhibit at least 50% of the kinase activity of the kinase in the population of tumor cells. According to another embodiment, the pharmaceutical composition is effective to inhibit at least 65% of the kinase activity of the kinase in the population of tumor cells. According to another embodiment, the pharmaceutical composition is effective to inhibit at least 75% of the kinase activity of that kinase in the population of tumor cells. According to another embodiment, the pharmaceutical composition is effective to inhibit at least 80% of the kinase activity of that kinase in the population of tumor cells. According to another embodiment, the pharmaceutical composition is effective to inhibit at least 85% of the kinase activity of that kinase in the population of tumor cells. According to another embodiment, the pharmaceutical composition is effective to inhibit at least 90% of the kinase activity of that kinase in the population of tumor cells. According to another embodiment, the pharmaceutical composition is effective to inhibit at least 95% of the kinase activity of that kinase in the population of tumor cells.

According to another embodiment, the pharmaceutical composition is effective to inhibit a kinase activity of Mitogen-Activated Protein Kinase-Activated Protein Kinase 2 (MK2 kinase) in the population of tumor cells. According to another embodiment, the pharmaceutical composition is effective to inhibit s at least 50% of the kinase activity of MK2 kinase in the population of tumor cells. According to another embodiment, the pharmaceutical composition is effective to inhibit at least 65% of the kinase activity of MK2 kinase in the population of tumor cells. According to another embodiment, the pharmaceutical composition is effective to inhibit at least 75% of the kinase activity of MK2 kinase in the population of tumor cells. According to another embodiment, the pharmaceutical composition is effective to inhibit at least 80% of the kinase activity of MK2 kinase in the population of tumor cells. According to another embodiment, the pharmaceutical composition is effective to inhibit at least 85% of the kinase activity of MK2 kinase in the population of tumor cells. According to another embodiment, the pharmaceutical composition is effective to inhibit at least 90% of the kinase activity of MK2 kinase in the population of tumor cells. According to another embodiment, the pharmaceutical composition is effective to inhibit at least 95% of the kinase activity of MK2 kinase v.

According to another embodiment, the pharmaceutical composition is effective to inhibit a kinase activity of Mitogen-Activated Protein Kinase-Activated Protein Kinase 3 (MK3 kinase) in the population of tumor cells. According to another embodiment, the pharmaceutical composition is effective to inhibit at least 50% of the kinase activity of MK3 kinase in the population of tumor cells. According to another embodiment, the pharmaceutical composition is effective to inhibit at least 65% of the kinase activity of MK3 kinase in the population of tumor cells. According to another embodiment, the pharmaceutical composition is effective to inhibit at least 70% of the kinase activity of MK3 kinase in the population of tumor cells. According to another embodiment, the pharmaceutical composition is effective to inhibit at least 75% of the kinase activity of MK3 kinase in the population of tumor cells. According to another embodiment, the pharmaceutical composition is effective to inhibit ibits at least 80% of the kinase activity of MK3 kinase in the population of tumor cells. According to another embodiment, the pharmaceutical composition is effective to inhibit at least 85% of the kinase activity of MK3 kinase in the population of tumor cells. According to another embodiment, the pharmaceutical composition is effective to inhibit at least 90% of the kinase activity of MK3 kinase in the population of tumor cells. According to another embodiment, the pharmaceutical composition is effective to inhibit at least 95% of the kinase activity of MK3 kinase in the population of tumor cells.

According to another embodiment, the pharmaceutical composition is effective to inhibit a kinase activity of calcium/calmodulin-dependent protein kinase I (CaMKI) in the population of tumor cells. According to another embodiment, the pharmaceutical composition is effective to inhibit at least 50% of the kinase activity of $Ca^{2+}$/calmodulin-dependent protein kinase I (CaMKI) in the population of tumor cells. According to another embodiment, the pharmaceutical composition is effective to inhibit at least 65% of the kinase activity of $Ca^{2+}$/calmodulin-dependent protein kinase I (CaMKI) in the population of tumor cells. According to another embodiment, the pharmaceutical composition is effective to inhibit at least 70% of the kinase activity of $Ca^{2+}$/calmodulin-dependent protein kinase I (CaMKI) in the population of tumor cells. According to another embodiment, the pharmaceutical composition is effective to inhibit at least 75% of the kinase activity of $Ca^{2+}$/calmodulin-dependent protein kinase I (CaMKI) in the population of tumor cells. According to another embodiment, the pharmaceutical composition is effective to inhibit at least 80% of the kinase activity of $Ca^{2+}$/calmodulin-dependent protein kinase I (CaMKI) in the population of tumor cells. According to another embodiment, the pharmaceutical composition is effective to inhibit at least 85% of the kinase activity of $Ca^{2+}$/calmodulin-dependent protein kinase I (CaMKI) in the population of tumor cells. According to another embodiment, the pharmaceutical composition is effective to inhibit at least 90% of the kinase activity of $Ca^{2+}$/calmodulin-dependent protein kinase I (CaMKI) in the population of tumor cells. According to another embodiment, the pharmaceutical composition is effective to inhibit at least 95% of the kinase activity of $Ca^{2+}$/calmodulin-dependent protein kinase I (CaMKI) in the population of tumor cells.

According to another embodiment, the pharmaceutical composition is effective to inhibit a kinase activity of BDNF/NT-3 growth factors receptor (TrkB) in the population of tumor cells. According to another embodiment, the pharmaceutical is effective to inhibit at least 50% of the kinase activity of BDNF/NT-3 growth factors receptor (TrkB) in the population of tumor cells. According to another embodiment, the pharmaceutical is effective to inhibit at least 65% of the kinase activity of BDNF/NT-3 growth factors receptor (TrkB) in the population of tumor cells. According to another embodiment, the pharmaceutical is effective to inhibit at least 70% of the kinase activity of BDNF/NT-3 growth factors receptor (TrkB) in the population of tumor cells. According to another embodiment, the pharmaceutical is effective to inhibit at least 75% of the kinase activity of BDNF/NT-3 growth factors receptor (TrkB) in the population of tumor cells.

According to another embodiment, the pharmaceutical composition is effective to inhibit a kinase activity of Mitogen-Activated Protein Kinase-Activated Protein Kinase 2 (MK2) and a kinase activity of Mitogen-Activated Protein Kinase-Activated Protein Kinase 3 (MK3) in the population of tumor cells.

According to another embodiment, the pharmaceutical composition is effective to inhibit a kinase activity of Mitogen-Activated Protein Kinase-Activated Protein Kinase 2 (MK2) and a kinase activity of calcium/calmodulin-dependent protein kinase I (CaMKI) in the population of tumor cells.

According to another embodiment, the pharmaceutical composition is effective to inhibit a kinase activity of Mitogen-Activated Protein Kinase-Activated Protein Kinase 2 (MK2) and a kinase activity of BDNF/NT-3 growth factors receptor (TrkB) in the population of tumor cells.

According to another embodiment, the pharmaceutical composition is effective to inhibit a kinase activity of Mitogen-Activated Protein Kinase-Activated Protein Kinase 2 (MK2), a kinase activity of Mitogen-Activated Protein Kinase-Activated Protein Kinase 3 (MK3), a kinase activity of calcium/calmodulin-dependent protein kinase I (CaMKI), and a kinase activity of BDNF/NT-3 growth factors receptor (TrkB) in the population of tumor cells.

According to another embodiment, the pharmaceutical composition is effective to inhibit a kinase activity of Mitogen-Activated Protein Kinase-Activated Protein Kinase 2 (MK2), a kinase activity of calcium/calmodulin-dependent protein kinase I (CaMKI), and a kinase activity of BDNF/NT-3 growth factors receptor (TrkB) in the population of tumor cells.

According to another embodiment, the pharmaceutical composition is effective to inhibit at least 65% of the kinase activity of Mitogen-Activated Protein Kinase-Activated Protein Kinase 2 (MK2) in the population of tumor cells.

According to another embodiment, the pharmaceutical composition is effective to inhibit at least 65% of the kinase activity of Mitogen-Activated Protein Kinase-Activated Protein Kinase 3 (MK3) in the population of tumor cells.

According to another embodiment, the pharmaceutical composition is effective to inhibit at least 65% of the kinase activity of calcium/calmodulin-dependent protein kinase I (CaMKI) in the population of tumor cells.

According to another embodiment, the pharmaceutical composition is effective to inhibit at least 65% of the kinase activity of BDNF/NT-3 growth factors receptor (TrkB) in the population of tumor cells.

According to another embodiment, the pharmaceutical composition is effective to inhibit at least 65% of the kinase activity of Mitogen-Activated Protein Kinase-Activated Protein Kinase 2 (MK2) and at least 65% of the kinase activity of Mitogen-Activated Protein Kinase-Activated Protein Kinase 3 (MK3) in the population of tumor cells.

According to another embodiment, the pharmaceutical composition is effective to inhibit at least 65% of the kinase activity of Mitogen-Activated Protein Kinase-Activated Protein Kinase 2 (MK2) and at least 65% of the kinase activity of calcium/calmodulin-dependent protein kinase I (CaMKI) in the population of tumor cells.

According to another embodiment, the pharmaceutical composition is effective to inhibit at least 65% of the kinase activity of Mitogen-Activated Protein Kinase-Activated Protein Kinase 2 (MK2) and at least 65% of the kinase activity of BDNF/NT-3 growth factors receptor (TrkB) in the population of tumor cells.

According to another embodiment, the pharmaceutical composition is effective to inhibit at least 65% of the kinase activity of Mitogen-Activated Protein Kinase-Activated Protein Kinase 2 (MK2), at least 65% of the kinase activity of Mitogen-Activated Protein Kinase-Activated Protein Kinase 3 (MK3), at least 65% of the kinase activity of calcium/calmodulin-dependent protein kinase I (CaMKI), and at least 65% of the kinase activity of BDNF/NT-3 growth factors receptor (TrkB) in the population of tumor cells.

According to another embodiment, the pharmaceutical composition is effective to inhibit the kinase activity of at least one kinase selected from the group of MK2, MK3, CaMKI, TrkB in the population of tumor cells, without substantially inhibiting the activity of one or more other selected kinases from the remaining group listed in Table 1 herein in the population of tumor cells.

According to another embodiment, the pharmaceutical composition is effective to inhibit a kinase activity of a kinase selected from the group listed in Table 1 herein in the population of tumor cells.

According to another embodiment, this inhibition may, for example, be effective to reduce proliferation of the population of tumor cells, to reduce tumor size, to reduce tumor burden, to induce tumor cell death, or a combination thereof.

According to some embodiments, inhibitory profiles of MMI inhibitors in vivo depend on dosages, routes of administration, and cell types responding to the inhibitors.

According to such embodiment, the pharmaceutical composition is effective to inhibit less than 50% of the kinase activity of the other selected kinase(s). According to such embodiment, the pharmaceutical composition is effective to inhibit less than 65% of the kinase activity of the other selected kinase(s). According to such embodiment, the pharmaceutical composition is effective to inhibit less than 50% of the kinase activity of the other selected kinase(s). According to another embodiment, the pharmaceutical composition is effective to inhibit less than 40% of the kinase activity of the other selected kinase(s). According to another embodiment, the pharmaceutical composition is effective to inhibit less than 20% of the kinase activity of the other selected kinase(s). According to another embodiment, the pharmaceutical composition is effective to inhibit less than 15% of the kinase activity of the other selected kinase(s). According to another embodiment, the pharmaceutical composition is effective to inhibit less than 10% of the kinase activity of the other selected kinase(s). According to another embodiment, the pharmaceutical composition is effective to inhibit less than 5% of the kinase activity of the other selected kinase(s). According to another embodiment, the pharmaceutical composition is effective to increase the kinase activity of the other selected kinases.

According to the embodiments of the immediately preceding paragraph, the one or more other selected kinase that is not substantially inhibited is selected from the group of $Ca^{2+}$/calmodulin-dependent protein kinase II (CaMKII, including its subunit CaMKIIδ), Proto-oncogene serine/threonine-protein kinase (PIM-1), cellular-Sarcoma (c-SRC), Spleen Tyrosine Kinase (SYK), C-src Tyrosine Kinase (CSK), and Insulin-like Growth Factor 1 Receptor (IGF-1R).

According to some embodiments, the functional equivalent of the polypeptide YARAAARQARAKALARQLGVAA (SEQ ID NO: 1) has a substantial sequence identity to amino acid sequence YARAAARQARAKALARQLGVAA (SEQ ID NO: 1).

According to another embodiments, the functional equivalent of the polypeptide YARAAARQARAKALARQLGVAA (SEQ ID NO: 1) has at least 70 percent sequence identity to amino acid sequence YARAAARQARAKALARQLGVAA (SEQ ID NO: 1). According to another embodiment, the functional equivalent of the polypeptide YARAAARQARAKALARQLGVAA (SEQ ID NO: 1) has at least 80 percent sequence identity to amino acid sequence YARAAARQARAKALARQLGVAA (SEQ ID NO: 1). According to another embodiment, the functional equivalent of the polypeptide YARAAARQARAKALARQLGVAA (SEQ ID NO: 1) has at least 90 percent sequence identity to amino acid sequence YARAAARQARAKALARQLGVAA (SEQ ID NO: 1). According to another embodiment, the functional equivalent of the polypeptide YARAAARQARAKALARQLGVAA (SEQ ID NO: 1) has at least 95 percent sequence identity to amino acid sequence YARAAARQARAKALARQLGVAA (SEQ ID NO: 1).

According to another embodiment, the functional equivalent of the polypeptide YARAAARQARAKALARQLGVAA (SEQ ID NO: 1) is of amino acid sequence FAKLAARLYRKALARQLGVAA (SEQ ID NO: 3).

According to another embodiment, the functional equivalent of the polypeptide YARAAARQARAKALARQLGVAA (SEQ ID NO: 1) is of amino acid sequence KAFAKLAARLYRKALARQLGVAA (SEQ ID NO: 4).

According to another embodiment, the functional equivalent of the polypeptide YARAAARQARAKALARQLGVAA (SEQ ID NO: 1) is of amino acid sequence YARAAARQARAKALARQLAVA (SEQ ID NO: 5).

According to another embodiment, the functional equivalent of the polypeptide YARAAARQARAKALARQLGVAA (SEQ ID NO: 1) is of amino acid sequence YARAAARQARAKALARQLGVA (SEQ ID NO: 6).

According to another embodiment, the functional equivalent of the polypeptide YARAAARQARAKALARQLGVAA (SEQ ID NO: 1) is of amino acid sequence HRRIKAWLKKIKALARQLGVAA (SEQ ID NO: 7).

According to some other embodiments, the functional equivalent of the polypeptide YARAAARQARAKALARQLGVAA (SEQ ID NO: 1) is a fusion protein comprising a first polypeptide operatively linked to a second polypeptide, wherein the first polypeptide is of amino acid sequence YARAAARQARA (SEQ ID NO: 11), and the second polypeptide comprises a therapeutic domain whose sequence has a substantial identity to amino acid sequence KALARQLGVAA (SEQ ID NO: 2).

According to another embodiment, the second polypeptide has at least 70 percent sequence identity to amino acid sequence KALARQLGVAA (SEQ ID NO: 2). According to some other embodiments, the second polypeptide has at least 80 percent sequence identity to amino acid sequence KALARQLGVAA (SEQ ID NO: 2). According to some other embodiments, the second polypeptide has at least 90 percent sequence identity to amino acid sequence KALARQLGVAA (SEQ ID NO: 2). According to some other embodiments, the second polypeptide has at least 95 percent sequence identity to amino acid sequence KALARQLGVAA (SEQ ID NO: 2).

According to another embodiment, the second polypeptide is a polypeptide of amino acid sequence KALARQLAVA (SEQ ID NO: 8).

According to another embodiment, the second polypeptide is a polypeptide of amino acid sequence KALARQLGVA (SEQ ID NO: 9).

According to another embodiment, the second polypeptide is a polypeptide of amino acid sequence KALARQLGVAA (SEQ ID NO: 10).

According to some other embodiments, the functional equivalent of the polypeptide YARAAARQARAKALARQLGVAA (SEQ ID NO: 1) is a fusion protein comprising a first polypeptide operatively linked to a second polypeptide, wherein the first polypeptide comprises a cell penetrating peptide functionally equivalent to YARAAARQARA (SEQ ID NO: 11), and the second polypeptide is of amino acid sequence KALARQLGVAA (SEQ ID NO: 2).

According to a further embodiment, the first polypeptide is a polypeptide of amino acid sequence WLRRIKAWLRRIKA (SEQ ID NO: 12).

According to another embodiment, the first polypeptide is a polypeptide of amino acid sequence WLRRIKA (SEQ ID NO: 13).

According to another embodiment, the first polypeptide is a polypeptide of amino acid sequence YGRKKRRQRRR (SEQ ID NO: 14).

According to another embodiment, the first polypeptide is a polypeptide of amino acid sequence WLRRIKAWLRRI (SEQ ID NO: 15).

According to another embodiment, the first polypeptide is a polypeptide of amino acid sequence FAKLAARLYR (SEQ ID NO: 16).

According to another embodiment, the first polypeptide is a polypeptide of amino acid sequence KAFAKLAARLYR (SEQ ID NO: 17).

According to another embodiment, the first polypeptide is a polypeptide of amino acid sequence HRRIKAWLKKI (SEQ ID NO: 18).

According to another aspect, the described invention also provides an isolated nucleic acid that encodes a protein sequence with at least 70% amino acid sequence identity to amino acid sequence YARAAARQARAKALARQLGVAA (SEQ ID NO: 1). According to some such embodiments, the isolated nucleic acid encodes a protein sequence with at least 80% amino acid sequence identity to amino acid sequence YARAAARQARAKALARQLGVAA (SEQ ID NO: 1). According to some such embodiments, the isolated nucleic acid encodes a protein sequence with at least 90% amino acid sequence identity to amino acid sequence YARAAARQARAKALARQLGVAA (SEQ ID NO: 1). According to some such embodiments, the isolated nucleic acid encodes a protein sequence with at least 95% amino acid sequence identity to amino acid sequence YARAAARQARAKALARQLGVAA (SEQ ID NO: 1).

According to some other embodiments, the therapeutic amount of therapeutic inhibitor peptide of the pharmaceutical composition is of an amount from about 0.000001 mg/kg body weight to about 100 mg/kg body weight. According to another embodiment, the therapeutic amount of therapeutic inhibitory peptide of the pharmaceutical composition is of an amount from about 0.00001 mg/kg body weight to about 100 mg/kg body weight. According to another embodiment, the therapeutic amount of therapeutic inhibitory peptide of the pharmaceutical composition is of an amount from about 0.0001 mg/kg body weight to about 100 mg/kg body weight. According to another embodiment, the therapeutic amount of therapeutic inhibitory peptide of the pharmaceutical composition is of an amount from about 0.001 mg/kg body weight to about 10 mg/kg body weight. According to another embodiment, the therapeutic amount of therapeutic inhibitory peptide of the pharmaceutical composition is of an amount from about 0.01 mg/kg body weight to about 10 mg/kg body weight. According to another embodiment, the therapeutic amount of therapeutic inhibitory peptide of the pharmaceutical composition is of an amount from about 0.1 mg/kg (100 μg/kg) body weight to about 10 mg/kg body weight. According to another embodiment, the therapeutic amount of therapeutic inhibitory peptide of the pharmaceutical composition is of an amount from about 1 mg/kg body weight to about 10 mg/kg body weight. According to another embodiment, the therapeutic amount of therapeutic inhibitory peptide of the pharmaceutical composition is of an amount from about 10 mg/kg body weight to about 100 mg/kg body weight. According to another embodiment, the therapeutic amount of therapeutic inhibitory peptide of the pharmaceutical composition is of an amount from about 2 mg/kg body weight to about 10 mg/kg body weight. According to another embodiment, the therapeutic amount of therapeutic inhibitory peptide of the pharmaceutical composition is of an amount from about 3 mg/kg body weight to about 10 mg/kg body weight. According to another embodiment, the therapeutic amount of therapeutic inhibitory peptide of the pharmaceutical composition is of an amount from about 4 mg/kg body weight to about 10 mg/kg body weight. According to another embodiment, the therapeutic amount of therapeutic inhibitory peptide of the pharmaceutical composition is of an amount from about 5 mg/kg body weight to about 10 mg/kg body weight. According to another embodiment, the therapeutic amount of therapeutic inhibitory peptide of the pharmaceutical composition is of an amount from about 60 mg/kg body weight to about 100 mg/kg body weight. According to another embodiment, the therapeutic amount of therapeutic inhibitory peptide of the pharmaceutical composition is of an amount from about 70 mg/kg body weight to about 100 mg/kg body weight. According to another embodiment, the therapeutic amount of therapeutic inhibitory peptide of the pharmaceutical composition is of an amount from about 80 mg/kg body weight to about 100 mg/kg body weight. According to another embodiment, the therapeutic amount of therapeutic inhibitory peptide of the pharmaceutical composition is of an amount from about 90 mg/kg body weight to about 100 mg/kg body weight. According to another embodiment, the therapeutic amount of therapeutic inhibitor peptide of the pharmaceutical composition is of an amount from about 0.000001 mg/kg body weight to about 90 mg/kg body weight. According to another embodiment, the therapeutic amount of therapeutic inhibitor peptide of the pharmaceutical composition is of an amount from about 0.000001 mg/kg body weight to about 80 mg/kg body weight. According to another embodiment, the therapeutic amount of therapeutic inhibitor peptide of the pharmaceutical composition is of an amount from about 0.000001 mg/kg body weight to about 70 mg/kg body weight. According to another embodiment, the therapeutic amount of therapeutic inhibitor peptide of the pharmaceutical composition is of an amount from about 0.000001 mg/kg body weight to about 60 mg/kg body weight. According to another embodiment, the therapeutic amount of therapeutic inhibitor peptide of the pharmaceutical composition is of an amount from about 0.000001 mg/kg body weight to about 50 mg/kg body weight. According to another embodiment, the therapeutic amount of therapeutic inhibitor peptide of the pharmaceutical composition is of an amount from about 0.000001 mg/kg body weight to about 40 mg/kg body weight. According to another embodiment, the therapeutic amount of therapeutic inhibitor peptide is of an amount from about 0.000001 mg/kg body weight to about 30 mg/kg body weight. According to another embodiment, the therapeutic amount of therapeutic inhibitor peptide of the pharmaceutical composition is of an amount from about 0.000001 mg/kg body weight to about 20 mg/kg body weight. According to another embodiment, the therapeutic amount of therapeutic inhibitor peptide of the pharmaceutical composition is of an amount from about 0.000001 mg/kg body weight to about 10 mg/kg body weight. According to another embodiment, the therapeutic amount of therapeutic inhibitor peptide of the pharmaceutical composition is of an amount from about 0.000001 mg/kg body weight to about 1 mg/kg body weight. According to another embodiment, the therapeutic amount of therapeutic inhibitor peptide of the pharmaceutical composition is of an amount from about 0.000001 mg/kg body weight to about 0.1 mg/kg body weight. According to another embodiment, the therapeutic amount of therapeutic inhibitor peptide of the pharmaceutical composition is of an amount from about 0.000001 mg/kg body weight to about 0.1 mg/kg body weight. According to another embodiment, the therapeutic amount of therapeutic inhibitor peptide of the pharmaceutical composition is of an amount from about 0.000001 mg/kg body weight to about 0.01 mg/kg body weight. According to another embodiment, the therapeutic amount of therapeutic inhibitor peptide of the pharmaceutical composition is of an amount from about 0.000001 mg/kg body weight to about 0.001 mg/kg body weight. According to another embodiment, the therapeutic amount of therapeutic inhibitor peptide of the pharmaceutical composition is of an amount from about 0.000001 mg/kg body weight to about 0.0001 mg/kg body weight. According to another embodiment, the therapeutic amount of therapeutic inhibitor peptide of the pharmaceutical composition is of an amount from about 0.000001 mg/kg body weight to about 0.00001 mg/kg body weight.

According to some other embodiments, the therapeutic dose of therapeutic inhibitor peptide of the pharmaceutical composition ranges from 1 μg/kg/day to 25 μg/kg/day. According to some other embodiments, the therapeutic dose of therapeutic inhibitor peptide of the pharmaceutical composition ranges from 1 μg/kg/day to 2 μg/kg/day. According to some other embodiments, the therapeutic dose of therapeutic inhibitor peptide of the pharmaceutical composition ranges from 2 μg/kg/day to 3 μg/kg/day. According to some other embodiments, the therapeutic dose of therapeutic inhibitor peptide of the pharmaceutical composition ranges from 3 μg/kg/day to 4 μg/kg/day. According to some other embodiments, the therapeutic dose of therapeutic inhibitor peptide of the pharmaceutical ranges from 4 μg/kg/day to 5

µg/kg/day. According to some other embodiments, the therapeutic dose of therapeutic inhibitor peptide of the pharmaceutical composition ranges from 5 µg/kg/day to 6 µg/kg/day. According to some other embodiments, the therapeutic dose of therapeutic inhibitor peptide of the pharmaceutical composition ranges from 6 µg/kg/day to 7 µg/kg/day.

According to some other embodiments, the therapeutic dose of therapeutic inhibitor peptide of the pharmaceutical composition ranges from 7 µg/kg/day to 8 µg/kg/day. According to some other embodiments, the therapeutic dose of therapeutic inhibitor peptide of the pharmaceutical composition ranges from 8 µg/kg/day to 9 µg/kg/day. According to some other embodiments, the therapeutic dose of therapeutic inhibitor peptide of the pharmaceutical composition ranges from 9 µg/kg/day to 10 µg/kg/day. According to some other embodiments, the therapeutic dose of therapeutic inhibitor peptide of the pharmaceutical composition ranges from 1 µg/kg/day to 5 µg/kg/day. According to some other embodiments, the therapeutic dose of therapeutic inhibitor peptide of the pharmaceutical composition ranges from 5 µg/kg/day to 10 µg/kg/day. According to some other embodiments, the therapeutic dose of therapeutic inhibitor peptide of the pharmaceutical composition ranges from 10 µg/kg/day to 15 µg/kg/day. According to some other embodiments, the therapeutic dose of therapeutic inhibitor peptide of the pharmaceutical composition ranges from 15 µg/kg/day to 20 µg/kg/day. According to some other embodiments, the therapeutic dose of therapeutic inhibitor peptide of the pharmaceutical composition ranges from 25 µg/kg/day to 30 µg/kg/day. According to some other embodiments, the therapeutic dose of therapeutic inhibitor peptide of the pharmaceutical composition ranges from 30 µg/kg/day to 35 µg/kg/day. According to some other embodiments, the therapeutic dose of therapeutic inhibitor peptide of the pharmaceutical composition ranges from 35 µg/kg/day to 40 µg/kg/day. According to some other embodiments, the therapeutic dose of therapeutic inhibitor peptide of the pharmaceutical composition ranges from 40 µg/kg/day to 45 µg/kg/day. According to some other embodiments, the therapeutic dose of therapeutic inhibitor peptide of the pharmaceutical composition ranges from 45 µg/kg/day to 50 µg/kg/day. According to some other embodiments, the therapeutic dose of therapeutic inhibitor peptide of the pharmaceutical composition ranges from 50 µg/kg/day to 55 µg/kg/day. According to some other embodiments, the therapeutic dose of therapeutic inhibitor peptide of the pharmaceutical composition ranges from 55 µg/kg/day to 60 µg/kg/day. According to some other embodiments, the therapeutic dose of therapeutic inhibitor peptide of the pharmaceutical composition ranges from 60 µg/kg/day to 65 µg/kg/day. According to some other embodiments, the therapeutic dose of therapeutic inhibitor peptide of the pharmaceutical composition ranges from 65 µg/kg/day to 70 µg/kg/day. According to some other embodiments, the therapeutic dose of therapeutic inhibitor peptide of the pharmaceutical composition ranges from 70 µg/kg/day to 75 µg/kg/day. According to some other embodiments, the therapeutic dose of therapeutic inhibitor peptide of the pharmaceutical composition ranges from 80 µg/kg/day to 85 µg/kg/day. According to some other embodiments, the therapeutic dose of therapeutic inhibitor peptide of the pharmaceutical composition ranges from 85 µg/kg/day to 90 µg/kg/day. According to some other embodiments, the therapeutic dose of therapeutic inhibitor peptide of the pharmaceutical composition ranges from 90 µg/kg/day to 95 µg/kg/day. According to some other embodiments, the therapeutic dose of therapeutic inhibitor peptide of the pharmaceutical composition ranges from 95 µg/kg/day to 100 µg/kg/day.

According to another embodiment, the therapeutic dose of therapeutic inhibitor peptide of the pharmaceutical composition is 1 µg/kg/day.

According to another embodiment, the therapeutic dose of therapeutic inhibitor peptide of the pharmaceutical composition is 2 µg/kg/day.

According to another embodiment, the therapeutic dose of therapeutic inhibitor peptide of the pharmaceutical composition is 5 µg/kg/day.

According to another embodiment, the therapeutic dose of therapeutic inhibitor peptide of the pharmaceutical composition is 10 µg/kg/day.

Within this application, unless otherwise stated, the techniques utilized may be found in any of several well-known references such as: Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, Calif.), "Guide to Protein Purification" in Methods in Enzymology (M. P. Deutshcer, ed., (1990) Academic Press, Inc.); PCR Protocols: A Guide to Methods and Applications (Innis, et al. 1990. Academic Press, San Diego, Calif.), Culture of Animal Cells: A Manual of Basic Technique, 2nd Ed. (R. I. Freshney. 1987. Liss, Inc. New York, N.Y.), and Gene Transfer and Expression Protocols, pp. 109-128, ed. E. J. Murray, The Humana Press Inc., Clifton, N.J.), all of which are incorporated herein by reference.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the described invention, the preferred methods and materials are now described. All publications mentioned herein are incorporated herein by reference to disclose and describe the methods and/or materials in connection with the publications are cited.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges also is encompassed within the invention, subject to any specifically excluded limit in the stated range. Where the stated range includes one or both of the limits, ranges excluding either both of those included limits also are included in the invention.

It must also be noted that as used herein and in the appended claims, the singular forms "a," "and" and "the" include plural referents unless the context clearly dictates otherwise. All technical and scientific terms used herein have the same meaning.

The publications discussed herein are incorporated herein by reference in their entirety and are provided solely for their disclosure prior to the filing date of the present application. Nothing herein is to be construed as an admission that the described invention is not entitled to antedate such publication by virtue of prior invention. Further, the dates of publication provided may be different from the actual publication dates which may need to be independently confirmed.

It should be understood by those skilled in the art that various changes may be made and equivalents may be substituted without departing from the true spirit and scope of the Invention. In addition, many modifications may be made to adapt a particular situation, material, composition of matter, process, process step or steps, to the objective, spirit and scope of the described invention. All such modifications are intended to be within the scope of the claims appended hereto.

EXAMPLES

The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

I. Materials and Methods

MMI-0100 Formulations

Dry Powder Formulations of MMI-0100 (YARAAAR-QARAKALARQLGVAA; SEQ ID NO: 1)

MMI-0100 (YARAAARQARAKALARQLGVAA; SEQ ID NO: 1), Lyophilized (American Peptide, Inc., Sunnyvale Calif.) Lot number 100429, Date of Manufacture 29 Jun. 2010, 500 mg.

Neat Spray Dried MMI-0100 (YARAAARQARAKA-LARQLGVAA; SEQ ID NO: 1), 5% w/w solids (Bend Research, Bend Oreg.) Lot Number BREC 00708-003A, Date of Manufacture 27 Jul. 2012, 1 g.

Neat Spray Dried MMI-0100 (YARAAARQARAKA-LARQLGVAA; SEQ ID NO: 1), 1% w/w solids (Bend Research, Bend Oreg.) Lot Number BREC 00708-003B, Date of Manufacture 27 Jul. 2012, 1 g.

Spray Dried 80/20 MMI-0100 (YARAAARQARAKA-LARQLGVAA; SEQ ID NO: 1)/Trehalose (Santa Cruz Biotechnology, Inc. Dallas Tex.), 1% w/w solids (Bend Research, Bend Oreg.) Lot Number BREC 00708-011C, Date of Manufacture w/c 10 Sep. 2012, 500 mg.

Spray Dried 92.5/7.5 MMI-0100 (YARAAARQARAKA-LARQLGVAA; SEQ ID NO: 1)/Trehalose (Santa Cruz Biotechnology, Inc. Dallas Tex.), 1% w/w solids (Bend Research, Bend Oreg.) Lot Number BREC 00708-011F, Date of Manufacture w/c 10 Sep. 2012, 500 mg.

Nebulizer Formulations of MMI-0100 (YARAAAR-QARAKALARQLGVAA; SEQ ID NO: 1)

Formulation A: 7 mg/mL; 1.8 g of lyophilized peptide weighed into a volumetric flask containing 200 mL of 0.9% saline.

Formulation B: 0.7 mg/mL; 0.18 g of lyophilized peptide weighed into a volumetric flask containing 200 mL of 0.9% saline.

Nano-Polyplex Formulations of MMI-0100 (YARAAAR-QARAKALARQLGVAA; SEQ ID NO: 1)

Synthesis of Cell Penetrant MK2 Inhibitory Peptide

MK2 Inhibitory Peptide (MK2i) MMI-0100 (YARAAARQARAKALARQLGVAA; SEQ ID NO: 1) was synthesized on a PS3 peptide synthesizer (Protein Technologies, Inc. Tucson, Ariz.) utilizing standard Fmoc Chemistry. N-methylpyrrolidone (NMP, Fischer Scientific) was utilized as a solvent in all peptide syntheses. HCTU (1H-Benzotriazolium 1-[bis(dimethylamino)methylene]-5chloro-, hexafluorophosphate (1-),3-oxide) was used as an activator (Chempep, Wellington, Fla.) in the presence of N-methylmorpholine. All amino acids were double coupled in order to maximize yield and purity. Peptides were cleaved/deprotected in trifluoroacetic acid (TFA)/Phenol/$H_2O$/triisopropylsilane (88/5/5/2). The peptide was then further purified by reverse phase HPLC on a Waters 1525 binary HPLC pump outfitted with an extended flow kit, a Waters 2489 UV/Visible detector, and a phenomenex Luna C18(2) AXIA packed column (100A, 250×21.2 mm, 5 micron). A) HPLC grade water with 0.05% formic acid and B) HPLC grade acetonitrile were used as the mobile phase, and the peptide was purified utilizing a 90% A to 90% B gradient over 25 mins (16 mL/min). Acetonitrile was removed from purified fractions with a rotary evaporator, and the purified fractions were then lyophilized. Peptide purity was verified through electrospray ionization mass spectrometry (ESI-MS) on a Waters Synapt ESI-MS.

Monomer and Polymer Synthesis

All reagents were purchased from Sigma and were of analytical grade unless otherwise stated. 2-propylacrylic acid was synthesized according to the procedure outlined by Ferrito et al. (Macromolecular Syntheses 11, 59-62 (1992)) utilizing diethyl propylmalonate (Alfa Aesar) as a precursor. The 4-cyano-4-(ethylsulfanylthiocarbonyl) sulfanylpentanoic acid (ECT) chain transfer agent (CTA) was synthesized as describe by Convertine et al. (J. Control Release 133, 221-229 (2009)). Reversible addition-fragmentation chain transfer (RAFT) polymerization of the poly(propylacrylic acid) (PPAA) homopolymer was carried out in bulk under a nitrogen atmosphere at 70° C. for 48 hours using 2,2'-azo-bis-isobutyrylnitrile (AIBN) as the free radical initiator. The reaction mix was put through three freeze-vacuum-thaw cycles and purged with nitrogen for thirty minutes prior to polymerization. The molar ratio of chain transfer agent (CTA) to AIBN was 1 to 1, and the monomer to CTA ratio was set so that a degree of polymerization of 190 would be achieved at 100% conversion. Following polymerization, the resultant polymer was dissolved in dimethylformamide (DMF) and precipitated into ether 5 times before drying overnight in vacuo. RAFT polymerization of the poly(acrylic acid) (PAA) homopolymer was carried out in distilled dioxane under a nitrogen atmosphere at 70° C. for 18 hours using AIBN as the free radical initiator. The reaction mix was purged with nitrogen for thirty minutes prior to polymerization. The molar ratio of CTA to AIBN was 5 to 1 and the monomer to CTA ratio was set so that a degree of polymerization of 150 would be achieved at 100% conversion. Following polymerization, the resulting polymer was dissolved in dioxane and precipitated into ether 5 times before drying overnight in vacuo. Gel permeation chromatography (GPC, Agilent) was used to determine molecular weight and polydispersity ($M_w/M_n$, PDI) of the PPAA and PAA homopolymers using HPLC-grade DMF containing 0.1% LiBr at 60° C. as the mobile phase. Molecular weight calculations were performed with ASTRA V software (Wyatt Technology) and were based on experimentally-determined dn/dc values determined through offline injections of the polymer through a refractive index detector (calculated PPAA dn/dc=0.087 mL/g, calculated PAA dn/dc=0.09 mL/g).

MMI-0100 Nano-Polyplex (MK2i-NP) Synthesis and Characterization

PPAA was dissolved in 1 M NaOH and diluted into a phosphate buffer (pH 8) to obtain a stock solution. Purified MMI-0100 peptide was dissolved in phosphate buffer (pH 8). The MMI-0100 peptide and PPAA polymer were mixed at a range of charge ratios (CRs) from [$NH_3^+$]:[$COO^-$]=10:1 to 1:10 to form MK2i-NPs. The resulting polyplexes were syringe filtered through 0.45 μm polytetrafluoroethylene (PTFE) filter, and the hydrodynamic diameter and potential were characterized on a Malvern Zetasizer Nano-ZS with a reusable dip cell kit (Malvern Instruments Ltd., Worcestershire, U.K.).

Radiometric $IC_{50}$ Determination

The $IC_{50}$ value was estimated from a 10-point curve of one-half log dilutions. Peptide was supplied in dimethyl sulfoxide (DMSO). Specifically, human recombinant MK2 (h) (5-10 mU) was incubated with 50 mM sodium 3-glycerophosphate (pH=7.5), 0.1 mM EGTA, 30 μM of substrate peptide (KKLNRTLSVA; SEQ ID NO: 21), 10 mM magnesium acetate, and 90 uM γ-$^{33}$P-ATP (final volume of 25 μL) for 40 minutes at room temperature. Then, the reaction was stopped with 3% phosphoric acid. 10 μL of this mixture was spotted onto a P30 filtermat and washed three times for five minutes with 75 mM phosphoric acid and once with methanol. Finally, the membrane was dried and a scintillation counter was used. An ATP concentration within 15 μM of the apparent Km for ATP was chosen, because Hayess and Benndorf (*Biochem Pharmacol*, 1997, 53(9): 1239-47) showed that the mechanism of their original inhibitor peptide (i.e., the peptide KKKALNRQLGVAA; SEQ ID NO: 22) was not competitive with ATP binding.

In addition to determining the $IC_{50}$ value for MMI-0100 (YARAAARQARAKALARQLGVAA; SEQ ID NO: 1), inhibitory activity against 266 human kinases was tested using Millipore's $IC_{50}$ Profiler Express service (Millipore, Billerica, Mass.).

For specificity analysis, 100 μM of each MMI-0100 (YARAAARQARAKALARQLGVAA; SEQ ID NO: 1), MMI-0200 (YARAAARQARAKALNRQLGVA; SEQ ID NO: 19), MMI-0300 (FAKLAARLYRKALARQLGVAA; SEQ ID NO: 3), MMI-0400 (KAFAKLAARLYRKALARQLGVAA; SEQ ID NO: 4), and MMI-0500 (HRRIKAWLKKIKALARQLGVAA; SEQ ID NO: 7), dissolved in dimethyl sulfoxide (DMSO) was used. Every kinase activity measurement was conducted in duplicate.

Cell Lines

All NSCLC (NCI-H520, A549, NCI-H1993, NCI-H460, and NCI-H1299) cell lines can be obtained from the American Tissue and Cell Collection (ATCC). These cells represent different pathological subtypes (e.g., squamous, adeno-carcinoma, carcinoma). A variety of molecular characteristics are also represented including wild-type p53 (A549, H460), reduced or deleted p53 (H520, H1299), wild-type KRAS (H1299), mutated KRAS (A549, H460), wild-type EGFR (A549), mutated EGFR (H1993, H460), and amplified c-met (H1993). All cells can be cultured in RPMI 1640 (Cellgro) with 10% fetal bovine serum (FBS), 1 mM sodium pyruvate, and 10 mM HEPES in 5% $CO_2$ at 37° C. in a humidified tissue culture incubator. Cells can be routinely tested for mycoplasma contamination using a MycoAlert mycoplasma detection kit (Lonza, Rockland, Me.).

II. Results

Example 1

$IC_{50}$ and Specificity of MMI-0100 (YARAAARQARAKALARQLGVAA; SEQ ID NO: 1)

$IC_{50}$ (half maximal inhibitory concentrations) value for the MK2 inhibitor peptides identified below was determined using Millipore's $IC_{50}$ Profiler Express service. This quantitative assay measures how much of an inhibitor is needed to inhibit 50% of a given biological process or component of a process (i.e., an enzyme, cell, or cell receptor) [$IC_{50}$]. Specifically, in these assays, a positively charged substrate is phosphorylated with a radiolabeled phosphate group from an ATP if the kinase is not inhibited by an inhibitor peptide. The positively charged substrate then is attracted to a negatively charged filter membrane, quantified with a scintillation counter, and compared to a 100% activity control.

ATP concentrations within 15 μM of the apparent Km for ATP were chosen since an ATP concentration near the Km may allow for the kinases to have the same relative amount of phosphorylation activity. The $IC_{50}$ of the polypeptide of amino acid sequence YARAAARQARAKALARQLGVAA; SEQ ID NO: 1 (MMI-0100) was determined to be 22 μM.

In addition to determining the $IC_{50}$ of MMI-0100, the specificity of MK2 inhibitory peptides was assessed by examining activities of all 266 human kinases available for testing in the Millipore kinase profiling service (Table 1). For analysis, the kinases that were inhibited more than 65% by MMI-0100 (YARAAARQARAKALARQLGVAA; SEQ ID NO: 1); MMI-0200 (YARAAARQARAKALNRQLGVA; SEQ ID NO: 19); MMI-0300 (FAKLAARLYRKALARQLGVAA; SEQ ID NO: 3); MMI-0400 (KAFAKLAARLYRKALARQLGVAA; SEQ ID NO: 4); and MMI-0500 (HRRIKAWLKKIKALARQLGVAA; SEQ ID NO: 7) were determined.

As shown in Table 1, at 100 μM, MK2 inhibitory peptides MMI-0100 (SEQ ID NO: 1), MMI-0200 (SEQ ID NO: 19), MMI-0300 (SEQ ID NO: 3); MMI-0400 (SEQ ID NO: 4); and MMI-0500 (SEQ ID NO: 5) inhibited a specific group of kinases and showed very limited off-target kinase inhibition. More specifically, MK2 inhibitory peptides MMI-0100 (SEQ ID NO: 1), MMI-0200 (SEQ ID NO: 19), MMI-0300 (SEQ ID NO: 3); MMI-0400 (SEQ ID NO: 4); and MMI-0500 (SEQ ID NO: 5) inhibited in vitro more than 65% of the kinase activities of Mitogen-Activated Protein Kinase-Activated Protein Kinase 2 (MK2), Mitogen-Activated Protein Kinase-Activated Protein Kinase 3 (MK3), Calcium/Calmodulin-Dependent Protein Kinase I (CaMKI, serine/threonine-specific protein kinase), and BDNF/NT-3 growth factors receptor (TrkB, tyrosine kinase).

TABLE 1

Kinase Profiling Assay

| | MMI-0100 (SEQ ID NO: 1) (100 μM) | MMI-0200 (SEQ ID NO: 19) (100 μM) | MMI-0300 (SEQ ID NO: 3) (100 μM) | MMI-0400 (SEQ ID NO: 4) (100 μM) | MMI-0500 (SEQ ID NO: 7) (100 μM) |
|---|---|---|---|---|---|
| Abl(h) | 136 | 107 | 69 | 84 | 16 |
| Abl(H396P)(h) | 130 | 121 | 101 | 105 | 51 |
| Abl(M351T)(h) | 128 | 119 | 90 | 121 | 61 |

TABLE 1-continued

| Kinase Profiling Assay | | | | | |
|---|---|---|---|---|---|
| | MMI-0100 (SEQ ID NO: 1) (100 μM) | MMI-0200 (SEQ ID NO: 19) (100 μM) | MMI-0300 (SEQ ID NO: 3) (100 μM) | MMI-0400 (SEQ ID NO: 4) (100 μM) | MMI-0500 (SEQ ID NO: 7) (100 μM) |
| Abl(Q252H)(h) | 105 | 107 | 82 | 98 | 40 |
| Abl(T315I)(h) | 98 | 108 | 97 | 105 | 16 |
| Abl(Y253F)(h) | 104 | 102 | 86 | 78 | 29 |
| ACK1(h) | 106 | 97 | 104 | 95 | 64 |
| ALK(h) | 118 | 95 | 19 | 16 | 12 |
| ALK4(h) | 124 | 152 | 140 | 130 | 81 |
| Arg(h) | 89 | 82 | 72 | 84 | 22 |
| AMPKα1(h) | 107 | 108 | 71 | 87 | 35 |
| AMPKα2(h) | 121 | 88 | 54 | 58 | 9 |
| ARK5(h) | 108 | 93 | 78 | 69 | 20 |
| ASK1(h) | 100 | 101 | 80 | 69 | -4 |
| Aurora-A(h) | 120 | 107 | 92 | 119 | 110 |
| Aurora-B(h) | 94 | 166 | 128 | 150 | 5 |
| Axl(h) | 81 | 99 | 52 | 41 | 12 |
| Bmx(h) | 62 | 76 | N/D | 26 | 45 |
| BRK(h) | 70 | 127 | 35 | 18 | 41 |
| BrSK1(h) | 100 | 93 | 67 | 76 | 72 |
| BrSK2(h) | 129 | 102 | 83 | 86 | 84 |
| BTK(h) | 112 | 100 | 102 | 94 | 18 |
| BTK(R28H)(h) | 91 | 104 | 74 | 24 | 10 |
| CaMKI(h) | 13 | 21 | 1 | 0 | -1 |
| CaMKIIβ(h) | 58 | 53 | 2 | 11 | 3 |
| CaMKIIγ(h) | 106 | 94 | 5 | 3 | 3 |
| CaMKIδ(h) | 59 | 47 | 10 | 17 | 0 |
| CaMKIIδ(h) | 89 | 2 | 1 | 2 | 1 |
| CaMKIV(h) | 87 | 71 | 17 | 18 | -1 |
| CDK1/cyclinB(h) | 96 | 115 | 73 | 74 | 57 |
| CDK2/cyclinA(h) | 97 | 114 | 86 | 92 | 87 |
| CDK2/cyclinE(h) | 106 | 112 | 94 | 83 | 19 |
| CDK3/cyclinE(h) | 106 | 104 | 94 | 92 | 8 |
| CDK5/p25(h) | 114 | 97 | 89 | 92 | 66 |
| CDK5/p35(h) | 94 | 92 | 79 | 76 | 59 |
| CDK6/cyclinD3(h) | 103 | 100 | 86 | 85 | 23 |
| CDK7/cyclinH/MAT1(h) | 89 | 67 | 65 | 47 | 15 |
| CDK9/cyclin T1(h) | 228 | 103 | 91 | 235 | 6 |
| CHK1(h) | 97 | 115 | 91 | 87 | 65 |
| CHK2(h) | 104 | 105 | 66 | 54 | 13 |

TABLE 1-continued

Kinase Profiling Assay

| | MMI-0100 (SEQ ID NO: 1) (100 µM) | MMI-0200 (SEQ ID NO: 19) (100 µM) | MMI-0300 (SEQ ID NO: 3) (100 µM) | MMI-0400 (SEQ ID NO: 4) (100 µM) | MMI-0500 (SEQ ID NO: 7) (100 µM) |
|---|---|---|---|---|---|
| CHK2 (I157T) (h) | 97 | 85 | 43 | 41 | 3 |
| CHK2 (R145W) (h) | 97 | 81 | 33 | 31 | 3 |
| CK1γ1 (h) | 110 | 98 | 111 | 116 | 109 |
| CK1γ2 (h) | 119 | 104 | 123 | 114 | 119 |
| CK1γ3 (h) | 105 | 96 | 125 | 115 | 114 |
| CK1δ (h) | 115 | 92 | 92 | 93 | 78 |
| CK2 (h) | 90 | 83 | 90 | 101 | 93 |
| CK2α2 (h) | 104 | 88 | 105 | 96 | 103 |
| CLK2 (h) | 88 | 97 | 103 | 116 | 116 |
| CLK3 (h) | 108 | 76 | 61 | 84 | 76 |
| cKit (h) | 95 | 110 | 53 | 43 | 45 |
| cKit (D816V) (h) | 117 | 118 | 60 | 35 | 30 |
| cKit (D816H) (h) | 79 | 106 | 126 | 143 | 194 |
| cKit (V560G) (h) | 94 | 115 | 102 | 124 | 198 |
| cKit (V654A) (h) | 69 | 113 | 134 | 150 | 223 |
| CSK (h) | 70 | 33 | 49 | 16 | 2 |
| c-RAF (h) | 97 | 115 | 107 | 102 | 19 |
| cSRC (h) | 70 | 32 | 26 | 14 | 30 |
| DAPK1 (h) | 97 | 113 | 46 | 36 | 0 |
| DAPK2 (h) | 41 | 92 | 32 | 16 | 3 |
| DCAMKL2 (h) | 146 | 131 | 81 | 70 | 56 |
| DDR2 (h) | 105 | 104 | 94 | 95 | 79 |
| DMPK (h) | 60 | 66 | 59 | 54 | 12 |
| DRAK1 (h) | 47 | 34 | 14 | 14 | 8 |
| DYRK2 (h) | 99 | 142 | 155 | 195 | 127 |
| eEF-2K (h) | 113 | 136 | 91 | 43 | 43 |
| EGFR (h) | 95 | 83 | 21 | 16 | −1 |
| EGFR (L858R) (h) | 76 | 120 | N/D | 52 | 26 |
| EGFR (L861Q) (h) | 53 | 74 | 25 | 22 | 15 |
| EGFR (T790M) (h) | 106 | 113 | 100 | 106 | 70 |
| EGFR (T790M, L858R) (h) | 93 | 108 | 85 | 78 | 53 |
| EphA1 (h) | 114 | 136 | 73 | 61 | 40 |
| EphA2 (h) | 58 | 95 | 31 | 17 | N/D |
| EphA3 (h) | 107 | 117 | 6 | 12 | 33 |
| EphA4 (h) | 110 | 127 | 88 | 65 | 48 |
| EphA5 (h) | 110 | 123 | 18 | 24 | 42 |
| EphA7 (h) | 193 | 220 | 159 | 222 | 189 |

TABLE 1-continued

Kinase Profiling Assay

| | MMI-0100 (SEQ ID NO: 1) (100 µM) | MMI-0200 (SEQ ID NO: 19) (100 µM) | MMI-0300 (SEQ ID NO: 3) (100 µM) | MMI-0400 (SEQ ID NO: 4) (100 µM) | MMI-0500 (SEQ ID NO: 7) (100 µM) |
|---|---|---|---|---|---|
| EphA8(h) | 181 | 133 | 93 | 146 | 337 |
| EphB2(h) | 68 | 128 | 18 | 22 | 70 |
| EphB1(h) | 99 | 95 | 44 | 58 | 37 |
| EphB3(h) | 109 | 128 | 62 | 47 | 79 |
| EphB4(h) | 62 | 131 | 44 | 28 | 38 |
| ErbB4(h) | 73 | 82 | 40 | 0 | 2 |
| FAK(h) | 98 | 110 | 111 | 96 | 94 |
| Fer(h) | 117 | 101 | 130 | 108 | 196 |
| Fes(h) | 44 | 74 | 20 | 16 | 23 |
| FGFR1(h) | 120 | 97 | 55 | 59 | 18 |
| FGFR1(V561M)(h) | 108 | 72 | 74 | 74 | 113 |
| FGFR2(h) | 49 | 73 | 14 | 18 | 12 |
| FGFR2(N549H)(h) | 95 | 104 | 116 | 112 | 105 |
| FGFR3(h) | 73 | 208 | 102 | 0 | 10 |
| FGFR4(h) | 67 | 75 | 28 | 19 | 3 |
| Fgr(h) | 54 | 71 | 60 | 47 | 109 |
| Flt1(h) | 109 | 96 | 69 | 48 | 27 |
| Flt3(D835Y)(h) | 120 | 115 | 80 | 71 | 65 |
| Flt3(h) | 104 | 99 | 84 | 18 | 17 |
| Flt4(h) | 135 | 105 | 83 | 89 | 73 |
| Fms(h) | 89 | 92 | 45 | 37 | 14 |
| Fms(Y969C)(h) | 126 | 88 | 72 | 91 | N/D |
| Fyn(h) | 71 | 75 | 74 | 54 | 83 |
| GCK(h) | 98 | 99 | 70 | 66 | 30 |
| GRK5(h) | 117 | 135 | 136 | 131 | 116 |
| GRK6(h) | 131 | 132 | 147 | 141 | 174 |
| GRK7(h) | 111 | 124 | 122 | 100 | 93 |
| GSK3α(h) | 183 | 119 | 157 | 164 | 175 |
| GSK3β(h) | 113 | 132 | 205 | 202 | 238 |
| Haspin(h) | 127 | 71 | 48 | 36 | 25 |
| Hck(h) | 354 | 107 | 72 | 72 | 78 |
| Hck(h) activated | 58 | 100 | 82 | 81 | 67 |
| HIPK1(h) | 94 | 115 | 74 | 91 | 47 |
| HIPK2(h) | 98 | 102 | 73 | 90 | 38 |
| HIPK3(h) | 105 | 105 | 93 | 105 | 85 |
| IGF-1R(h) | 102 | 49 | 119 | 90 | 117 |
| IGF-1R(h), activated | 126 | 94 | 80 | 77 | 45 |

TABLE 1-continued

Kinase Profiling Assay

| | MMI-0100 (SEQ ID NO: 1) (100 μM) | MMI-0200 (SEQ ID NO: 19) (100 μM) | MMI-0300 (SEQ ID NO: 3) (100 μM) | MMI-0400 (SEQ ID NO: 4) (100 μM) | MMI-0500 (SEQ ID NO: 7) (100 μM) |
|---|---|---|---|---|---|
| IKKα(h) | 108 | 104 | 93 | 87 | 50 |
| IKKβ(h) | 105 | 109 | 84 | 84 | 71 |
| IR(h) | 112 | 90 | 96 | 85 | 95 |
| IR(h), activated | 127 | 105 | 79 | 59 | 90 |
| IRR(h) | 85 | 69 | 8 | 8 | 10 |
| IRAK1(h) | 97 | 101 | 95 | 93 | 5 |
| IRAK4(h) | 100 | 110 | 59 | 59 | 3 |
| Itk(h) | 99 | 98 | 77 | 63 | 7 |
| JAK2(h) | 89 | 131 | 133 | 119 | 49 |
| JAK3(h) | 150 | 117 | 121 | 122 | 95 |
| JNK1α1(h) | 91 | 106 | 97 | 98 | 109 |
| JNK2α2(h) | 114 | 109 | 98 | 96 | 81 |
| JNK3(h) | 104 | 90 | 89 | 70 | 171 |
| KDR(h) | 100 | 110 | 101 | 94 | 15 |
| Lck(h) | 346 | 113 | -2 | 228 | 359 |
| Lck(h) activated | 106 | 90 | 243 | 216 | 76 |
| LIMK1(h) | 103 | 109 | 88 | 92 | 87 |
| LKB1(h) | 111 | 99 | 101 | 89 | 51 |
| LOK(h) | 37 | 67 | 37 | 18 | 7 |
| Lyn(h) | 113 | 98 | 69 | 3 | 31 |
| MAPK1(h) | 108 | 97 | 107 | 100 | 102 |
| MAPK2(h) | 98 | 105 | 98 | 93 | 60 |
| MAPKAP-K2(h) | 19 | 35 | 5 | 5 | 9 |
| MAPKAP-K3(h) | 27 | 39 | 3 | 7 | 9 |
| MEK1(h) | 86 | 116 | 77 | 77 | 21 |
| MARK1(h) | 109 | 102 | 132 | 120 | 110 |
| MELK(h) | 74 | 59 | 16 | 17 | 0 |
| Mer(h) | 47 | 90 | 52 | 50 | 17 |
| Met(h) | 104 | 71 | 65 | 62 | 27 |
| Met(D1246H)(h) | 99 | 139 | 125 | 68 | 150 |
| Met(D1246N)(h) | 114 | 149 | 82 | 31 | 90 |
| Met(M1268T)(h) | 114 | 143 | 255 | 265 | 239 |
| Met(Y1248C)(h) | 77 | 141 | 84 | 36 | 73 |
| Met(Y1248D)(h) | 87 | 118 | 102 | 31 | 218 |
| Met(Y1248H)(h) | 88 | 153 | 117 | 63 | 126 |
| MINK(h) | 96 | 103 | 48 | 52 | 5 |
| MKK6(h) | 74 | 98 | 48 | 44 | 18 |

TABLE 1-continued

Kinase Profiling Assay

| | MMI-0100 (SEQ ID NO: 1) (100 μM) | MMI-0200 (SEQ ID NO: 19) (100 μM) | MMI-0300 (SEQ ID NO: 3) (100 μM) | MMI-0400 (SEQ ID NO: 4) (100 μM) | MMI-0500 (SEQ ID NO: 7) (100 μM) |
|---|---|---|---|---|---|
| MKK7β(h) | 137 | 117 | 100 | 94 | 102 |
| MLCK(h) | 85 | 103 | 2 | 1 | 0 |
| MLK1(h) | 77 | 84 | 40 | 33 | 43 |
| Mnk2(h) | 94 | 106 | 89 | 86 | 6 |
| MRCKα(h) | 98 | 103 | 104 | 97 | 5 |
| MRCKβ(h) | 103 | 102 | 83 | 71 | −10 |
| MSK1(h) | 52 | 50 | 32 | 28 | 8 |
| MSK2(h) | 105 | 88 | 56 | 52 | 14 |
| MSSK1(h) | 82 | 100 | 77 | 75 | 22 |
| MST1(h) | 85 | 72 | 14 | 6 | 3 |
| MST2(h) | 98 | 104 | 19 | 11 | 2 |
| MST3(h) | 104 | 95 | 45 | 36 | 4 |
| mTOR(h) | 102 | 110 | 91 | 93 | 135 |
| mTOR/FKBP12(h) | 117 | 118 | 145 | 125 | 140 |
| MuSK(h) | 85 | 106 | 93 | 93 | 27 |
| NEK2(h) | 102 | 97 | 78 | 61 | 0 |
| NEK3(h) | 100 | 100 | 92 | 85 | 20 |
| NEK6(h) | 109 | 98 | 82 | 85 | 49 |
| NEK7(h) | 97 | 96 | 84 | 87 | 89 |
| NEK11(h) | 102 | 95 | 53 | 33 | 2 |
| NLK(h) | 100 | 106 | 87 | 90 | 19 |
| p70S6K(h) | 89 | 84 | 35 | 33 | 3 |
| PAK2(h) | 71 | 69 | 65 | 59 | 44 |
| PAK4(h) | 92 | 98 | 94 | 89 | 86 |
| PAK3(h) | N/D | 50 | 140 | 121 | 102 |
| PAK5(h) | 97 | 100 | 110 | 117 | 125 |
| PAK6(h) | 121 | 105 | 104 | 100 | 107 |
| PAR-1Bα(h) | 62 | 110 | 113 | 109 | 97 |
| PASK(h) | 81 | 60 | 29 | 28 | 9 |
| PDGFRα(h) | 104 | 108 | 65 | 40 | 40 |
| PDGFRα(D842V)(h) | 103 | 107 | 114 | 118 | 170 |
| PDGFRα(V561D)(h) | 58 | 106 | 82 | 100 | 146 |
| PDGFRβ(h) | 116 | 137 | 81 | 53 | 40 |
| PDK1(h) | 144 | 143 | 135 | 159 | 178 |
| PhKγ2(h) | 62 | 86 | 46 | 38 | 16 |
| Pim-1(h) | 44 | 18 | 8 | 7 | 0 |
| Pim-2(h) | 117 | 74 | 76 | 92 | 46 |

TABLE 1-continued

Kinase Profiling Assay

| | MMI-0100 (SEQ ID NO: 1) (100 μM) | MMI-0200 (SEQ ID NO: 19) (100 μM) | MMI-0300 (SEQ ID NO: 3) (100 μM) | MMI-0400 (SEQ ID NO: 4) (100 μM) | MMI-0500 (SEQ ID NO: 7) (100 μM) |
|---|---|---|---|---|---|
| Pim-3(h) | 98 | 94 | 80 | 80 | 37 |
| PKA(h) | 138 | 110 | 119 | 119 | 118 |
| PKBα(h) | 140 | 110 | 57 | 67 | 30 |
| PKBβ(h) | 284 | 250 | 84 | 98 | 21 |
| PKBγ(h) | 105 | 103 | 20 | 41 | 20 |
| PKCα(h) | 94 | 100 | 89 | 86 | 3 |
| PKCβI(h) | 88 | 98 | 78 | 78 | 1 |
| PKCβII(h) | 102 | 100 | 82 | 75 | 3 |
| PKCγ(h) | 94 | 101 | 89 | 79 | 6 |
| PKCδ(h) | 100 | 101 | 101 | 90 | 61 |
| PKCε(h) | 102 | 98 | 79 | 59 | 23 |
| PKGη(h) | 105 | 101 | 103 | 98 | 45 |
| PKCτ(h) | 110 | 97 | 68 | 46 | 7 |
| PKCμ(h) | 79 | 73 | 22 | 14 | 10 |
| PKCθ(h) | 102 | 101 | 88 | 76 | 62 |
| PKCζ(h) | 82 | 98 | 81 | 75 | 7 |
| PKD2(h) | 84 | 78 | 33 | 25 | 10 |
| PKG1γ(h) | 82 | 70 | 64 | 58 | 25 |
| PKG1β(h) | 71 | 57 | 50 | 53 | 24 |
| Plk1(h) | 109 | 128 | 115 | 119 | 104 |
| Plk3(h) | 107 | 107 | 127 | 129 | 122 |
| PRAK(h) | 159 | 115 | 128 | 118 | 95 |
| PRK2(h) | 72 | 74 | 33 | 27 | 7 |
| PrKX(h) | 84 | 112 | 61 | 76 | 57 |
| PTK5(h) | 135 | 108 | 132 | 129 | 96 |
| Pyk2(h) | 113 | 127 | 47 | 34 | 46 |
| Ret(h) | 108 | 96 | 140 | 145 | 174 |
| Ret(V804L)(h) | 113 | 100 | 79 | 73 | 20 |
| Ret(V804M)(h) | 92 | 105 | 95 | 87 | 36 |
| RIPK2(h) | 92 | 98 | 97 | 98 | 30 |
| ROCK-I(h) | 99 | 117 | 79 | 73 | 17 |
| ROCK-II(h) | 102 | 85 | 74 | 77 | 2 |
| Ron(h) | 117 | 120 | 93 | 79 | 46 |
| Ros(h) | 107 | 86 | 95 | 99 | 150 |
| Rse(h) | 109 | 88 | 88 | 89 | 63 |
| Rsk1(h) | 86 | 102 | 46 | 54 | 34 |
| Rsk2(h) | 65 | 101 | 51 | 38 | 14 |

TABLE 1-continued

Kinase Profiling Assay

| | MMI-0100 (SEQ ID NO: 1) (100 µM) | MMI-0200 (SEQ ID NO: 19) (100 µM) | MMI-0300 (SEQ ID NO: 3) (100 µM) | MMI-0400 (SEQ ID NO: 4) (100 µM) | MMI-0500 (SEQ ID NO: 7) (100 µM) |
|---|---|---|---|---|---|
| Rsk3(h) | 76 | 109 | 76 | 71 | 23 |
| Rsk4(h) | 99 | 125 | 90 | 91 | 29 |
| SAPK2a(h) | 110 | 107 | 90 | 85 | 52 |
| SAPK2a(T106M)(h) | 101 | 100 | 97 | 99 | 32 |
| SAPK2b(h) | 99 | 95 | 81 | 82 | 42 |
| SAPK3(h) | 106 | 97 | 84 | 79 | 24 |
| SAPK4(h) | 98 | 106 | 96 | 91 | 48 |
| SGK(h) | 128 | 115 | 48 | 54 | 2 |
| SGK2(h) | 103 | 119 | 56 | 98 | −1 |
| SGK3(h) | 95 | 58 | 10 | 8 | −3 |
| SIK(h) | 113 | 102 | 66 | 68 | 40 |
| Snk(h) | 94 | 109 | 114 | 131 | 122 |
| Src(1-530)(h) | 95 | 75 | 23 | 19 | 21 |
| Src(T341M)(h) | 98 | 56 | 70 | 76 | 59 |
| SRPK1(h) | 69 | 93 | 90 | 96 | 80 |
| SRPK2(h) | 92 | 100 | 106 | 97 | 80 |
| STK33(h) | 99 | 98 | 45 | 52 | 16 |
| Syk(h) | 45 | 36 | 24 | 9 | 5 |
| TAK1(h) | 116 | 124 | 122 | 177 | N/D |
| TAO1(h) | 99 | 105 | 82 | 73 | 24 |
| TAO2(h) | 95 | 93 | 70 | 74 | 15 |
| TAO3(h) | 45 | 102 | 77 | 67 | 12 |
| TBK1(h) | 106 | 98 | 37 | 39 | 16 |
| Tec(h) activated | 100 | 77 | 56 | 29 | 33 |
| Tie2(h) | 28 | 53 | 26 | 21 | 22 |
| Tie2(R849W)(h) | 102 | 89 | 117 | 108 | 106 |
| Tie2(Y897S)(h) | 99 | 85 | 83 | 87 | 80 |
| TLK2(h) | 113 | 129 | 114 | 151 | 133 |
| TrkA(h) | 74 | N/D | 25 | 17 | 24 |
| TrkB(h) | 4 | 7 | 5 | 8 | 12 |
| TSSK1(h) | 99 | 98 | 79 | 79 | 46 |
| TSSK2(h) | 107 | 91 | 98 | 94 | 92 |
| Txk(h) | 87 | 98 | 48 | 37 | 10 |
| ULK2(h) | 123 | 132 | 122 | 131 | 124 |
| ULK3(h) | 142 | 164 | 167 | 147 | 177 |
| WNK2(h) | 95 | 94 | 64 | 54 | 8 |
| WNK3(h) | 100 | 97 | 77 | 74 | 9 |

TABLE 1-continued

Kinase Profiling Assay

| | MMI-0100 (SEQ ID NO: 1) (100 µM) | MMI-0200 (SEQ ID NO: 19) (100 µM) | MMI-0300 (SEQ ID NO: 3) (100 µM) | MMI-0400 (SEQ ID NO: 4) (100 µM) | MMI-0500 (SEQ ID NO: 7) (100 µM) |
|---|---|---|---|---|---|
| VRK2(h) | 112 | 109 | 161 | 185 | 169 |
| Yes(h) | 49 | 93 | 67 | 14 | N/D |
| ZAP-70(h) | 79 | 58 | 75 | 33 | 1 |
| ZIPK(h) | 80 | 67 | 28 | 13 | 1 |

N/D: % activity could not be determined as the duplicates.
MMI-0100: YARAAARQARAKALARQLGVAA (SEQ ID NO: 1)
MMI-0200: YARAAARQARAKALNRQLGVA (SEQ ID NO: 19)
MMI-0300: FAKLAARLYRKALARQLGVAA (SEQ ID NO: 3)
MMI-0400: KAFAKLAARLYRKALARQLGVAA (SEQ ID NO: 4)
MMI-0500: HRRIKAWLKKIKALARQLGVAA (SEQ ID NO: 7)

Example 2

Inhibition of NSCLC Cell Proliferation by MK2 Inhibitor Peptides

A cell proliferation assay can be employed to determined inhibition of NSCLC cell proliferation by MK2 inhibitor peptides. For example, NCI-H520, A549, NCI-H1993, NCI-H460, and NCI-H1299 cells (ATCC) can be seeded in 96-well plates and cultured overnight. Cell cultures can be exposed to various concentrations of YARAAARQARAKALARQLGVAA (SEQ ID NO: 1; MMI-0100), YARAAARQARAKALNRQLGVA (SEQ ID NO: 19; MMI-0200), FAKLAARLYRKALARQLGVAA (SEQ ID NO: 3; MMI-0300), KAFAKLAARLYRKALARQLGVAA (SEQ ID NO: 4; MMI-0400), HRRIKAWLKKIKALARQLGVAA (SEQ ID NO: 7; MMI-0500), YARAAARDARAKALNRQLAVAA (SEQ ID NO: 23; MMI-0600), and YARAAARQARAKALNRQLAVA (SEQ ID NO: 24; MMI-0600-2) for specified treatment intervals. Proliferation of NSCLC cells can be determined by 3-[4,5-dimethylthiazol-2-yl]-2,5-diphenyltetrazolium bromide (MTT) assay (Life Technologies, Grand Island, N.Y.). Briefly, for adherent cells, medium is removed and replaced with 100 µL of fresh culture medium. For non-adherent cells, microplates are centrifuged to pellet NSCLC cells, the medium is removed and replaced with 100 µL of fresh medium. MTT dye (2 mg/ml) is added, and the cells are incubated for 4 hours at 37° C. Next, medium is removed and the resulting formazan crystals are dissolved in DMSO (Sigma-Aldrich, St. Louis, Mo.) for 5 minutes. Microplates are read in a spectrophotometer at 540 nm. Dose response curves can be created using GraphPad Prism version 5.01 (GraphPad Software Inc, La Jolla, Calif.). $IC_{50}$ values can be calculated using CalcuSyn (Biosoft, Great Shelford, Cambridge, UK).

Example 3

Cytotoxicity of MK2 Inhibitor Peptides

The cytotoxic effects of MK2 inhibitor peptides on NSCLC cells can be determined. For example, NCI-H520, A549, NCI-H1993, NCI-H460, and NCI-H1299 cells (ATCC) can be seeded in 6-well plates and cultured overnight. NSCLC cell cultures can be left untreated or treated with predetermined $IC_{50}$ doses of YARAAARQARAKALARQLGVAA (SEQ ID NO: 1; MMI-0100), YARAAARQARAKALNRQLGVA (SEQ ID NO: 19; MMI-0200), FAKLAARLYRKALARQLGVAA (SEQ ID NO: 3; MMI-0300), KAFAKLAARLYRKALARQLGVAA (SEQ ID NO: 4; MMI-0400), HRRIKAWLKKIKALARQLGVAA (SEQ ID NO: 7; MMI-0500), YARAAARDARAKALNRQLAVAA (SEQ ID NO: 23; MMI-0600), and YARAAARQARAKALNRQLAVA (SEQ ID NO: 24; MMI-0600-2) and incubated for 48, 72 or 96 hours. After each time point, media containing any non-adherent cells can be collected. Adherent cells can be detached using trypsin (Life Technologies, Grand Island, N.Y.), suspended in culture medium and disaggregated by manual pipetting. All collected NSCLC cells can be mixed with trypan blue dye (Life Technologies). Viable cells that exclude the dye and dead cells that stain blue can be counted using a hemocytometer.

Example 4

Apoptosis of NSCLC Cells by MK2 Inhibitor Peptides

Activation of caspase enzymes is a distinctive feature of the early stages of apoptosis. A microplate assay for caspase activity can be performed to determine apoptosis of NSCLC cells by MK2 inhibitor peptides. For example, NCI-H520, A549, NCI-H1993, NCI-H460, and NCI-H1299 cells (ATCC) can be seeded in 96-well plates and cultured overnight. NSCLC cell cultures can be left untreated or treated with predetermined $IC_{50}$ doses of YARAAARQARAKALARQLGVAA (SEQ ID NO: 1; MMI-0100), YARAAARQARAKALNRQLGVA (SEQ ID NO: 19; MMI-0200), FAKLAARLYRKALARQLGVAA (SEQ ID NO: 3; MMI-0300), KAFAKLAARLYRKALARQLGVAA (SEQ ID NO: 4; MMI-0400), HRRIKAWLKKIKALARQLGVAA (SEQ ID NO: 7; MMI-0500), YARAAARDARAKALNRQLAVAA (SEQ ID NO: 23; MMI-0600), and YARAAARQARAKALNRQLAVA (SEQ ID NO: 24; MMI-0600-2) and incubated for 48, 72 or 96 hours. After each time point, CellEvent™ Caspase-3/7 Green Detection Reagent (Life Technologies) can be added to each well at a final concentration of between 2-8 µM and incubated at 37° C. for 30 minutes. After incubation, cells can be imaged using a microplate reader with fluorescence detection (e.g., Gemini XPS Microplate Reader, Molecular Devices, Sunnyvale, Calif.) with filter sets capable of detecting 502/530 nm excitation/emission maxima.

Example 5

In Vivo Treatment of NSCLC Cells by MK2 Inhibitor Peptides

Orthotopic lung tumor implantation can be use to evaluate the effect of MK2 inhibitor peptides on non-small cell lung cancer (NSCLC) tumors. For example, four to six week old female Sprague Dawley nude mice (Harlan Laboratories) can be used to establish orthotopic lung tumors as described by Peng et al. (Nanomedicine. 2014 October; 10(7): 1497-1506). Briefly, after mice are anesthetized, a 5 mm incision is made on the dorsal side over the left lung. Fat and muscles are separated to visualize lung movement. Five million ($5 \times 10^6$) A549 human lung adenocardinoma epithelial cells (ATCC) suspended in 40 µL PBS/matrigel (BD Biosciences) are injected directly into the left lung parenchyma at a depth of 3 mm (day 0). Mice are randomized into 8 groups: untreated control group; YARAAARQARAKALARQL-GVAA (SEQ ID NO: 1; MMI-0100) group; YARAAAR-QARAKALNRQLGVA (SEQ ID NO: 19; MMI-0200) group; FAKLAARLYRKALARQLGVAA (SEQ ID NO: 3; MMI-0300) group; KAFAKLAARLYRKALARQLGVAA (SEQ ID NO: 4; MMI-0400) group; HRRIKAWLKKIKA-LARQLGVAA (SEQ ID NO: 7; MMI-0500) group; YARAAARDARAKALNRQLAVAA (SEQ ID NO: 23; MMI-0600) group; and YARAAARQARAKALNRQLAVA (SEQ ID NO: 24; MMI-0600-2) group. Treatments are started as intravenous (IV) injections on day 16 with a treatment schedule of once a day every 7 days for 6 doses (Q7d x6). Mice are sacrificed when Body Condition Scoring (BCS) is 2 or less, or when total weight loss of 20% is reached at any time during the study.

Therapeutic efficacy can be evaluated by median survival time. Therapeutic efficacy also can be evaluated by gross imaging. For example, lungs can be harvested and the presence, absence or size of solid tumor nodule can be compared among treatment groups and between treatment groups and untreated control group.

Example 6

Determination of the Impact of MK2 Inhibitors on Kras and Kras/p53 Driven Lung Cancers Murine models can be used to perform in vivo studies to understand the impact of MK2 inhibitors on Kras, Kras/p53 and Kras/Lkb1 driven murine lung cancers. The impact of systemic MK2 inhibition on the immune cells within Kras, Kras/p53 and Kras/Lkb1 lung cancers can be examined after a two (2) week short-term treatment with either (i) placebo; (ii) cisplatin; (iii) MK2 inhibitor; or (iv) cisplatin+MK2 inhibitor.

Three (3) to five (5) mice of each genotype (Kras and Kras/p53) with lung cancer determined by MRI screening can be treated with the respected agents ((i) placebo; (ii) cisplatin; (iii) MK2 inhibitor; or (iv) cisplatin+MK2 inhibitor) listed above for two (2) weeks. Bronchoalveolar lavage fluid (BALF) can be obtained from these mice for cytokine profiling (e.g., IL-6, TGFb1, PGRN, VEGF, GMCSG and CCL2). Lung tumor nodules can be isolated from these mice and processed into single cell suspensions. Next, the suspensions can be sorted by FACS for cancer epithelial cells and various immune cell populations (e.g., macrophages, NK, Treg, B cells, etc.).

Example 7

Efficacy Studies

If MK2 inhibitors are found to have a dramatic impact on reactivating the immune system and shrinking tumor size after two (2) weeks, chronic efficacy studies can be performed.

Ten (10) to fifteen (15) mice of each genotype (Kras and Kras/p53) with lung cancer can be treated chronically with the respected agents ((i) placebo; (ii) cisplatin; (iii) MK2 inhibitor; or (iv) cisplatin+MK2 inhibitor) listed above. Mice can be serially imaged by MRI to document responses and tumor progression. Depth of response, duration of response, response rate, progression free survival and overall survival can be measured. At the endpoint of the study, mice from the various cohorts can be euthanized and their BALF and tumor nodules collected in order to determine the mechanisms of primary and acquired resistance.

While the described invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the described invention. All such modifications are intended to be within the scope of the claims appended hereto.

---

What is claimed is:

1. A method for treating non-small cell lung cancer solid tumor comprising a population of tumor cells, the method comprising:
administering to a subject in need thereof a pharmaceutical composition comprising a therapeutic amount of a polypeptide of the amino acid sequence YARAAARQARAKALARQLGVAA (SEQ ID NO: 1), and a pharmaceutically acceptable carrier thereof,
wherein the therapeutic amount of the polypeptide is effective to inhibit kinase activity of the population of tumor cells, to reduce cancer cell proliferation, to reduce tumor size, to reduce tumor burden, to induce cancer cell death, to overcome tumor chemoresistance, to enhance tumor chemosensitivity, to slow progression of the population of tumor cells, or a combination thereof, and
wherein at least 65% of kinase activity of mitogen-activated protein kinase-activated protein kinase 2 (MK2 kinase), mitogen-activated protein kinase-activated protein kinase 3 (MK3 kinase), $Ca^{2+}$/calmodulin-dependent protein kinase I (CaMKI), and BDNF/NT-3 growth factors receptor (TrkB) is inhibited.

2. The method according to claim 1, wherein the tumor is selected from the group consisting of a primary tumor, a secondary tumor, a recurrent tumor, a refractory tumor and a combination thereof.

3. The method according to claim 2, wherein the primary tumor is selected from the group consisting of a squamous cell carcinoma, an adenocarcinoma, a large cell carcinoma and a combination thereof.

4. The method according to claim 2, wherein the secondary tumor is a metastatic tumor.

5. The method according to claim 4, wherein the metastatic tumor is a selected from the group consisting of an adrenal metastatic tumor, a bone metastatic tumor, a liver metastatic tumor, a brain metastatic tumor and a combination thereof.

6. The method according to claim 1, wherein the step of administering occurs intratracheally, parenterally, intravenously, intraperitoneally or by pulmonary administration.

7. The method according to claim 6, wherein the step of administering occurs by pulmonary administration.

8. The method according to claim 7, wherein the pulmonary administration is inhalation.

9. The method according to claim 1, wherein the pharmaceutical composition further comprises at least one additional therapeutic agent.

10. The method according to claim 9, wherein the additional therapeutic agent is a chemotherapeutic agent selected from the group consisting of afatinib dimaleate, bevacizumab, carboplatin, carboplatin-paclitaxol, ceritinib, cisplatin, crizotinib, docetaxel, erlotinib hydrochloride, gefitinib, qemcitabine-cisplatin, gemcitabine hydrochloride, mechlorethamine hydrochloride, methotrexate, paclitaxel, paclitaxel albumin-stabilized nanoparticle formulation, pemetrexed disodium, ramucirumab, vinorelbine tartrate, and a combination thereof.

11. The method according to claim 9, wherein the additional therapeutic agent is a glucocorticoid selected from the group consisting of prednisone, budesonide, mometasone furoate, fluticasone propionate, fluticasone furoate, and a combination thereof.

12. The method according to claim 9, wherein the additional therapeutic agent is a bronchodilator selected from the group consisting of a leukotriene modifer, an anticholingertic bronchodilator, a short-acting β2-agonist, and long-acting β2-agonist, and a combination thereof.

13. The method according to claim 9, wherein the additional therapeutic agent is an analgesic agent.

14. The method according to claim 9, wherein the additional therapeutic agent is an anti-infective agent.

15. The method according to claim 1, wherein the carrier is selected from the group consisting of a controlled release carrier, a delayed release carrier, a sustained release carrier, and a long-term release carrier.

16. The method according to claim 1, wherein the pharmaceutical composition is in a form of a dry powder.

17. The method according to claim 16, wherein the dry powder comprises microparticles with Mass Median Aerodynamic Diameter (MMAD) of 1 to 5 microns.

18. The method according to claim 1, wherein the pharmaceutical composition is administered via an inhalation device.

19. The method according to claim 18, wherein the inhalation device is a nebulizer.

20. The method according to claim 18, wherein the inhalation device is a metered-dose inhaler (MDI).

21. The method according to claim 18, wherein the inhalation device is a dry powder inhaler (DPI).

22. The method according to claim 18, wherein the inhalation device is a dry powder nebulizer.

23. The method according to claim 1, wherein the pharmaceutical composition comprises a first amount of the polypeptide of the amino acid sequence YARAAARQARAKALARQLGVAA (SEQ ID NO: 1) and a second amount of a chemotherapeutic agent, wherein the first amount and the second amounts together comprise an amount effective to inhibit kinase activity of the population of tumor cells, to reduce cancer cell proliferation, to reduce tumor size, to reduce tumor burden, to induce cancer cell death, to overcome tumor chemoresistance, to enhance tumor chemosensitivity, to slow progression of the population of tumor cells, or combination thereof.

24. The method according to claim 23, wherein the chemotherapeutic agent is cisplatin

* * * * *